(12) United States Patent
Yamana et al.

(10) Patent No.: US 10,381,532 B2
(45) Date of Patent: Aug. 13, 2019

(54) WAVELENGTH CONVERSION DEVICE AND LIGHTING APPARATUS

(71) Applicant: Panasonic Intellectual Property Management Co., Ltd., Osaka (JP)

(72) Inventors: Masahito Yamana, Hyogo (JP); Noboru Iizawa, Osaka (JP); Jun Hirai, Nara (JP); Yoshiyuki Nakano, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 15/765,258

(22) PCT Filed: Oct. 6, 2016

(86) PCT No.: PCT/JP2016/004500
§ 371 (c)(1),
(2) Date: Mar. 31, 2018

(87) PCT Pub. No.: WO2017/061120
PCT Pub. Date: Apr. 13, 2017

(65) Prior Publication Data
US 2018/0294390 A1 Oct. 11, 2018

(30) Foreign Application Priority Data

Oct. 9, 2015 (JP) .................................. 2015-201335
Oct. 9, 2015 (JP) .................................. 2015-201570
(Continued)

(51) Int. Cl.
*H01L 33/58* (2010.01)
*F21V 9/30* (2018.01)
(Continued)

(52) U.S. Cl.
CPC .............. *H01L 33/58* (2013.01); *F21V 5/005* (2013.01); *F21V 9/30* (2018.02); *F21V 29/502* (2015.01);
(Continued)

(58) Field of Classification Search
CPC ..... H01L 33/58; H01L 33/504; H01L 33/507; F21V 29/502; F21V 29/503; F21V 29/70;
(Continued)

(56) References Cited

U.S. PATENT DOCUMENTS 5,473,471 A * 12/1995 Yamagata ............ G02B 5/1876
359/566
2002/0080615 A1 * 6/2002 Marshall .................. F21V 5/04
362/333
(Continued)

FOREIGN PATENT DOCUMENTS

JP 2008-084396 4/2008
JP 2008-186850 8/2008
(Continued)

OTHER PUBLICATIONS

International Search Report (ISR) and Written Opinion (WO) dated Dec. 20, 2016 in International (PCT) Application No. PCT/JP2016/004500.

*Primary Examiner* — Sitaramarao S Yechuri
(74) *Attorney, Agent, or Firm* — Renner, Otto, Boisselle & Sklar, LLP

(57) ABSTRACT

A wavelength conversion device includes a light source for emitting light having a predetermined wavelength in a wavelength region from ultraviolet light to visible light, a phosphor layer for performing wavelength conversion on light which is emitted from the light source and incident on an incidence face, and an optical member which is arranged between the light source and the phosphor layer, splits and
(Continued)

separates light emitted from the light source and emits the split and separated light beams to the incidence face of phosphor layer.

14 Claims, 38 Drawing Sheets

(30) Foreign Application Priority Data

Mar. 7, 2016 (JP) .................................. 2016-043839
Mar. 7, 2016 (JP) .................................. 2016-043890

(51) Int. Cl.
| | | |
|---|---|---|
| *G02B 5/20* | (2006.01) | |
| *H01S 5/02* | (2006.01) | |
| *F21V 29/502* | (2015.01) | |
| *F21V 5/00* | (2018.01) | |
| *G03B 21/20* | (2006.01) | |
| *H04N 9/31* | (2006.01) | |
| *F21V 29/503* | (2015.01) | |
| *F21V 29/70* | (2015.01) | |
| *G02B 27/10* | (2006.01) | |
| *H01L 33/50* | (2010.01) | |
| *A61B 1/06* | (2006.01) | |
| *F21Y 115/30* | (2016.01) | |
| *F21S 2/00* | (2016.01) | |

(52) U.S. Cl.
CPC ............ *F21V 29/503* (2015.01); *F21V 29/70* (2015.01); *G02B 5/20* (2013.01); *G02B 27/1006* (2013.01); *G03B 21/204* (2013.01); *H01L 33/504* (2013.01); *H01L 33/507* (2013.01); *H01S 5/02* (2013.01); *H04N 9/3158* (2013.01); *A61B 1/0653* (2013.01); *F21S 2/00* (2013.01); *F21Y 2115/30* (2016.08)

(58) Field of Classification Search
CPC ... F21V 9/30; F21V 5/005; F21V 5/20; A61B 1/0653; G02B 27/1006; G03B 21/204; H01S 5/02; H04N 9/3158; F21Y 2115/30; F21S 2/00
See application file for complete search history.

(56) References Cited

U.S. PATENT DOCUMENTS

| | | | |
|---|---|---|---|
| 2007/0012940 A1* | 1/2007 | Suh | ........................ H01L 33/507 257/99 |
| 2009/0097121 A1 | 4/2009 | Shinoda | |
| 2011/0006323 A1 | 1/2011 | Suzuki | |
| 2011/0104935 A1 | 5/2011 | Kitamura | |
| 2012/0057364 A1 | 3/2012 | Kishimoto | |
| 2013/0286653 A1* | 10/2013 | Holman | .................. F21V 5/005 362/293 |
| 2014/0084325 A1 | 3/2014 | Yamanaka | |
| 2014/0209943 A1 | 7/2014 | Yamamoto | |
| 2014/0347843 A1 | 11/2014 | Kishimoto | |
| 2015/0226389 A1 | 8/2015 | Kasugai | |
| 2015/0263486 A1 | 9/2015 | Terasaki | |
| 2017/0074466 A1* | 3/2017 | Redpath | ............. G02B 27/0944 |

FOREIGN PATENT DOCUMENTS

| | | |
|---|---|---|
| JP | 2009-025427 | 2/2009 |
| JP | 2009-238960 | 10/2009 |
| JP | 2010-003579 | 1/2010 |
| JP | 2011-186350 | 9/2011 |
| JP | 2011-204866 | 10/2011 |
| JP | 2012-104267 | 5/2012 |
| JP | 2012-142187 | 7/2012 |
| JP | 2012-230914 | 11/2012 |
| JP | 2013-089469 | 5/2013 |
| JP | 2014-112707 | 6/2014 |
| JP | 2014-146661 | 8/2014 |
| JP | 2014-232734 | 12/2014 |
| JP | 2015-108758 | 6/2015 |
| JP | 2015-169929 | 9/2015 |
| WO | 2007/049481 | 5/2007 |
| WO | 2013/008361 | 1/2013 |
| WO | 2014/073136 | 5/2014 |

* cited by examiner

WAVELENGTH CONVERSION DEVICE AND LIGHTING APPARATUS

TECHNICAL FIELD

The present invention relates to a wavelength conversion device and a lighting apparatus.

BACKGROUND ART

There is illumination using a solid-state light source such as a laser. Under such illumination, a phosphor is irradiated with blue light emitted from the solid-state light source to generate white light. The phosphor scatters yellow light excited by a part of the blue light and the transmitted other part of the blue light, so that the white light can be generated by mixing the yellow light and the blue light.

Furthermore, the solid-state light source such as a laser has strong directivity and high energy density. Therefore, when the phosphor is directly irradiated with blue light emitted from the solid-state light source, the phosphor generates a lot of heat in an irradiated area and increases in temperature. Since the phosphor has a temperature quenching property in which the wavelength conversion efficiency of the phosphor decreases with increase of the temperature of the phosphor, it is necessary to suppress the temperature increase of the phosphor.

Therefore, Patent Literature 1 discloses a lighting apparatus in which diffusing means for diffusing light from a solid-state light source is formed on a phosphor layer. According to Patent Literature 1, an energy distribution of light from the solid-state light source is diffused by the diffusing means, so that energy concentration on the phosphor layer can be prevented (thermal load can be reduced), and temperature increase of the phosphor layer can be suppressed.

CITATION LIST

Patent Literature

PTL 1: Japanese Unexamined Patent Application Publication No. 2012-104267

SUMMARY OF THE INVENTION

Technical Problem

The foregoing prior art can reduce the thermal load on the phosphor layer, but has a problem that diffusion of a part of light from the solid-state light source causes a diffusion loss. That is, the foregoing prior art has a problem that it is difficult to achieve high output by the lighting apparatus.

The present invention has been implemented in view of the foregoing problem, and has an object to provide a wavelength conversion device that can achieve a high output while reducing a thermal load on a phosphor layer, and a lighting apparatus using the same.

Solution to Problem

In order to achieve the foregoing object, a wavelength conversion device according to an aspect of the present invention includes a light source that emits light having a predetermined wavelength in a wavelength region from ultraviolet light to visible light; a phosphor layer that performs wavelength conversion on light which is emitted from the light source and incident on an incidence face; and an optical member that is arranged between the light source and the phosphor layer, splits and separates light emitted from the light source, and projects beams of the light onto the incidence face of the phosphor layer.

Advantageous Effect of Invention

The wavelength conversion device according to an aspect of the present invention can achieve a high output while reducing a thermal load on a phosphor layer.

DESCRIPTION OF EXEMPLARY EMBODIMENTS

Embodiments will be described hereunder with reference to the drawings. The embodiments described here are respectively specific examples of the present invention. Therefore, numerical values, shapes, materials, constituent elements, arrangements and connection styles of the constituent elements, steps (processes), the order of the steps, etc. shown in the following embodiments are examples, and do not limit the present invention. Constituent elements which are not recited in independent claims out of constituent elements in the following embodiments are constituent elements which may be arbitrarily added. Furthermore, each figure is a schematic diagram, and thus it is not necessarily strictly illustrated.

Embodiment 1

[Lighting Apparatus]

First, a lighting apparatus will be exemplified and described as an applied product in which a wavelength conversion device in an embodiment is used.

Figure 1:
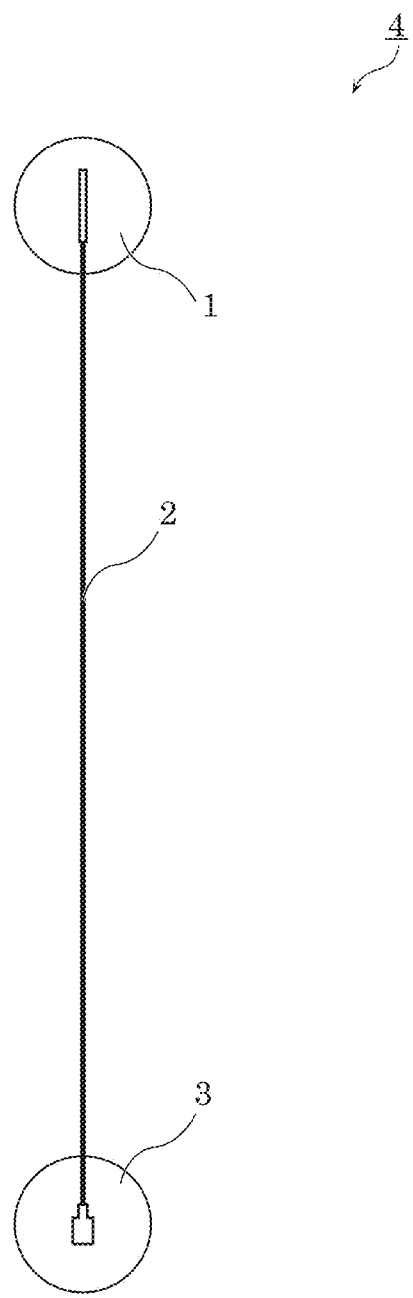
FIG. 1 is a diagram showing an example of a lighting apparatus using a wavelength conversion device in Embodiment 1.

FIG. 1 is a diagram showing an example of lighting apparatus 4 in which wavelength conversion device 1 in this embodiment is used.

Lighting apparatus 4 shown in FIG. 1 is, for example, an endoscope, a fiberscope or the like, and includes wavelength conversion device 1, optical fiber 2, and lighting appliance 3.

Optical fiber 2 is a transmission path for transmitting light to a separated place. Optical fiber 2 is configured to have a dual structure in which a core having a high refractive index is wrapped by a cladding layer having a lower refractive index than the core. Both the core and the cladding layer are formed of quarts glass or plastic which has very high transmissivity to light.

Lighting appliance 3 is used to irradiate an observation target with light which is transmitted from wavelength conversion device 1 via optical fiber 2. Lighting appliance 3 is configured by a fiber coupling formed of stainless, a ferrule formed of stainless, a lens formed of glass, a holder formed of aluminum, and an outer fence formed of aluminum, for example.

Wavelength conversion device 1 corresponds to light source means using a laser in lighting apparatus 4, and causes light to enter optical fiber 2. The details of wavelength conversion device 1 will be described hereunder.

[Wavelength Conversion Device]

Figure 2:
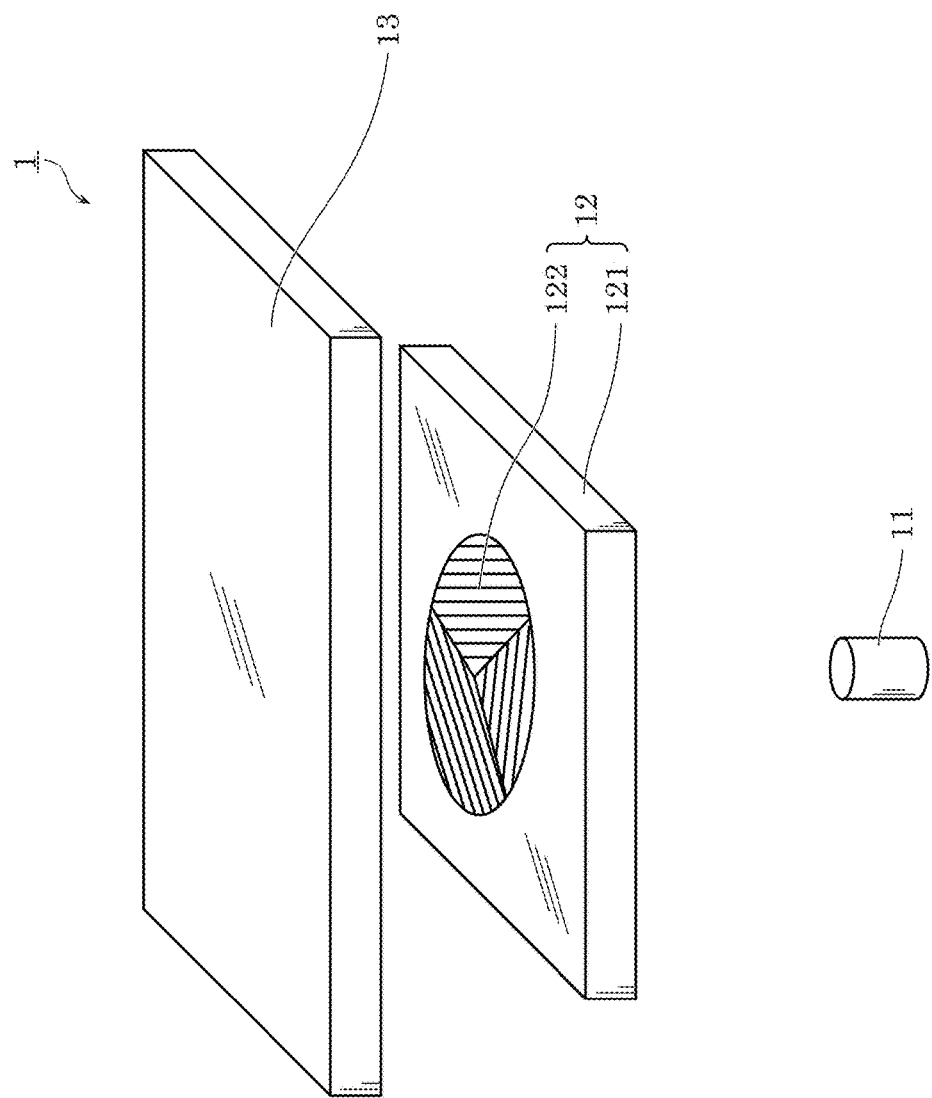
FIG. 2 is a diagram showing an example of a configuration of the wavelength conversion device in Embodiment 1.

FIG. 2 is a diagram showing an example of a configuration of wavelength conversion device 1 in this embodiment.

Wavelength conversion device 1 includes light source 11, optical member 12, and phosphor layer 13 as shown in FIG. 2.

(Light Source 11)

Light source 11 emits light having a predetermined wavelength in a wavelength region from ultraviolet light to visible light. In this embodiment, light source 11 is a laser for emitting blue light.

(Optical Member 12)

Figure 3A:
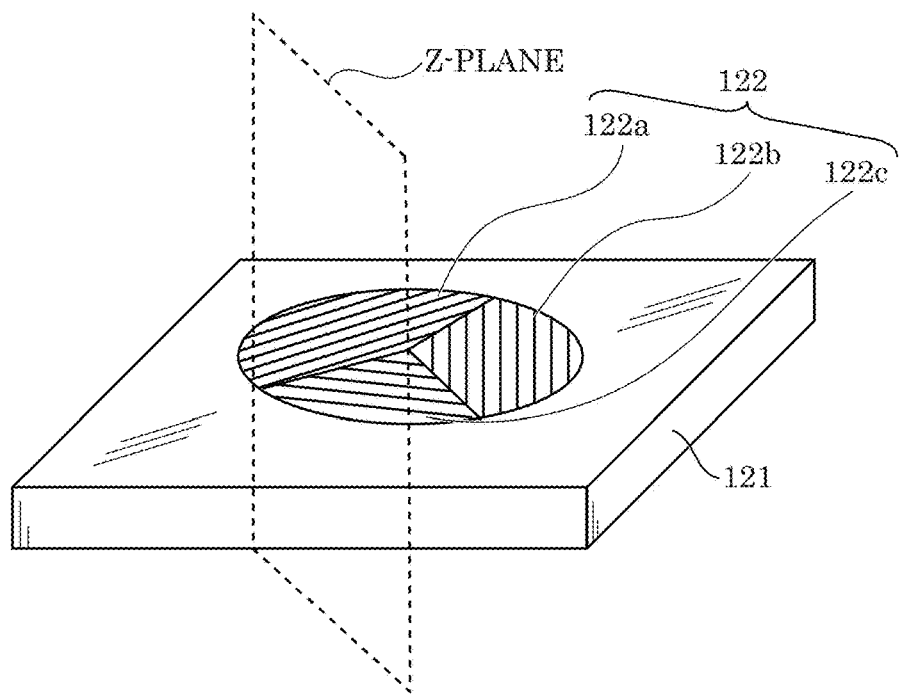
FIG. 3A is a diagram showing a perspective view of a configuration of an optical member in Embodiment 1.
Figure 3B:
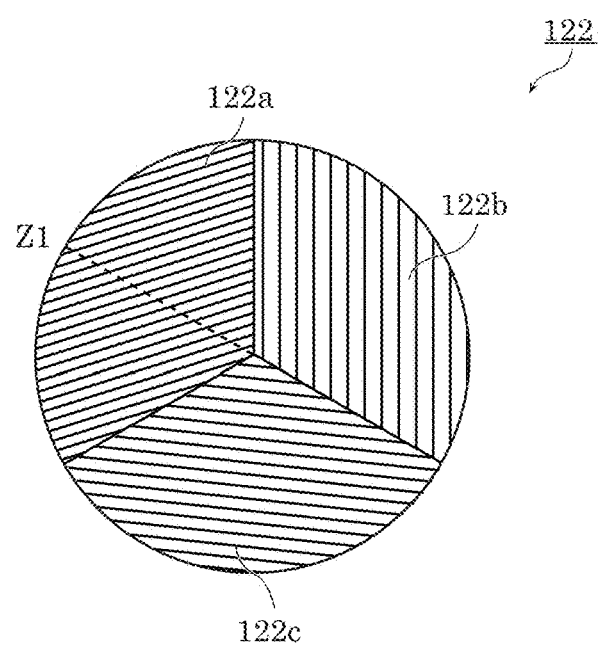
FIG. 3B is a diagram showing a top view of a diffraction type lens array shown in FIG. 3A.
Figure 3C:
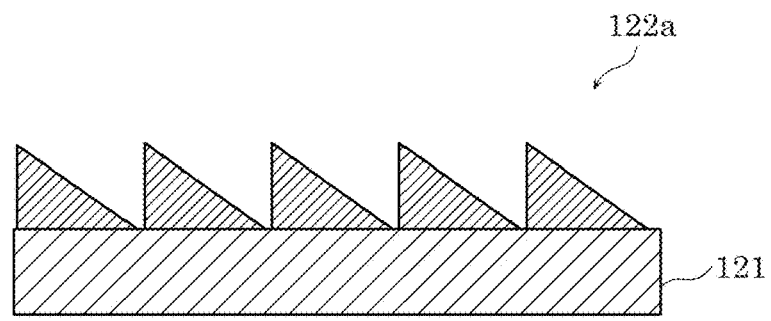
FIG. 3C is a diagram showing a cross-sectional view of the optical member on a Z-plane of FIG. 3A.

FIG. 3A is a diagram showing a perspective view of a configuration of optical member 12 in this embodiment. FIG. 3B is a diagram showing a top view of diffraction type lens array 122 shown in FIG. 3A. FIG. 3C is a diagram showing a cross-sectional view of optical member 12 on a Z-plane of FIG. 3A.

Optical member 12 is arranged between light source 11 and phosphor layer 13, splits and separates light emitted from light source 11, and projects the split and separated light beams on an incidence face of phosphor layer 13. The light which is emitted from light source 11 and split and separated by optical member 12 is projected onto an area of the incidence face of phosphor layer 13 by optical member 12 so that the split and separated light beams are not overlapped with one another, the area having a center on the optical axis of light source 11 and being larger than the diameter of light emitted from light source 11. Optical member 12 is an example of a microlens array, for example, and includes base material 121 and diffraction type lens array 122 as shown in FIG. 3A, for example.

Base material 121 is a base material of the microlens array. Diffraction type lens array 122 is formed on base material 121.

Any material such as glass or plastic may be used as a material for forming base material 121. Here, soda glass, non-alkali glass or the like may be used as the glass, for example. Furthermore, acrylic resin, polycarbonate, polyethylene terephthalate (PET), polyethylenenaphthalate (PEN) or the like may be used as the plastic. Furthermore, the material of base material 121 is required to be selected in consideration of heat resistance. It is preferable that base material 121 does not absorb light and is transparent, and also it is preferable that base material 121 is formed of a material whose extinction coefficient is substantially equal to zero.

Diffraction type lens array 122 splits and separates light emitted from light source 11, and emits the split and separated light beams to the incidence face of phosphor layer 13. The cross-sectional shape of diffraction type lens array 122 on a plane perpendicular to the incidence face of phosphor layer 13 is a sawtooth shape. Diffraction type lens array 122 includes plural areas which are set so that the arrangement direction of saw teeth is identical in the same area, but different among different areas.

This embodiment presents an example in which diffraction type lens array 122 has, for example, three areas (areas 122a, 122b, 122c) different in arrangement direction as shown in FIG. 3A and FIG. 3B. In FIG. 3A and FIG. 3B, plural linearly-arranged lens arrays are provided and the respective arrangement directions of the plural lens arrays are the same in the same area of each of the three areas (areas 122a, 122b, 122c). Here, when the wavelength of blue light of light source 11 is equal to, for example, 460 nm, the grating pitch of the plural lens arrays is equal to, for example, 5 μm, and the grating height is equal to 1 μm. Furthermore, the cross-sectional shape of diffraction type lens array 122 on a Z-plane of FIG. 3A or Z1 of FIG. 3B is a sawtooth shape as shown in FIG. 3C. Here, the Z-plane corresponds to the foregoing plane perpendicular to the incidence face of phosphor layer 13. The cross-sectional shape of diffraction type lens array 122 in area 122a is shown in FIG. 3C, and the cross-sectional shapes in the other areas 122b and 122c are likewise a sawtooth shape. That is, diffraction type lens array 122 corresponds to a so-called blazed diffraction grating. As a result, diffraction type lens array 122 can enhance a primary diffraction efficiency and reduce a loss (optical loss) of light emitted from light source 11.

As shown in top view of FIG. 3B, for example, in diffraction type lens array 122, the arrangement directions of the saw teeth in the three areas (area 122a, area 122b, area 122c) are different from one another. Such a configuration enables diffraction type lens array 122 to split and separate light emitted from light source 11, and prevent concentration of energy on the incidence face of phosphor layer 13 when the light is projected onto the incidence face of phosphor layer 13.

The material of diffraction type lens array 122 is selected according to a forming method, heat resistance and refractive index of diffraction type lens array 122. Nanoimprint, print, photolithography, EB lithography, particle orientation or the like is available as the method of forming diffraction type lens array 122. When diffraction type lens array 122 is formed, for example by nanoimprint or print, UV curing resin such as epoxy resin or acrylic resin, thermoplastic resin such as polymethyl methacrylate (PMMA) may be selected as the material of diffraction type lens array 122. Furthermore, in consideration of heat resistance, glass or quartz may be selected as the material of diffraction type lens array 122, and diffraction type lens array 122 may be formed by photolithography or EB lithography. It is preferable that diffraction type lens array 122 is formed of a material having the same level refractive index as base material 121 so that light from base material 121 easily enters diffraction type lens array 122. Furthermore, it is preferable that diffraction type lens array 122 does not absorb light and is transparent as in the case of base material 121, and also it is preferable that diffraction type lens array 122 is formed of a material whose extinction coefficient is substantially equal to zero.

(Phosphor Layer 13)

Phosphor layer 13 generates white light from blue light emitted from light source 11, and projects the generated white light onto optical fiber 2.

More specifically, phosphor layer 13 has a function of performing wavelength conversion on a part of light entering from the lower surface (incidence face) shown in FIG. 2. In this embodiment, upon incidence of blue light from light source 11, phosphor layer 13 emits yellow light excited by a part of the incident blue light. Furthermore, phosphor layer 13 emits (transmits) the other part of the incident blue light. In phosphor layer 13, the blue light and the yellow light are mixed with each other and emitted, so that phosphor layer 13 emits white light.

Phosphor layer 13 is formed, for example, in a flat-plate shape as shown in FIG. 2. Phosphor layer 13 includes phosphor, and is formed by covering the phosphor with resin such as silicon or epoxy. A loss caused by wavelength conversion is changed to heat. Since phosphor layer 13 has a temperature quenching property in which the wavelength conversion efficiency decreases as the temperature of phosphor layer 13 increases, dissipation of phosphor layer 13 is very important. Although not specifically illustrated here, it is desirable that phosphor layer 13 is supported by a dissipation plate formed of a material having a high thermal conductivity such as Al, for example. Furthermore, a material having a high thermal conductivity, for example, inorganic oxide such as ZnO may be added to the resin for forming phosphor layer 13, thereby enhancing the heat dissipation performance. The incidence face of phosphor layer 13 may be provided with a microstructure so that light easily enters phosphor layer 13 or heat dissipation from the incidence face is easily performed.

(Operation of Wavelength Conversion Device 1)

Next, the operation of wavelength conversion device 1 configured as described above will be described.

Figure 4:
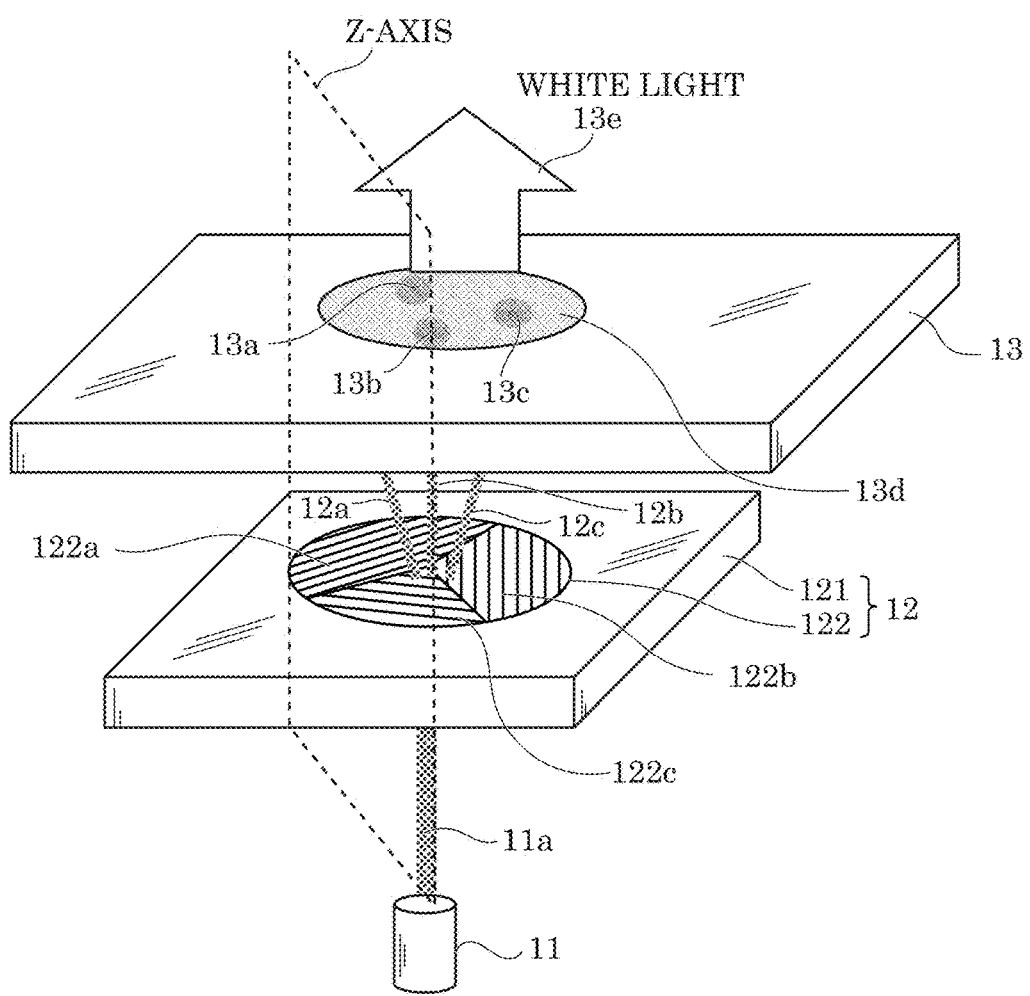
FIG. 4 is a diagram showing an operation of the wavelength conversion device in Embodiment 1.
Figure 5:
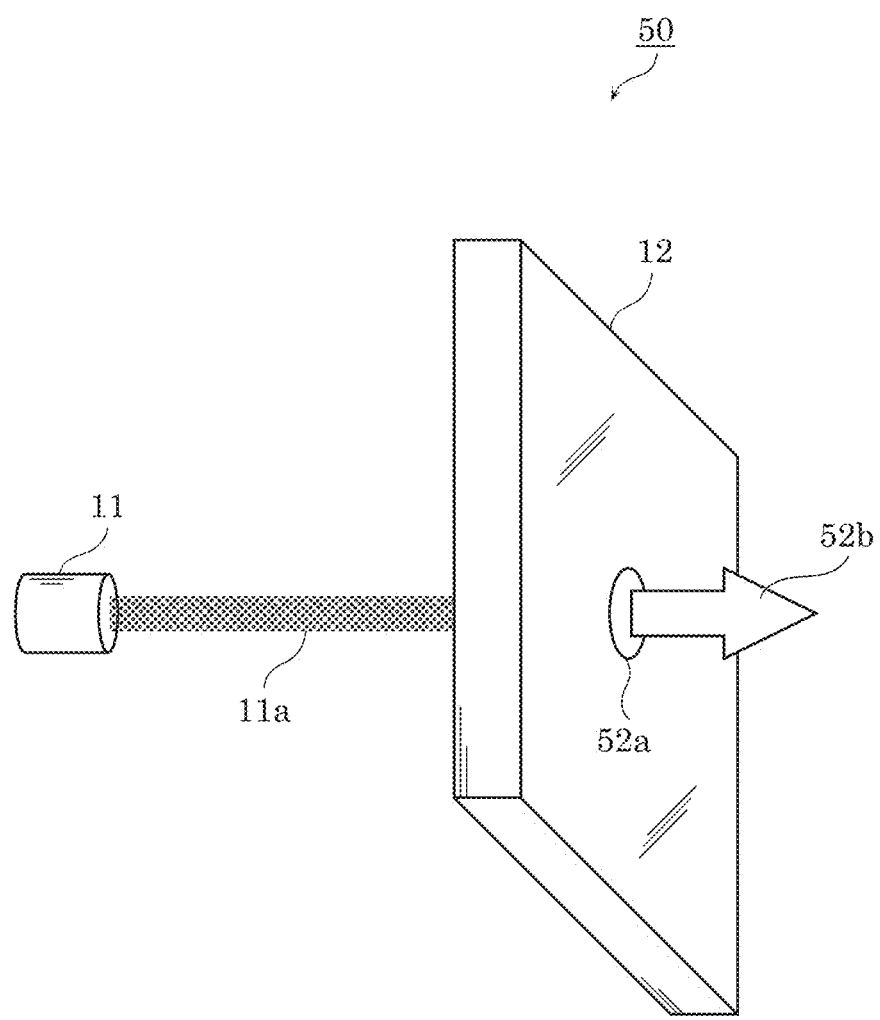
FIG. 5 is a diagram showing an operation of a comparative example.

FIG. 4 is a diagram showing the operation of wavelength conversion device 1 according to this embodiment. FIG. 5 is a diagram showing the operation of a comparative example.

As shown in FIG. 4, wavelength conversion device 1 according to this embodiment includes optical member 12 arranged between light source 11 and phosphor layer 13, which enables wavelength conversion device 1 to split and separate light 11a emitted from light source 11 into three light beams (light beam 12a, light beam 12b, light beam 12c), and emit the split and separated light beams to the incidence face of phosphor layer 13. As described above, light 11a of light source 11 can be split and separated into light beam 12a, light beam 12b, and light beam 12c and projected onto phosphor layer 13 without greatly changing the spot diameter of light 11a of light source 11. Since the split and separated light beams (light beam 12a, light beam 12b, light beam 12c) are incident on different areas of the incidence face in phosphor layer 13, it can be understood that concentration of energy on the incidence face of phosphor layer 13 can be prevented. Phosphor layer 13 can generate white light 13e from the light beams (light beam 12a, light beam 12b, light beam 12c) incident on the different areas of the incidence face.

As described above, wavelength conversion device 1 according to this embodiment can prevent concentration of energy on the incidence face of phosphor layer 13, and suppress temperature increase of phosphor layer 13, so that all the amount of light emitted from light source 11 can be emitted to phosphor layer 13 with no loss. That is, according to wavelength conversion device 1 in this embodiment, the temperature increase of phosphor layer 13 can be suppressed even when the energy of light emitted from light source 11 is increased, so that a high output can be achieved.

A comparative example shown in FIG. 5 presents wavelength conversion device 50 that does not include optical member 12 in this embodiment.

In wavelength conversion device 50 of the comparative example shown in FIG. 5, light 11a emitted from light source 11 is not split and separated, and is directly emitted to one area 52a of the incidence face of phosphor layer 13 to generate white light 52b in area 52a. However, the energy of light 11a concentrates on one area 52a of phosphor layer 13, so that it is impossible to suppress temperature increase of area 52a. That is, as wavelength conversion device 50 in the comparative example is used more frequently, the temperature of area 52a increases, and the wavelength conversion efficiency decreases, so that it is required to restrict the output of light source 11 in order to reduce the energy of light 11a.

[Operation Simulation of Wavelength Conversion Device 1]

Next, an operation simulation of wavelength conversion device 1 according to this embodiment will be described.

Figure 6:
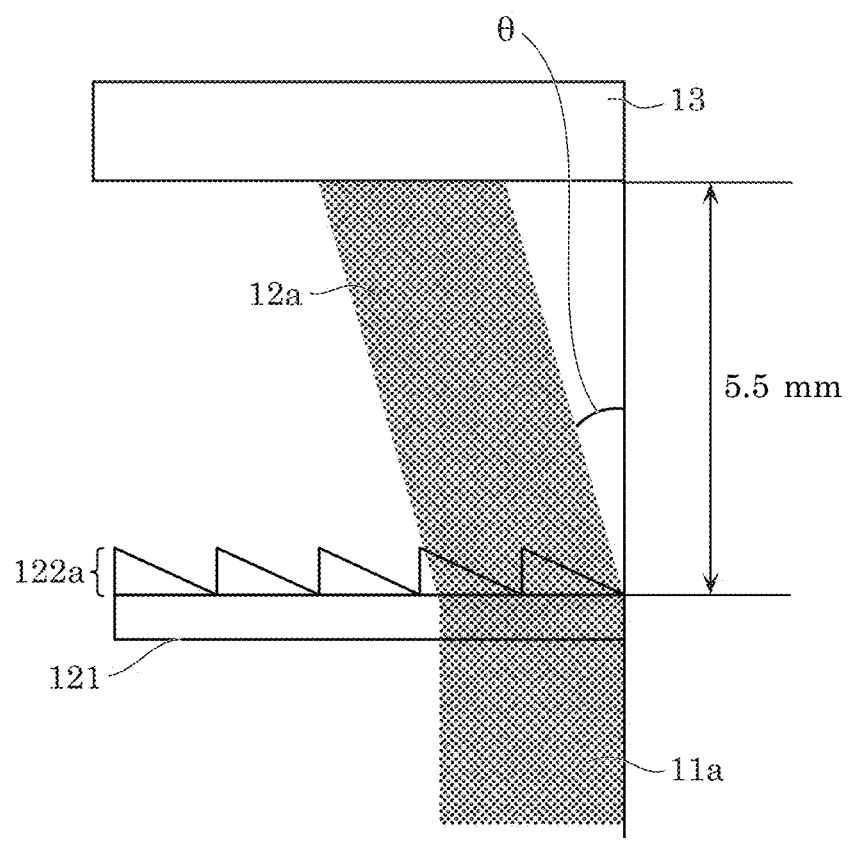
FIG. 6 is a diagram showing a simulation model of the wavelength conversion device in Embodiment 1.
Figure 7:
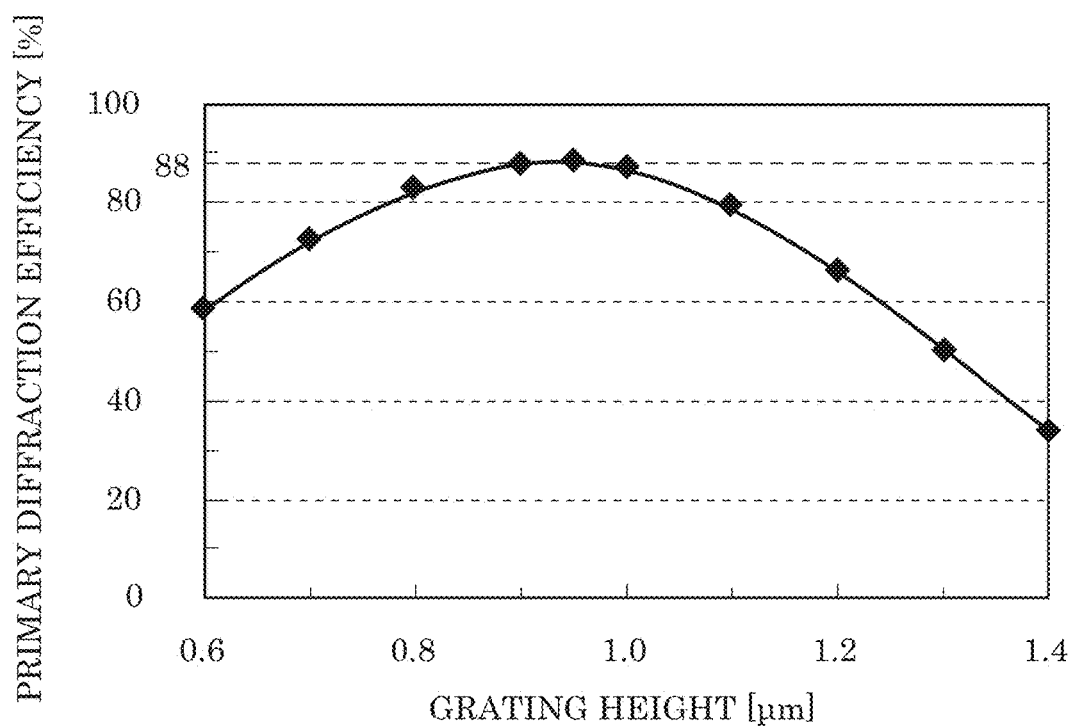
FIG. 7 is a diagram showing a simulation result of the relationship between a primary diffraction efficiency and a grating height.

FIG. 6 is a diagram of a simulation model of wavelength conversion device 1 according to this embodiment. FIG. 7 is a diagram showing a simulation result of the relationship between the primary diffraction efficiency and the grating height.

FIG. 6 shows a simulation model of a cross-section on the z-plane shown in FIG. 4 of wavelength conversion device 1 according to this embodiment. In the simulation model of FIG. 6, the distance between optical member 12 and phosphor layer 13 was set to 5.5 mm, the grating pitch of diffraction type lens array 122 in area 122a was set to 5 µm, and the angle θ (diffraction angle) between diffracted light 12a of light 11a of light source 11 and light 11a was set to 5.2 degrees. The relationship between the primary diffraction efficiency and the grating height was simulated by using the simulation model shown in FIG. 6. The result is shown in FIG. 7. The wavelength of blue light of light source 11 is set to 460 nm. The primary diffraction efficiency is a value indicating how much energy can be extracted as diffracted light out of the energy of light 12a of light source 11 as incident light.

As shown in FIG. 7, the primary diffraction efficiency is greater than or equal to 80% for the grating height in the range from 0.8 µm to 1.1 µm, and the primary diffraction efficiency is equal to 88% for the grating height around 1.0 µm. Accordingly, it is understood that diffraction type lens array 122 can enhance the primary diffraction efficiency and reduce the loss (optical loss) of light emitted from light source 11 by forming sawtooth-shaped lens arrays having the grating pitch of 5 µm and the grating height of 1.0 µm.

[Advantageous Effects, Etc.]

As described above, according to wavelength conversion device 1 in this embodiment, the optical member for separating and splitting light entering from light source 11 by diffraction is provided between light source 11 and phosphor layer 13. As a result, a high output can be achieved while reducing a thermal load on phosphor layer 13.

More specifically, the wavelength conversion device according to an aspect of the present invention includes light source 11 that emits light having a predetermined wavelength in a wavelength region from ultraviolet light to visible light, phosphor layer 13 that performs wavelength conversion on light from light source 11 incident on an incidence face, and optical member 12 that is disposed between light source 11 and phosphor layer 13, splits and separates the light emitted from light source 11 and projects beams of the light onto the incidence face of phosphor layer 13.

Accordingly, even when light emitted from light source 11 is split and separated, and emitted to the incidence face of phosphor layer 13, concentration of energy on the incidence face of phosphor layer 13 can be prevented. As a result, since the temperature increase of phosphor layer 13 can be suppressed even when the energy of light emitted from light source 11 is increased, a high output of wavelength conversion device 1 can be achieved.

Here, for example, the light emitted from light source 11 and split and separated by optical member 12 is projected onto an area of the incidence face which has a center set on the optical axis of light source 11 and is larger than the diameter of light emitted from light source 11 without the beams of the light overlapping with one another.

Furthermore, optical member 12 is a microlens array, for example.

As a result, the optical loss can be reduced by the microlens array for diffracting incident light to achieve a high output.

Here, for example, the cross-sectional shape of the microlens array (diffraction type lens array 122) taken along the plane perpendicular to the incidence face is a sawtooth shape.

Accordingly, since diffraction type lens array 122 corresponds to a so-called blazed diffraction grating, the primary diffraction efficiency can be enhanced, the loss (optical loss) of light emitted from light source 11 can be reduced, and the output of wavelength conversion device 1 can be increased.

Furthermore, for example, the microlens array (diffraction type lens array 122) has plural areas in which the arrangement direction of saw teeth is identical in the same area and different between different areas. Here, the plural areas contain three areas, for example.

Accordingly, even when light emitted from light source 11 is split and separated and emitted to the incidence face of phosphor layer 13, concentration of energy on the incidence face of phosphor layer 13 can be prevented. As a result, even when the energy of light emitted from light source 11 is increased, the temperature increase of phosphor layer 13 can be suppressed, so that the output of wavelength conversion device 1 can be increased.

(Variation)

The configuration of wavelength conversion device 1 according to the present invention is not limited to that described in Embodiment 1. A microlens array having a diffraction type lens array different from diffraction type lens array 122 described above may be further provided on phosphor layer 13. An example in this case will be described hereunder as a variation.

Figure 8:
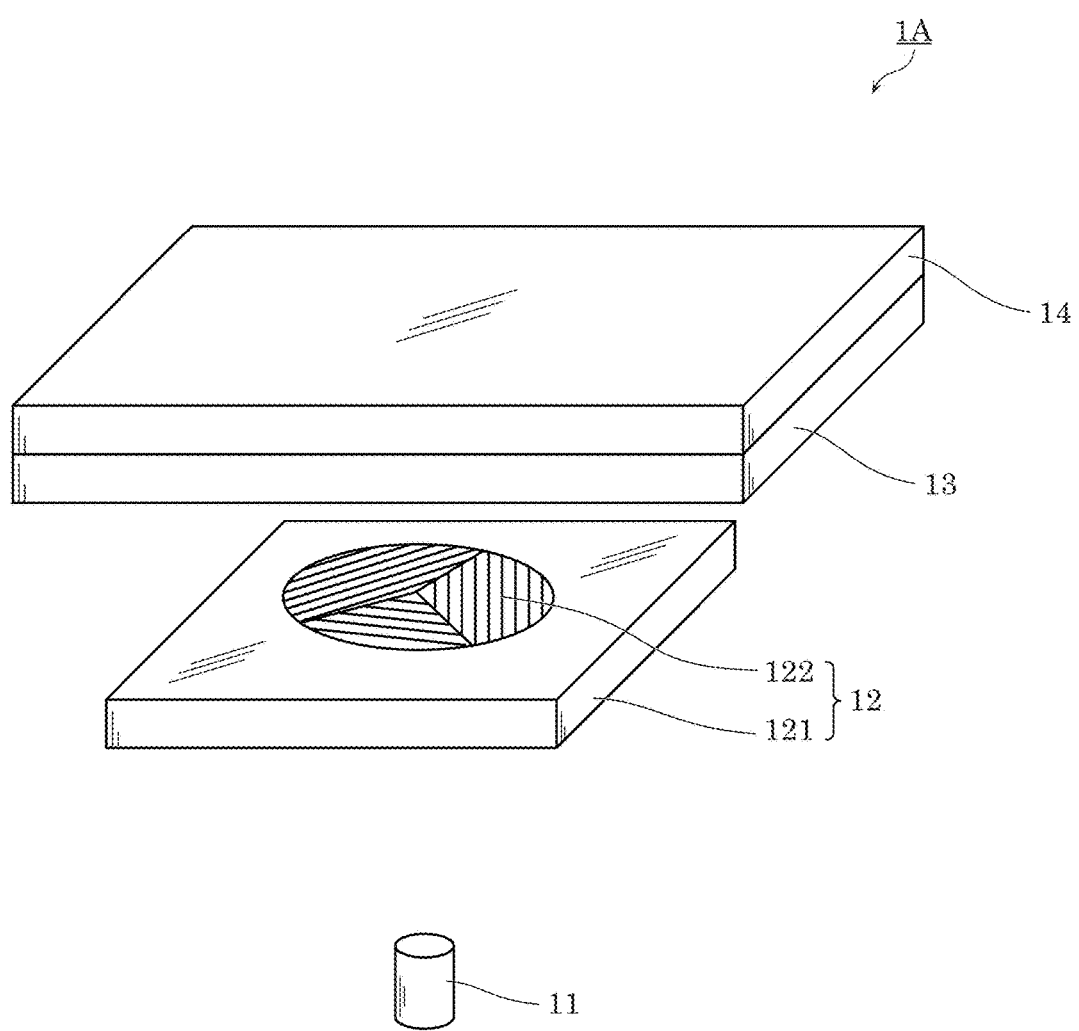
FIG. 8 is a diagram showing an example of a configuration of a wavelength conversion device in a variation.
Figure 9:
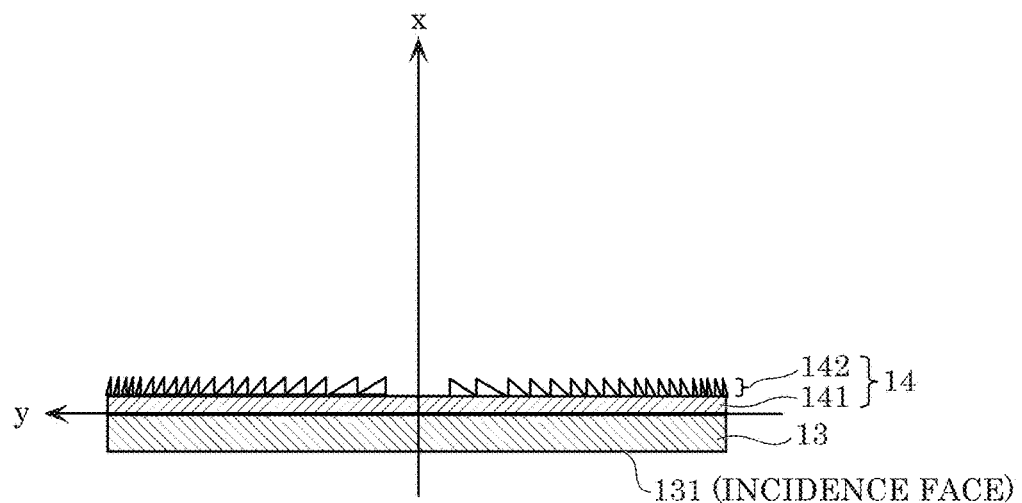
FIG. 9 is a cross-sectional view of a microlens array in the variation.
Figure 10:
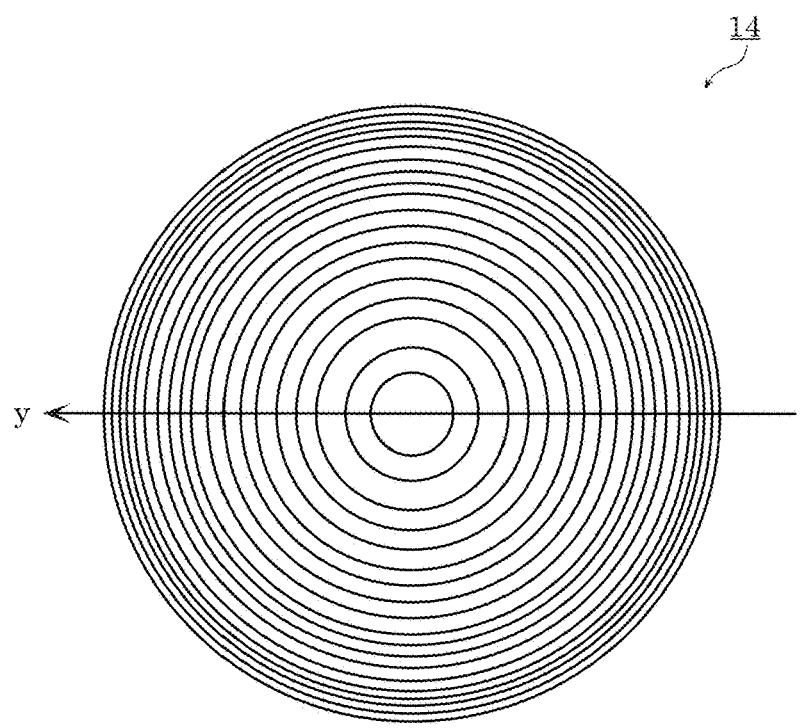
FIG. 10 is a top view of the microlens array shown in FIG. 9.

FIG. 8 is a diagram showing an example of a configuration of a wavelength conversion device according to this variation. FIG. 9 is a cross-sectional view of microlens array 14 in this variation. FIG. 10 is a top view of microlens array 14 shown in FIG. 9. The same elements as shown in FIG. 2 are represented by the same reference marks, and detailed description thereof is omitted.

Microlens array 14 includes base material 141 and diffraction type lens array 142.

Base material 141 is a base material of microlens array 14, and is formed in a flat-plate shape. In this variation, base material 141 is formed on phosphor layer 13. Diffraction type lens array 142 is formed on base material 141.

The detailed description of a material for forming base material 141 is omitted because it is similar to base material 121, but it is preferable that base material 141 is formed of a material having the same level refractive index as phosphor layer 13 to facilitate entry of light from phosphor layer 13. Here, the same level refractive index means that the difference in refractive index between base material 141 and phosphor layer 13 is less than or equal to ±0.2. Furthermore, although not specifically shown, it is preferable that both phosphor layer 13 and base material 141 are adhesively attached to each other by an adhesive layer having the same level refractive index as both phosphor layer 13 and base material 141. Acrylic resin, epoxy resin or the like may be used as the material of the adhesive layer. It is preferable that base material 141 and the adhesive layer do not absorb light, and are transparent, and also it is preferable that they are formed of materials whose extinction coefficients are substantially equal to zero.

Diffraction type lens array 142 emits, from an emission face thereof, a wavelength-converted part of light in phosphor layer 13 and the other part of light transmitted through phosphor layer 13. The emission face of diffraction type lens array 142 is provided with plural diffraction lenses for diffracting and emitting the wavelength-converted part of light and the other transmitted part of light as shown in FIG. 9. The plural diffraction lenses are provided, for example, concentrically on the emission face as shown in FIG. 10. In this embodiment, description is made so that the cross-section of the diffraction lenses on a plane perpendicular to the emission face is sawtooth-shaped. However, the cross-sectional shape is not limited to the sawtooth shape, but may be a rectangular, triangular or hemispherical shape.

The plural diffraction lenses are provided so as to diffract a part of blue light wavelength-converted to yellow light in phosphor layer 13, and blue light transmitted through phosphor layer 13, and converge the wavelength-converted yellow light and the transmitted blue light to an opening portion of optical fiber 2 which is a predetermined area. Therefore, the pitch of the plural diffraction lenses differs for each predetermined section (zone). The pitch of the plural diffraction lenses is narrowed as the position thereof shifts from the center of diffraction type lens array 142 to the periphery thereof.

The detailed description on the material of diffraction type lens array 142 is omitted because it is similar to that of diffraction type lens array 122, but it is preferable that diffraction type lens array 142 is formed of a material having the same level refractive index as base material 141 to facilitate entry of light from base material 141. Furthermore, it is preferable that diffraction type lens array 142 does not absorb light and is transparent as in the case of base material 141, and also it is preferable that diffraction type lens array 142 is formed of a material whose extinction coefficient is substantially equal to zero.

Microlens array 14 may be formed directly on (formed integrally with) phosphor layer 13 to facilitate entry of light from phosphor layer 13 to diffraction type lens array 142. In this case, microlens array 14 may be formed of resin constituting phosphor layer 13, or formed of a material having the same level refractive index as phosphor layer 13.

(Others)

Embodiment 1 described above is merely one example, and it is needless to say that various modifications, additions, omissions, etc. may be performed.

Furthermore, configurations realized by arbitrarily combining the constituent elements and functions described in Embodiment 1 are contained in the scope of the present invention. Additionally, configurations obtained by applying various modifications conceivable by a person skilled in the art to Embodiment 1, and configurations realized by arbitrarily combining the constituent elements and functions described in Embodiment 1 without departing from the subject matter of the present invention are contained in the present invention.

For example, a lighting apparatus using wavelength conversion device 1 according to Embodiment 1 is contained in the present invention. Use of wavelength conversion device 1 according to Embodiment 1 in a lighting apparatus enables the lighting apparatus to be more compact as compared with a lighting apparatus using an LED light source.

In Embodiment 1 and the variation described above, diffraction type lens array 122 is described as having the three areas (areas 122a, 122b, 122c) which are different in arrangement direction as shown in FIG. 3A and FIG. 3B, but the present invention is not limited to this configuration. It is needless to say that diffraction type lens array 122 has any number of areas such as two areas or four areas insofar as concentration of energy on the incidence face of phosphor layer 13 can be prevented even when light emitted from light source 11 is split and separated, and emitted to the incidence face of phosphor layer 13.

The size of diffraction type lens array 122 may be merely larger than the spot diameter of light of light source 11, and it may be set to any value under a condition that a light flux of light emitted from light source 11 is not changed.

Embodiment 2

In this embodiment, a luminaire which is enhanced in heat dissipation efficiency while preventing increase in size will be described. The same constituent elements are represented by the same reference marks, and description thereof may be omitted. In the following description, description using XYZ coordinate axes shown in each figure may be made.

Figure 11:
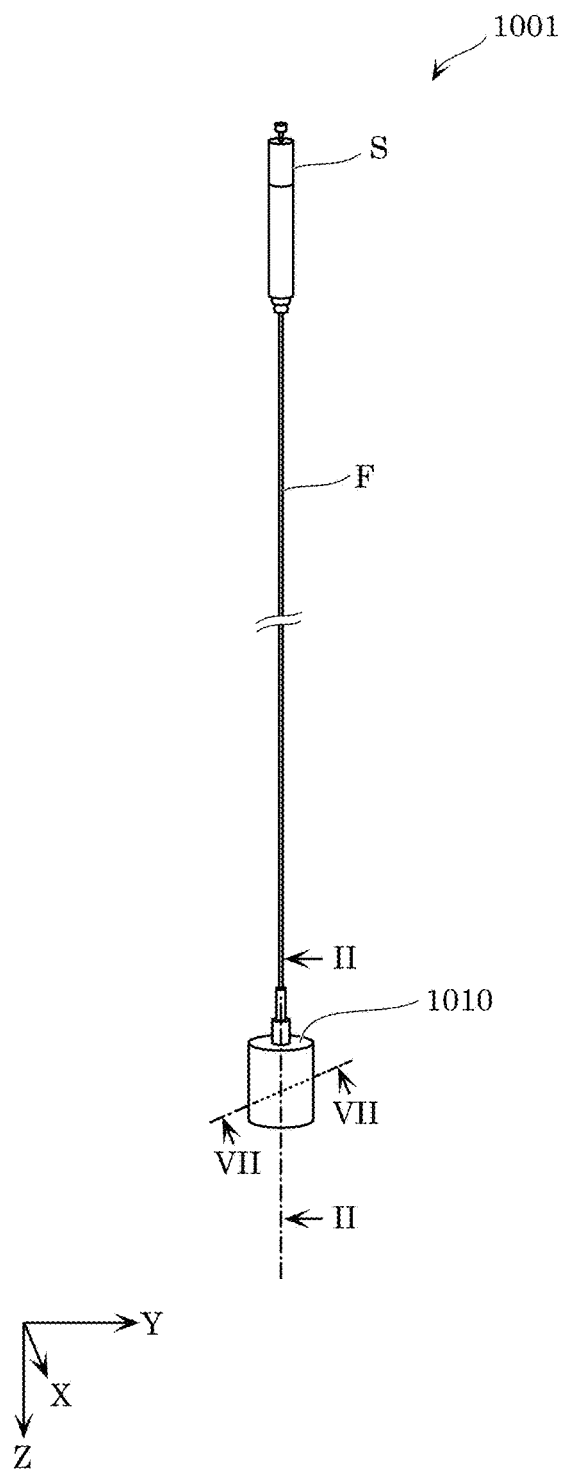
FIG. 11 is an external view of a lighting apparatus in Embodiment 2.

FIG. 11 is an external view of lighting apparatus 1001 according to Embodiment 2.

As shown in FIG. 11, lighting apparatus 1001 includes light source S, optical fiber F, and luminaire 1010.

Light source S is a light source for emitting light, and for example, it is a laser diode (LD) or a light emitting diode (LED). More specifically, light source S is LD or LED for emitting blue light, but the color of light emitted from light source S is not limited to the foregoing color.

Optical fiber F is configured to have a dual structure in which a core having a high refractive index is wrapped by a cladding layer having a low refractive index. Optical fiber F functions as a light transmission path for leading light emitted from light source S to luminaire 1010. The core and the cladding layer are formed of quartz glass or plastic which has very high transmissivity to light.

Luminaire 1010 is a luminaire for emitting light transmitted from light source S through optical fiber F to the outside of luminaire 1010, thereby illuminating the surroundings of luminaire 1010. Luminaire 1010 has a phosphor layer for converting the color (wavelength) of the overall or a part of light received from optical fiber F. For example, the phosphor layer is formed by sealing a yellow phosphor for converting blue light to yellow light with resin or the like. In this case, luminaire 1010 converts a part of blue light transmitted from light source S to yellow light by the yellow phosphor to generate white light, and emits white light to the surroundings of luminaire 1010.

The configuration of luminaire 1010 will be described hereinafter in detail.

Figure 12:
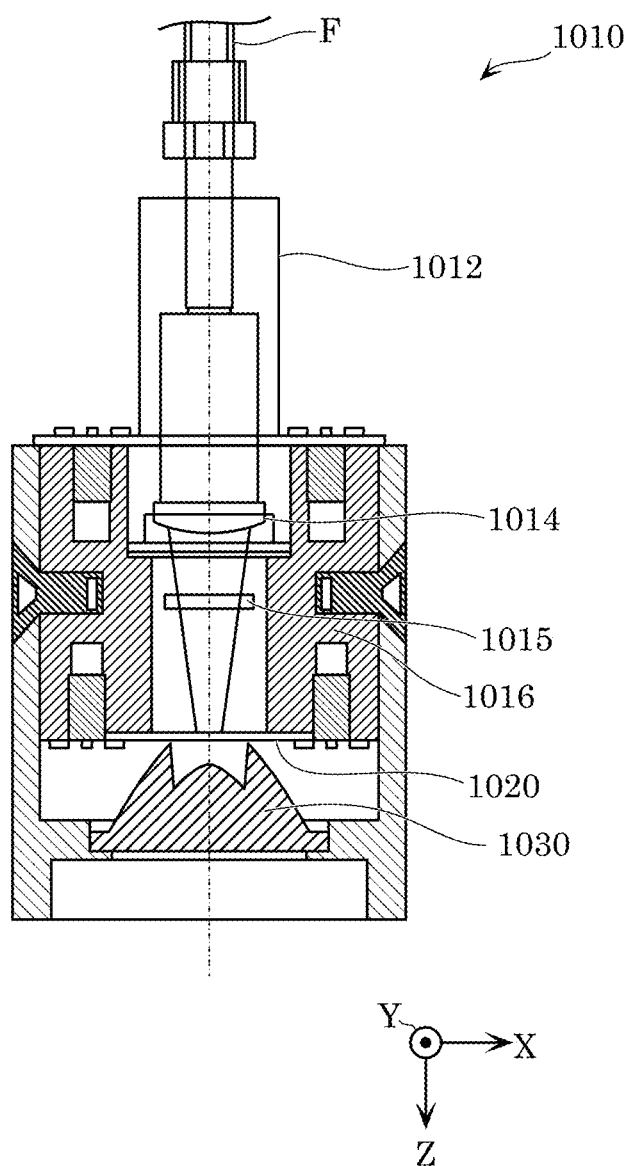
FIG. 12 is a cross-sectional view showing an internal configuration of a luminaire included in the lighting apparatus in Embodiment 2.

FIG. 12 is a cross-sectional view showing an internal configuration of luminaire 1010 included in lighting apparatus 1001 according to Embodiment 2. FIG. 12 is a diagram showing a cross-section shown by II-II line in FIG. 11 of luminaire 1010.

As shown in FIG. 12, luminaire 1010 includes fiber coupling 1012, lenses 1014 and 1030, lens array 1015, holder 1016, and phosphor member 1020.

Fiber coupling 1012 is an optical member which is connected to optical fiber F, and leads light transmitted from light source S through optical fiber F in a Z-axis plus direction into luminaire 1010.

Lens 1014 is an optical member for changing the optical path of light introduced through fiber coupling 1012.

Lens array 1015 is an optical member for changing the optical path of light emitted from lens 1014. Specifically, lens array 1015 changes (separates) the optical path of introduced light so that the introduced light is split into plural (for example, three) light beams traveling along respective optical paths, and the split light beams reach plural respective positions on phosphor member 1020. A specific configuration of lens array 1015 will be described later by presenting a specific example. Lens array 1015 may be arranged at any position between fiber coupling 1012 and phosphor member 1020. Particularly, lens array 1015 may be arranged in contact with lens 1014, or may be formed as a part of lens 1014 (that is, molded integrally with lens 1014).

Holder 1016 is a housing for accommodating respective constituent elements of luminaire 1010 therein.

Phosphor member 1020 is a member containing a phosphor which receives light passing through lens array 1015, converts the color of the received light, and emits the converted light. Phosphor member 1020 has a heat transfer plate and a heat dissipation plate which serve as a heat dissipation mechanism for dissipating heat generated by the phosphor to the outside of luminaire 1010. The configurations of these elements will be described in detail later.

Lens 1030 is an optical member for adjusting a light distribution characteristic when light emitted from phosphor member 1020 is emitted to the outside of luminaire 1010 (in the Z-axis plus direction). Lens 1030 sets the light distribution characteristic to narrow-angle light distribution or wide-angle light distribution based on the shape of lens 1030. Lens 1030 having an appropriate light distribution characteristic may be adopted according to intended use of luminaire 1010.

The detailed configurations of phosphor member 1020, etc. of luminaire 1010 will be described hereinafter.

Figure 13:
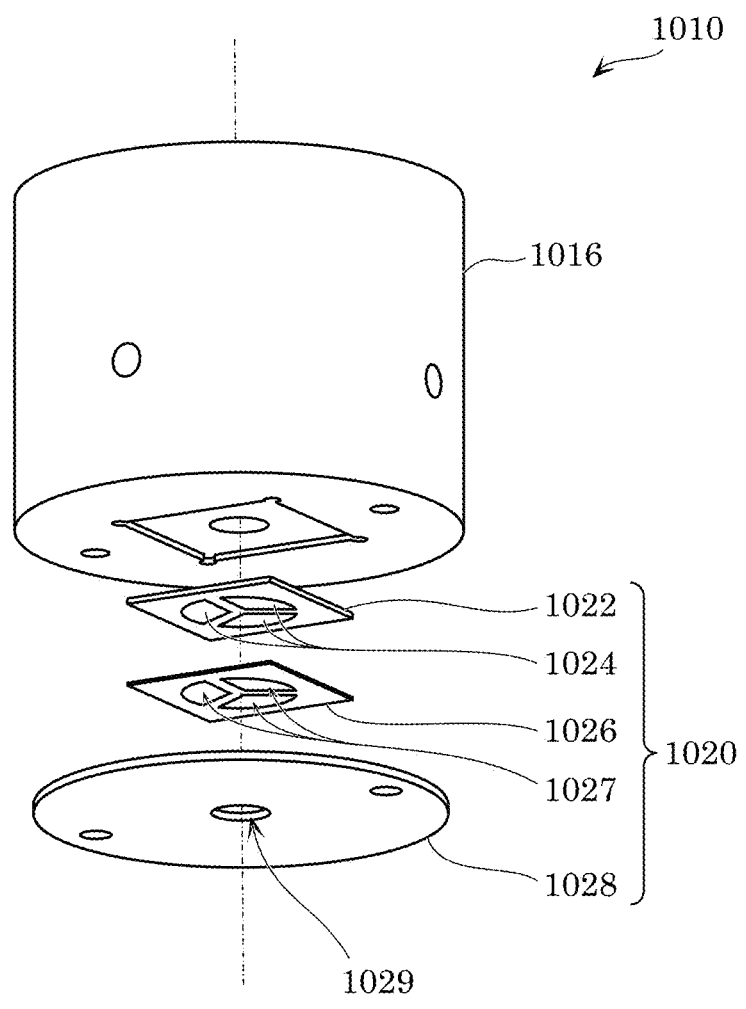
FIG. 13 is an exploded perspective view of a holder and a phosphor member included in the luminaire in Embodiment 2.
Figure 14:
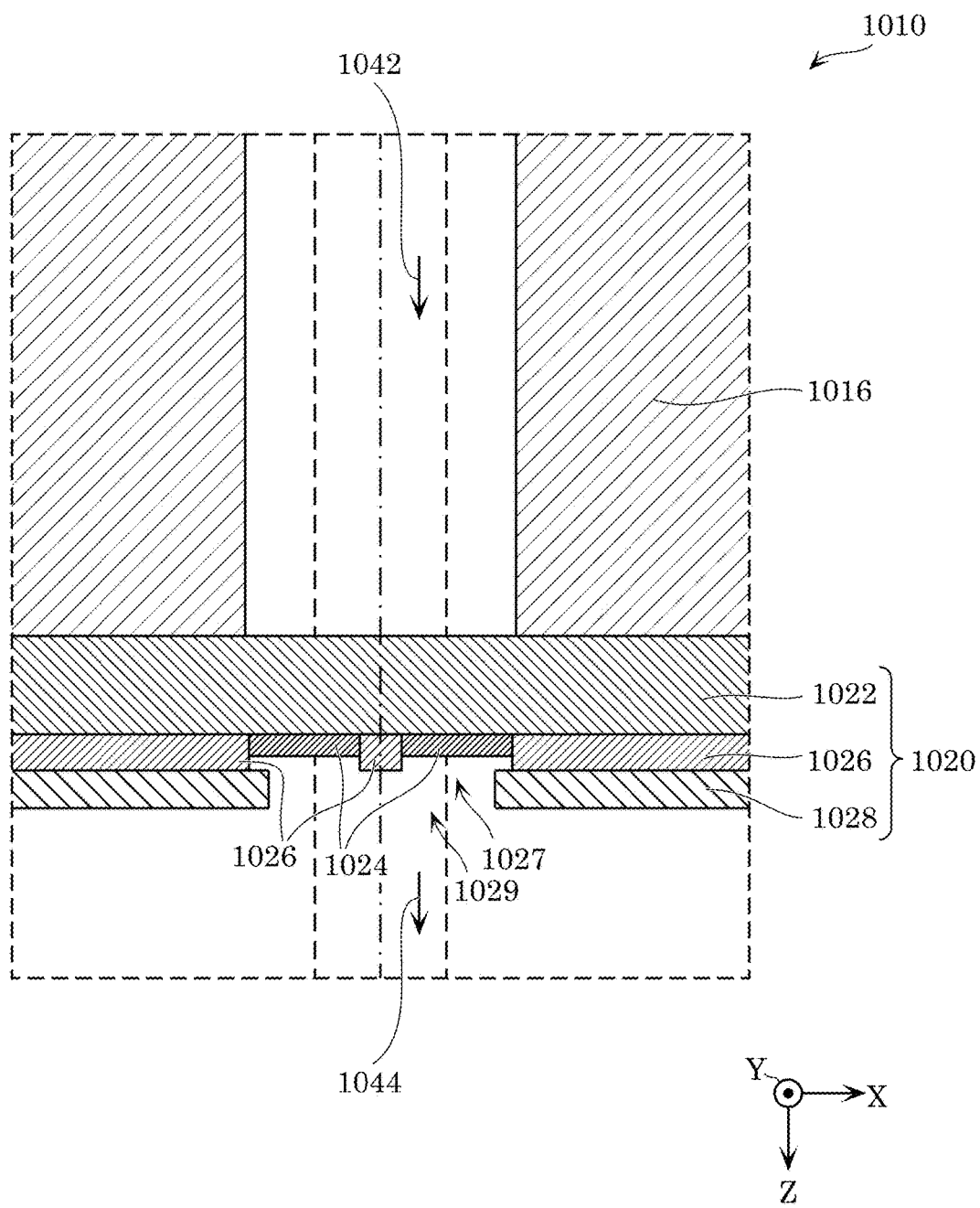
FIG. 14 is a cross-sectional view of the holder and the phosphor member included in the luminaire in Embodiment 2.

FIG. 13 is an exploded perspective view of holder 1016 and phosphor member 1020 included in luminaire 1010 in this embodiment. FIG. 14 is a cross-sectional view of holder 1016 and phosphor member 1020 included in luminaire 1010 in this embodiment. The cross-sectional view shown in FIG. 14 is an enlarged view in which the neighborhood of holder 1016 and phosphor member 1020 in cross-sectional view shown in FIG. 12 is enlarged.

As shown in FIG. 13 and FIG. 14, phosphor member 1020 includes board 1022, phosphor layer 1024, heat transfer plate 1026, and heat dissipation plate 1028.

Board 1022 is a light-transmissive board. Board 1022 is irradiated with light from light source S via optical fiber F. Board 1022 has a portion provided with phosphor layer 1024 for converting the color of light received from light source S via optical fiber F. A case where phosphor layer 1024 is provided on board 1022 by coating phosphor layer 1024 on board 1022 will be described as an example. However, the method of providing phosphor layer 1024 on board 1022 is not limited to the foregoing method. Here, a surface having a portion on which phosphor layer 1024 is coated is also referred to as a first surface, and a surface opposite to the first surface is also referred to as a second surface. A case where light from optical fiber F is irradiated from the second surface side will be described as an example. Board 1022 is a sapphire substrate, for example.

Any material such as glass or plastic may be used as a material for forming board 1022. Here, for example, soda glass, non-alkali glass or the like may be used as the glass. Furthermore, acrylic resin, polycarbonate, polyethylene terephthalate (PET), polyethylenenaphthalate (PEN) or the like may be used as the plastic. When board 1022 is formed of a material which does not absorb light and is transparent, in other words, a material whose extinction coefficient is substantially equal to zero, the amount of light transmitted through board 1022 can be increased, resulting in an advantage that the amount of light emitted from luminaire 1010 to the surroundings can be increased.

Phosphor layer 1024 is a wavelength conversion member for receiving light entering from light source S via optical fiber F and fiber coupling 1012, and converting the color (wavelength) of the received light by phosphor particles. Phosphor layer 1024 generates heat when converting the color of light.

Specifically, phosphor layer 1024 includes yellow phosphor particles for receiving blue light from light source S and emitting yellow light, for example, yttrium-aluminum-garnet (YAG)-based phosphor particles, and is formed by sealing these phosphor particles with resin such as silicon or epoxy. Phosphor layer 1024 generates white light by color-mixing of yellow light to which a part of blue light emitted from light source S is converted by the phosphor particles, and the remaining part of the blue light, and emits the white light in the Z-axis plus direction. When phosphor layer 1024 is left under high-temperature atmosphere, the light color conversion efficiency thereof generally decreases (deteriorates). Therefore, luminaire 1010 appropriately dissipates heat generated from phosphor layer 1024 to the outside of luminaire 1010 by heat transfer plate 1026 and heat dissipation plate 1028 which serve as the heat dissipation mechanism, thereby avoiding increase of the temperature of phosphor layer 1024. The heat dissipation performance may be enhanced by mixing the resin for forming phosphor layer 1024 with a material having a high thermal conductivity, for example, inorganic oxide such as ZnO.

Heat transfer plate 1026 is a plate-shaped heat transfer body for transferring heat generated by phosphor layer 1024 to heat dissipation plate 1028. Heat transfer plate 1026 is arranged in surface contact with board 1022, heat generated by phosphor layer 1024 is transferred to heat transfer plate 1026 via board 1022, and heat transfer plate 1026 further transfers the heat to heat dissipation plate 1028, thereby suppressing increase of the temperature of phosphor layer 1024. At a portion where heat transfer plate 1026 is in direct contact with phosphor layer 1024, the heat generated by phosphor layer 1024 is transferred directly, that is, not via board 1022 by heat transfer plate 1026. This also suppresses the temperature increase of phosphor layer 1024. Heat transfer plate 1026 is configured by metal having a relatively high thermal conductivity (for example, aluminum, copper or the like), or other materials having a relatively high thermal conductivity (ceramics, resin or the like). A surface of heat transfer plate 1026 which is in contact with heat dissipation plate 1028 is also referred to as a first surface, and a surface of heat transfer plate 1026 which is opposite to the first surface and in contact with board 1022 is also referred to as a second surface. Heat transfer plate 1026 is arranged so that the second surface thereof is in surface contact with the surface of board 1022 on which phosphor layer 1024 is coated, and has opening portion 1027 at a position overlapped with a portion coated with phosphor layer 1024 on the second surface.

Opening portion 1027 is an opening for passing therethrough light transmitted through or emitted from phosphor layer 1024 to the Z-direction plus side. More specifically, opening portion 1027 is arranged on an extension line of the optical path of blue light received by phosphor layer 1024, and passes therethrough white light generated from blue light received by phosphor layer 1024 and yellow light generated by the conversion of phosphor layer 1024. Opening portion 1027 corresponds to a first opening portion.

Heat dissipation plate 1028 is a heat dissipation member which is arranged in surface contact with the first surface of heat transfer plate 1026, and has opening portion 1029 at a position overlapped with opening portion 1027 of heat transfer plate 1026. Heat dissipation plate 1028 is a heat dissipation member for dissipating heat transferred from phosphor layer 1024 via heat transfer plate 1026 to the outside of luminaire 1010. The surface of heat dissipation plate 1028 may be formed in an irregular shape so that the efficiency of dissipating heat to the outside of luminaire 1010 is enhanced by increasing the surface area.

Opening portion 1029 is an opening for passing therethrough light transmitted through or emitted from phosphor layer 1024, that is, light passing through opening portion 1027 to the Z-direction plus side, thereby emitting the light to the outside of luminaire 1010. More specifically, opening portion 1029 is disposed on an extension line of the optical path, and passes therethrough white light passed through opening portion 1027 of heat transfer plate 1026 to the outside of luminaire 1010. Opening portion 1029 corresponds to a second opening portion.

Phosphor layer 1024 is configured so that the thickness thereof in the Z-direction is less than or equal to the thickness of heat transfer plate 1026 in the Z-direction. Phosphor layer 1024 may be configured so that the thickness thereof in the Z-direction is substantially equal to the thickness of heat transfer plate 1026 in the Z-direction, that is, the interface between phosphor layer 1024 and heat dissipation plate 1028 is flush with the interface between heat transfer plate 1026 and heat dissipation plate 1028. This configuration enables heat generated by phosphor layer 1024 to be transferred directly, that is, not via board 1022 and heat transfer plate 1026, to heat dissipation plate 1028, so that the transfer amount of heat can be more greatly increased.

Figure 15:
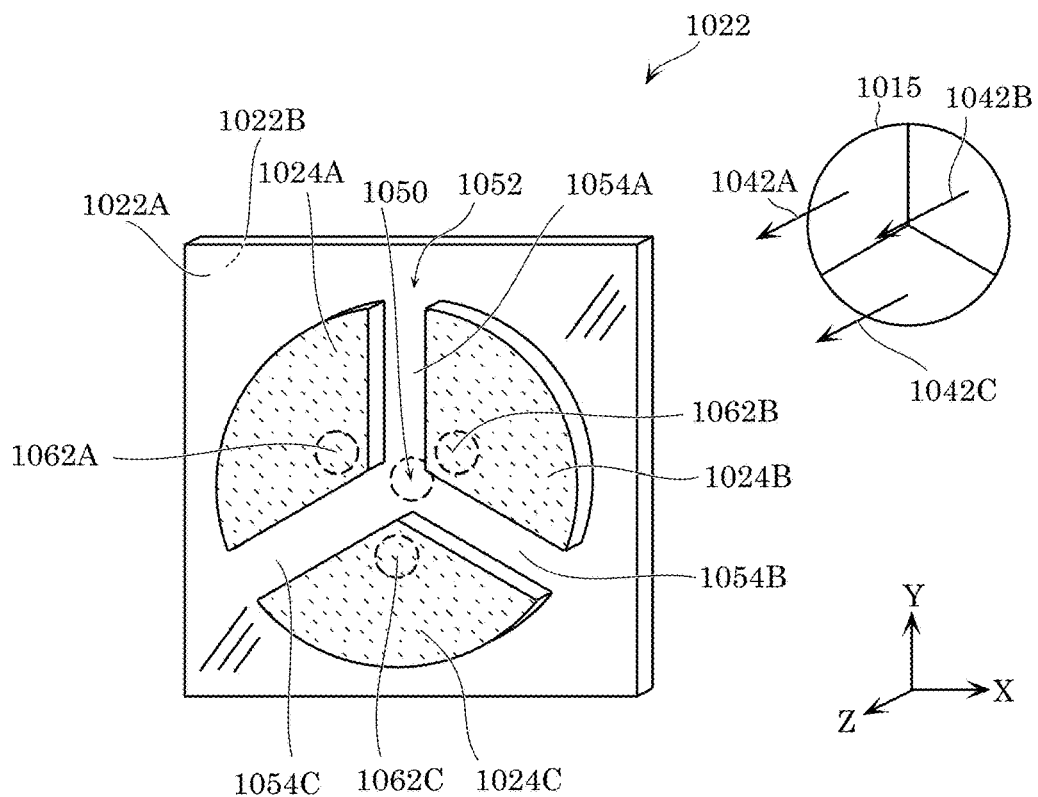
FIG. 15 is a perspective view showing a board in Embodiment 2.

FIG. 15 is a perspective view showing board 1022 in this embodiment. In FIG. 15, the first surface of board 1022 is shown as surface 1022A, and the second surface is shown as surface 1022B.

As shown in FIG. 15, board 1022 has, on surface 1022A, a portion coated with phosphor layers 1024A, 1024B, and 1024C (hereinafter also represented as phosphor layers 1024A, etc.) corresponding to phosphor layer 1024 described above. Light beams 1042A, 1042B, and 1042C (hereinafter also represented as light beams 1042A, etc.), which are obtained from the light which was introduced from optical fiber F and fiber coupling 1012 into luminaire 1010 and has passed through lens array 1015, are irradiated from the surface 1022B side to respective phosphor layers 1024A, etc. Areas to be irradiated with light beams 1042A, etc. are represented as areas 1062A, 1062B, and 1062C in FIG. 15. The portion coated with phosphor layer 1024 is formed, for example, in a substantially circular shape. Board 1022 has portions 1054A, 1054B, and 1054C uncoated with phosphor layer 1024 on lines directing from center portion 1050 of the circular shape to peripheral portion 1052 thereof.

Figure 16:
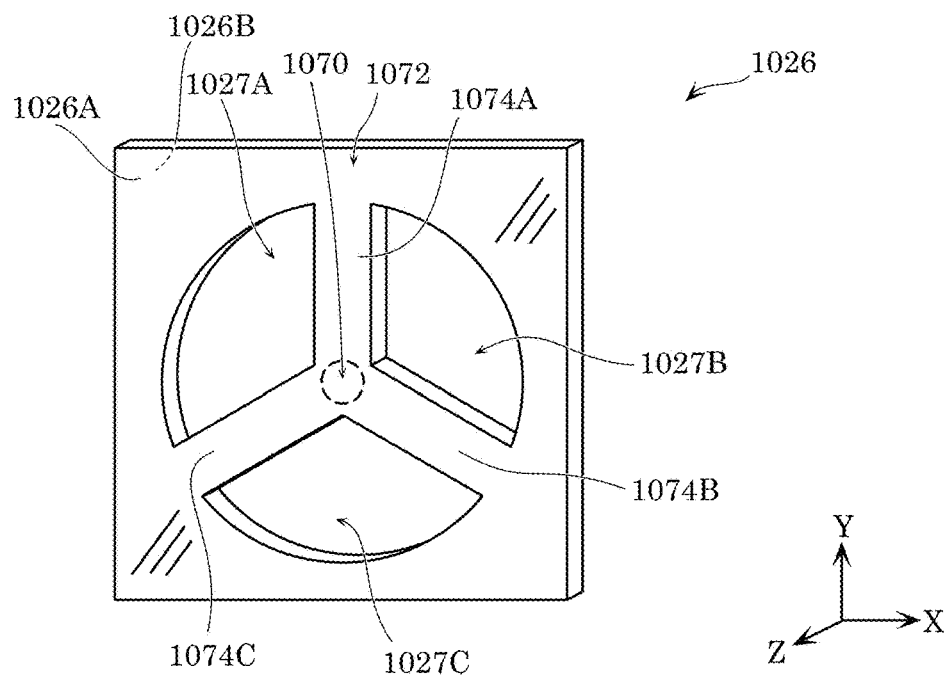
FIG. 16 is a perspective view showing a heat transfer plate in Embodiment 2.

FIG. 16 is a perspective view showing heat transfer plate 1026 in this embodiment. In FIG. 16, the first surface of heat transfer plate 1026 is shown as surface 1026A, and the second surface is shown as surface 1026B.

As shown in FIG. 16, heat transfer plate 1026 includes plural opening portions 1027A, 1027B, and 1027C (hereinafter also represented as opening portions 1027A, etc.). Opening portions 1027A, etc. have the same shapes as phosphor layers 1024A, etc. of FIG. 15. Therefore, when board 1022 and heat transfer plate 1026 are overlapped with each other, phosphor layers 1024A, etc. overlap opening portions 1027A, etc., and light transmitted through or emitted from phosphor layers 1024A, etc. in the Z-axis plus direction passes through opening portions 1027A, etc.

Opening portions 1027A, etc. are formed in a substantially circular shape, and heat transfer plate 1026 may have heat transfer bodies 1074A, 1074B, and 1074C (hereinafter also represented as heat transfer bodies 1074A, etc.) for partitioning opening portions 1027A, etc. With this configuration, heat transfer bodies 1074A, etc. transfer heat generated by phosphor layer 1024 to peripheral portion 1052 of heat transfer plate 1026, whereby the heat can be appropriately dissipated to the outside of luminaire 1010.

Furthermore, heat transfer bodies 1074, etc. may be arranged so as to extend from center portion 1070 of the circular shape to peripheral portion 1072 thereof. More specifically, heat transfer bodies 1074, etc. may be arranged so as to extend substantially linearly from center portion 1070 of the circular shape to peripheral portion 1072 thereof, that is, may be arranged radially. Since light from lens array 1015 is irradiated to a position which is relatively near to center portion 1050 of board 1022 and a heat flow path from center portion 1050 to peripheral portion 1052 is relatively long, heat generated by phosphor layer 1024 is liable to stay in the neighborhood of center portion 1050 of board 1022. Therefore, heat transfer bodies 1074, etc. arranged as described above transfer the heat generated by phosphor layer 1024 from center portion 1050 to peripheral portion 1052, so that the heat generated by phosphor layer 1024 can be appropriately dissipated to the outside of luminaire 1010.

Heat transfer bodies 1074A, etc. may be arranged at equiangular intervals around center portion 1070. This arrangement can reduce deviation of the heat flow direction from center portion 1050 of board 1022 to peripheral portion 1052 thereof, and thus reduce the temperature of phosphor layer 1024.

A result of simulation estimation for heat transmissibility inside luminaire 1010 configured as described above will be described.

Figure 17:
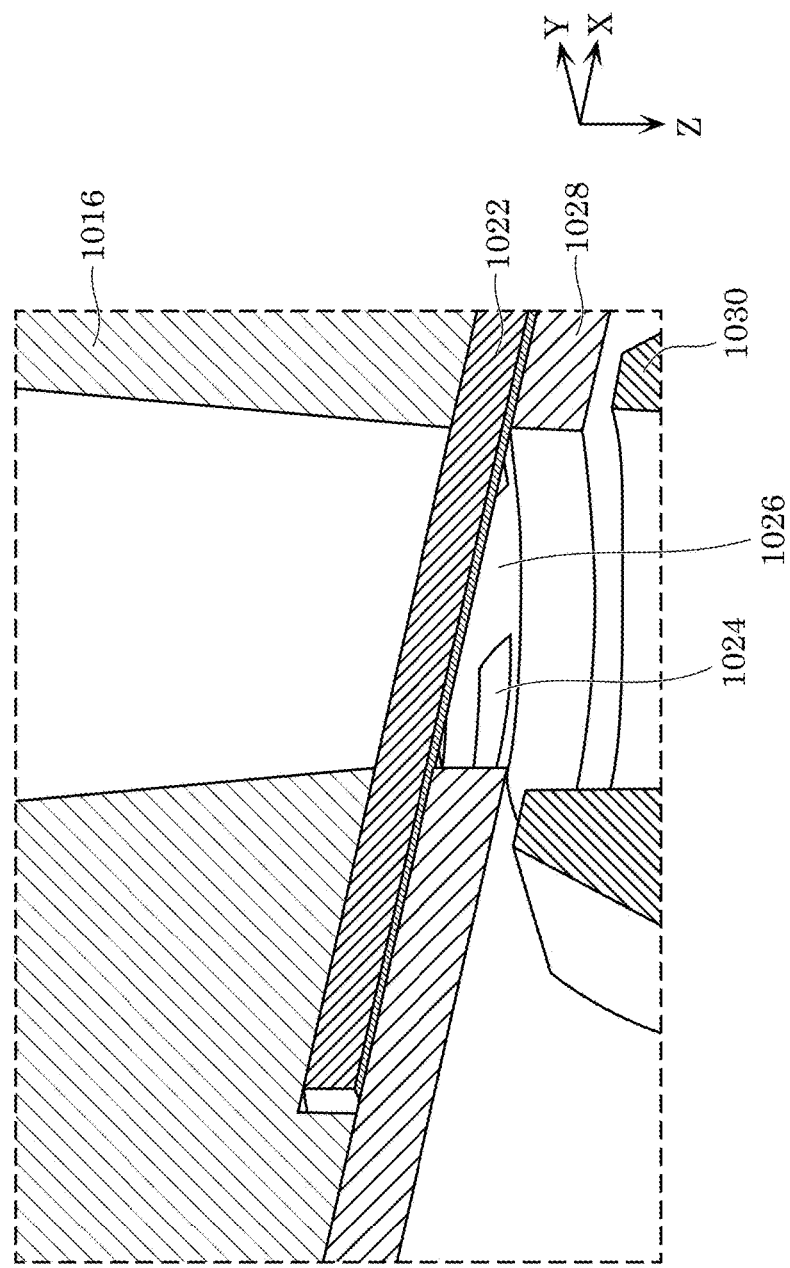
FIG. 17 is a cross-sectional view of the luminaire in Embodiment 2.

FIG. 17 is a cross-sectional view of luminaire 1010 in this embodiment. Specifically, FIG. 17 is a diagram showing a cross-section represented by VII-VII line in FIG. 11.

Holder 1016, board 1022, phosphor layer 1024, heat transfer plate 1026, heat dissipation plate 1028, and lens 1030 included in luminaire 1010 are shown in cross-sectional view of FIG. 17. A temperature distribution of each of the foregoing constituent elements on the cross-section and a temperature distribution of phosphor layer 1024 when illumination is performed by luminaire 1010 will be shown hereinafter. Furthermore, similar temperature distributions of related arts 1, 2, and 3 which are three techniques related to luminaire 1010 are shown, and description will be made while comparing these related arts and luminaire 1010. Here, related art 1 is a technique relating to a luminaire having neither heat transfer plate 1026 nor heat dissipation plate 1028 in luminaire 1010. Related art 2 is a technique relating to a luminaire which does not have heat transfer plate 1026 in luminaire 1010. Related art 3 is a technique relating to a luminaire which does not have heat dissipation plate 1028 in luminaire 1010.

Simulation estimation is performed by placing each luminaire under a temperature atmosphere of 30° C. while a light source emits light, and estimating the temperature of a phosphor layer under a steady state in which the temperature of each site of the luminaire is substantially equal to a fixed value (that is, under a state in which the temperature of each site is saturated).

Figure 18:
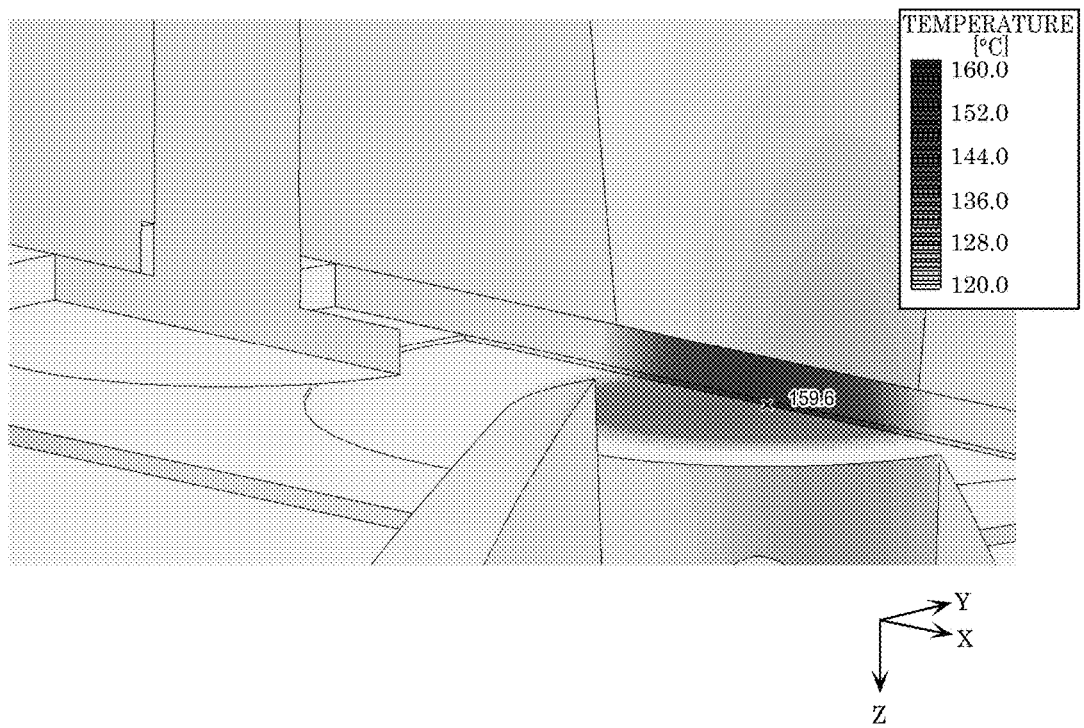
FIG. 18 is a diagram showing a temperature distribution on a cross-section of a luminaire in related art 1.
Figure 19:
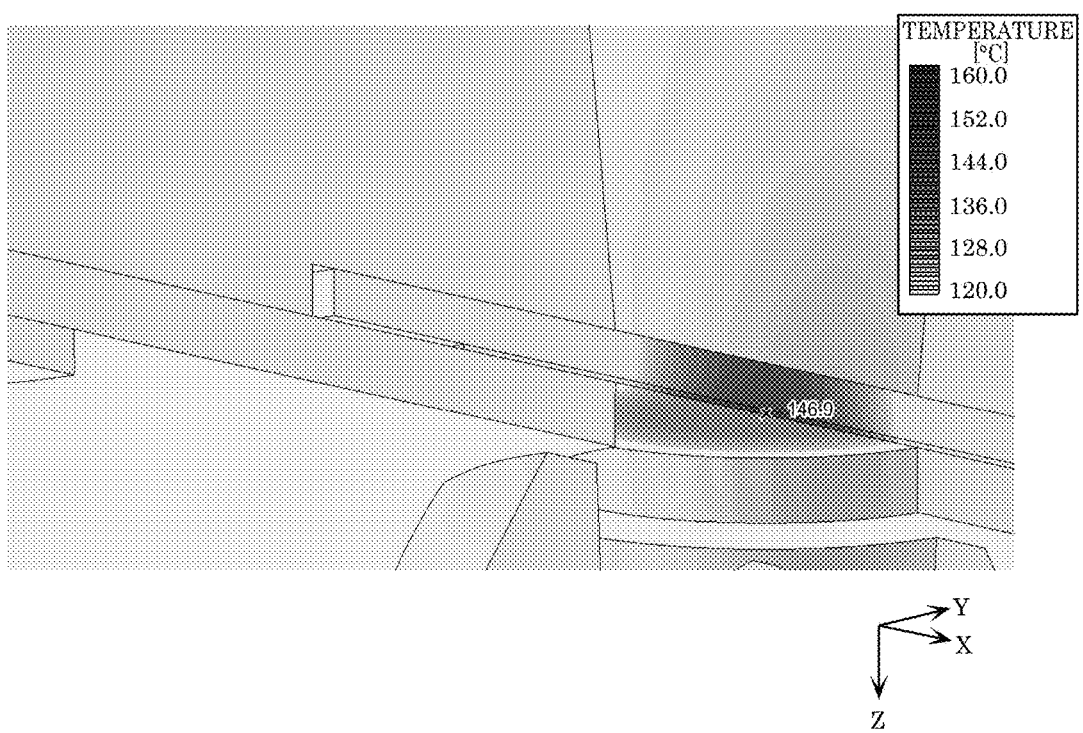
FIG. 19 is a diagram showing a temperature distribution on a cross-section of a luminaire in related art 2.
Figure 20:
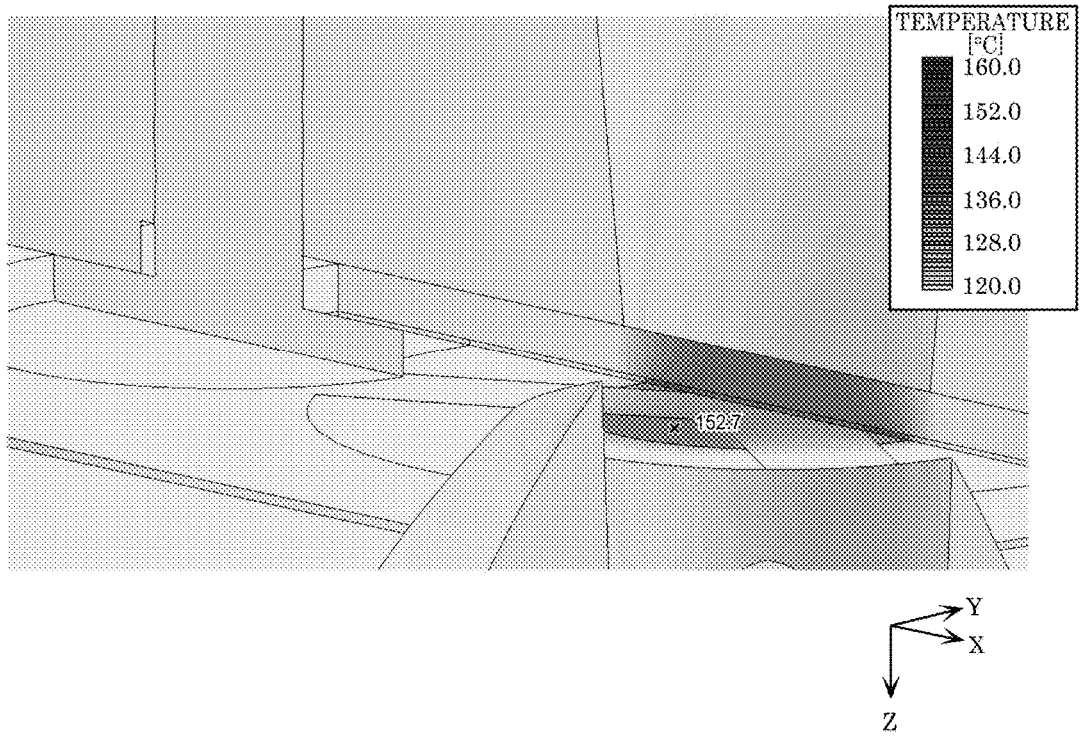
FIG. 20 is a diagram showing a temperature distribution on a cross-section of a luminaire in related art 3.
Figure 21:
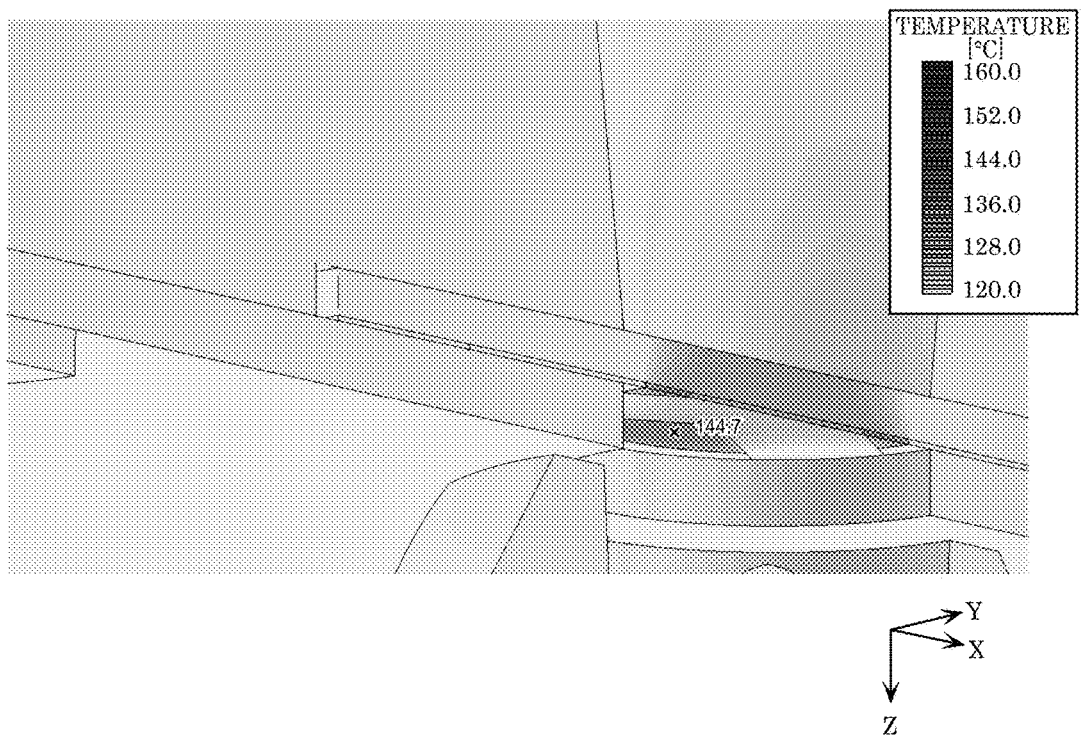
FIG. 21 is a diagram showing a temperature distribution on a cross-section of the luminaire in Embodiment 2.

FIG. 18 is a diagram showing the temperature distribution on the cross-section of the luminaire in related art 1 and the temperature distribution of the phosphor layer. FIG. 19 is a diagram showing the temperature distribution on the cross-section of the luminaire in related art 2 and the temperature distribution of the phosphor layer. FIG. 20 is a diagram showing the temperature distribution on the cross-section of the luminaire in related art 3 and the temperature distribution of the phosphor layer. FIG. 21 is a diagram showing the temperature distribution on the cross-section of luminaire 1010 and the temperature distribution of phosphor layer 1024.

As a result of the simulation estimation, the maximum values of the temperature of the phosphor layers in related arts 1, 2, and 3, and luminaire 1010 are equal to 159.6° C., 146.9° C., 152.7° C., and 144.7° C., respectively.

As described above, among the four luminaires targeted for the simulation estimation, the temperature of the phosphor layer is highest in a case where neither heat transfer plate 1026 nor heat dissipation plate 1028 is provided as in the case of related art 1, that is, an estimation result showing the lowest heat dissipation efficiency is obtained. In a case where any one of heat transfer plate 1026 and heat dissipation plate 1028 is provided (related art 2 and 3), the heat dissipation efficiency is improved to a certain degree as compared with the case of related art 1. Luminaire 1010 obtains an estimation result indicating that luminaire 1010 can efficiently dissipate heat generated from phosphor layer 1024 to the outside of luminaire 1010 by including heat transfer plate 1026 and heat dissipation plate 1028, and the temperature of the phosphor layer can be also reduced at the maximum.

A specific configuration of lens array 1015 will be described hereinafter.

Figure 22:
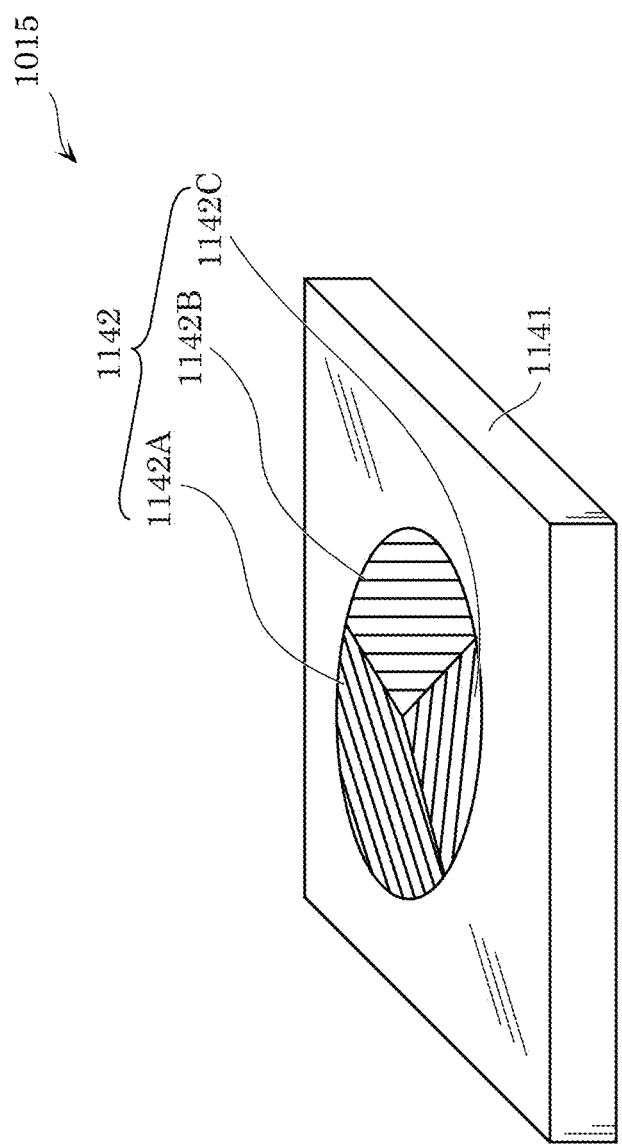
FIG. 22 is a perspective view showing a specific configuration of a lens of the luminaire in Embodiment 2.
Figure 23:
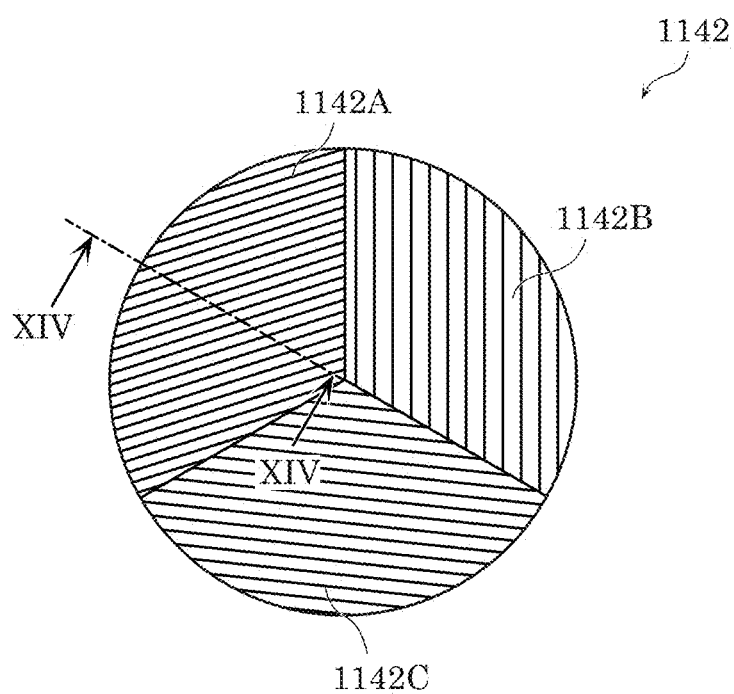
FIG. 23 is a top view showing a configuration of a diffraction type lens array in Embodiment 2.
Figure 24:
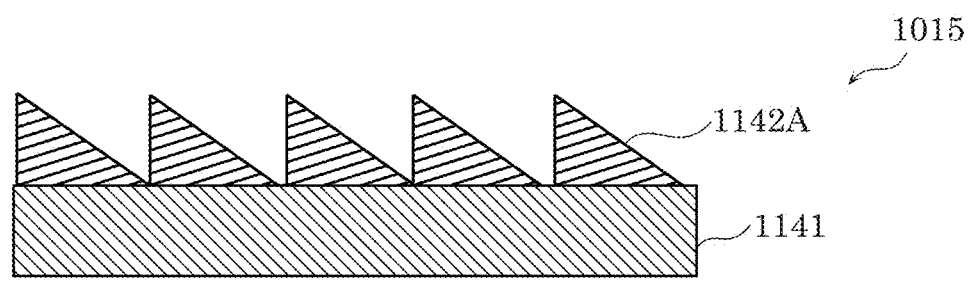
FIG. 24 is a cross-sectional view on XIV-XIV line of FIG. 23.

FIG. 22 is a perspective view showing a configuration showing lens array 1015 of luminaire 1010 in this embodiment. FIG. 23 is a top view of a configuration of diffraction type lens array 1142 of luminaire 1010 in this embodiment. FIG. 24 is a cross-sectional view on XIV-XIV line of FIG. 23.

Lens array 1015 is arranged between fiber coupling 1012 and phosphor member 1020, splits and separates light introduced from light source S via optical fiber F and fiber coupling 1012 to luminaire 1010, and emits the light to phosphor member 1020. Lens array 1015 is an example of a microlens array, for example, and includes base material 1141 and diffraction type lens array 1142 as shown in FIG. 22, for example.

Base material 1141 is the base material of the microlens array. Diffraction type lens array 1142 is formed on base material 1141. Any material such as glass or plastic may be used as a material for forming base material 1141 as in the case of board 1022.

Diffraction type lens array 1142 splits and separates light introduced into luminaire 1010, and emits the light to phosphor member 1020. The cross-sectional shape of diffraction type lens array 1142 on a plane perpendicular to the incidence face of phosphor member 1020 is a sawtooth shape. Diffraction type lens array 1142 includes plural areas where the arrangement direction of saw teeth is identical in the same area, but different among different areas.

This embodiment presents an example in which diffraction type lens array 1142 has three areas 1142A, 1142B, and 1142C (hereinafter also represented as areas 1142A, etc.) whose arrangement directions are different from one another, for example, as shown in FIG. 22 and FIG. 23. In FIG. 22 and FIG. 23, plural linearly-arranged lens arrays are provided and the arrangement directions of the plural lens arrays are identical to one another in the same area of each of three areas 1142A, etc. Here, when the wavelength of blue light from light source S is equal to, for example, 460 nm, the grating pitch of the plural lens arrays is equal to, for example, 5 μm, and the grating height is equal to 1 μm. Furthermore, the cross-sectional shape on the XIV-XIV line of FIG. 23 is a sawtooth shape as shown in FIG. 24. Here, the cross-section indicated by the XIV-XIV line corresponds to the plane perpendicular to the incidence face of phosphor member 1020 described above. The cross-sectional shape of diffraction type lens array 1142 in area 1142A is shown in FIG. 24, and those of the other areas 1142B and 1142C are likewise a sawtooth shape. That is, diffraction type lens array 1142 corresponds to a so-called blazed diffraction grating. As a result, diffraction type lens array 1142 can enhance the primary diffraction efficiency, and reduce the loss of light (optical loss).

Furthermore, in diffraction type lens array 1142, the arrangement direction of saw teeth are different among three areas 1142A, etc. as shown in FIG. 23, for example. The configuration as described above enables diffraction type lens array 1142 to prevent energy concentration on the incidence face of phosphor member 1020 even when diffraction type lens array 1142 splits and separates light introduced into luminaire 1010 and emits the light to phosphor member 1020.

The material of diffraction type lens array 1142 is selected depending on the forming method, heat resistance, and refractive index of diffraction type lens array 1142. Nanoimprint, print, photolithography, EB lithography, particle orientation, etc. are known as the method of forming diffraction type lens array 1142. When diffraction type lens array 1142 is formed, for example by nanoimprint or print, UV curing resin such as epoxy resin or acrylic resin, thermoplastic resin such as polymethyl methacrylate (PMMA) may be selected as the material of diffraction type lens array 1142. Furthermore, in consideration of heat resistance, glass or quartz may be selected as the material of diffraction type lens array 1142, and diffraction type lens array 1142 may be formed by photolithography or EB lithography. Diffraction type lens array 1142 may be formed of a material having the same level refractive index as base material 1141 to facilitate entry of light from base material 1141 to diffraction type lens array 1142. Furthermore, it is preferable that diffraction type lens array 1142 does not absorb light and is transparent as in the case of base material 1141, and also it is preferable that diffraction type lens array 1142 is formed of a material whose extinction coefficient is substantially equal to zero.

Next, the optical path of light inside luminaire 1010 when diffraction type lens array 1142 described above is used will be described.

Figure 25:
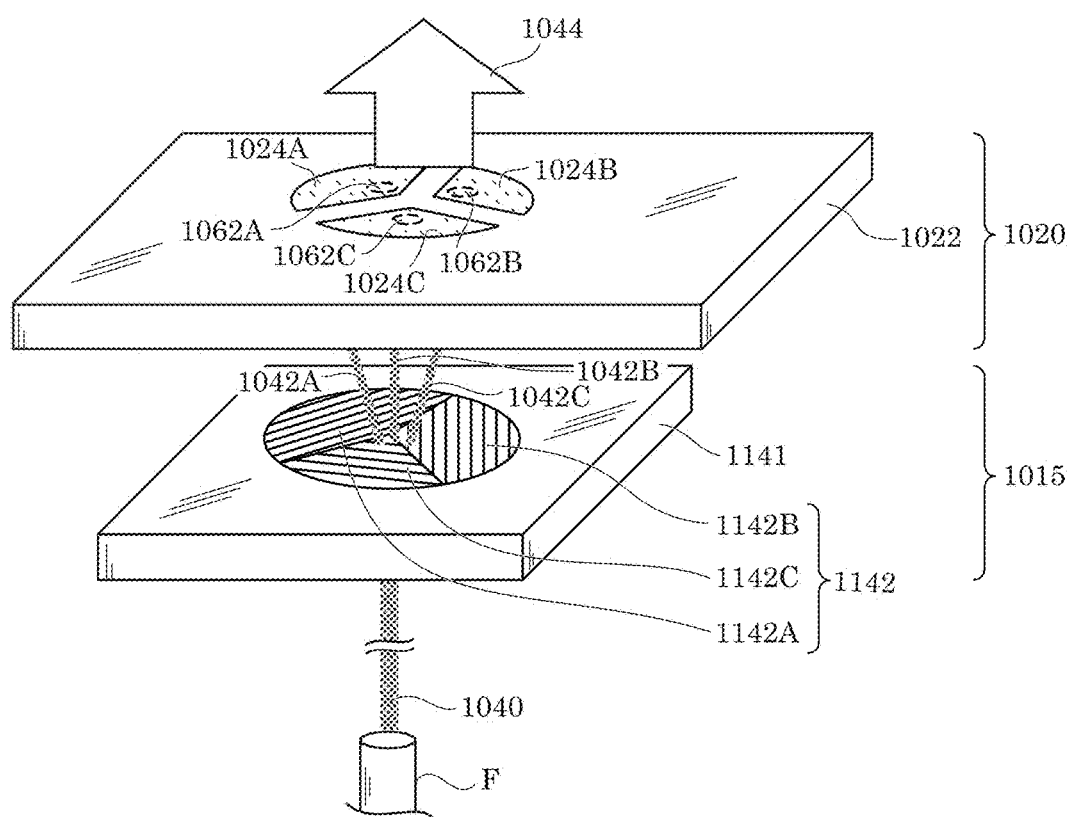
FIG. 25 is a perspective view showing optical paths of light beams passing through the diffraction type lens array in Embodiment 2.

FIG. 25 is a perspective view showing the optical path of light passing through diffraction type lens array 1142 of luminaire 1010 in this embodiment.

As shown in FIG. 25, luminaire 1010 in this embodiment splits and separates light 1040 introduced into luminaire 1010 into three light beams 1042A, 1042B, and 1042C (hereinafter also represented as light beams 1042A, etc.) by diffraction type lens array 1142, and emits the light beams to phosphor member 1020. As described above, light 1040 introduced into luminaire 1010 can be split and separated, and projected onto phosphor member 1020 without greatly changing the spot diameter of light 1040. In phosphor member 1020, split and separated light beams 1042A, etc. are respectively incident on the different areas of the incidence face, so that energy concentration on the incidence face of phosphor member 1020 can be prevented. Phosphor member 1020 can create white light 1044 by using incident light beams 1042A, etc.

Two variations of board 1022 and heat transfer plate 1026 will be described hereinafter.

Variation 1 of Embodiment 2

In this variation, a luminaire including a heat transfer plate having only one opening portion will be described. In the luminaire in this variation, the same constituent elements as those in luminaire 1010 of Embodiment 2 are represented by the same reference marks, and detailed description thereof is omitted.

The luminaire in this variation includes fiber coupling 1012, lenses 1014 and 1030, lens array 1015, holder 1016, and phosphor member 1020 as in the case of luminaire 1010. Phosphor member 1020 includes board 1082, phosphor layer 1024, heat transfer plate 1086, and heat dissipation plate 1028. The foregoing constituent elements excluding board 1082 and heat transfer plate 1086 are the same as those represented by the same terms in Embodiment 2, and detailed description thereof is omitted.

Figure 26:
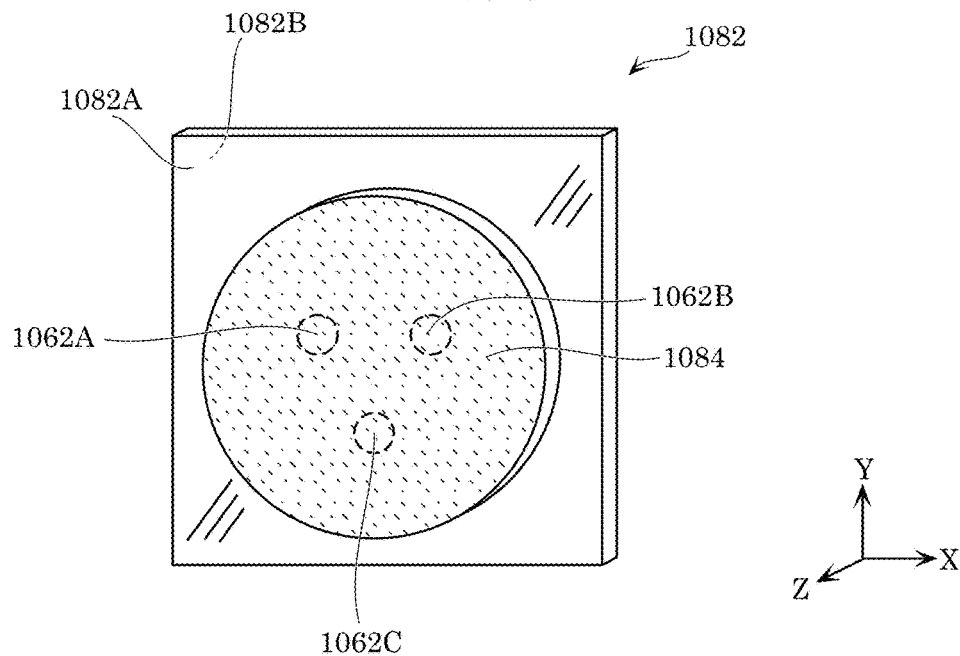
FIG. 26 is a perspective view showing a board in Variation 1 of Embodiment 2.

FIG. 26 is a perspective view showing board 1082 in this variation.

Board 1082 is a light-transmissive board which has only one portion coated with phosphor layer 1084. Light beams 1042A, 1042B, and 1042C (FIG. 15), which are obtained from the light which was introduced from optical fiber F into luminaire 1010 and has passed through lens array 1015, are irradiated from a face 1082B side to phosphor layer 1084. In FIG. 26, areas to be irradiated with the light beams are represented as areas 1062A, 1062B, and 1062C.

Figure 27:
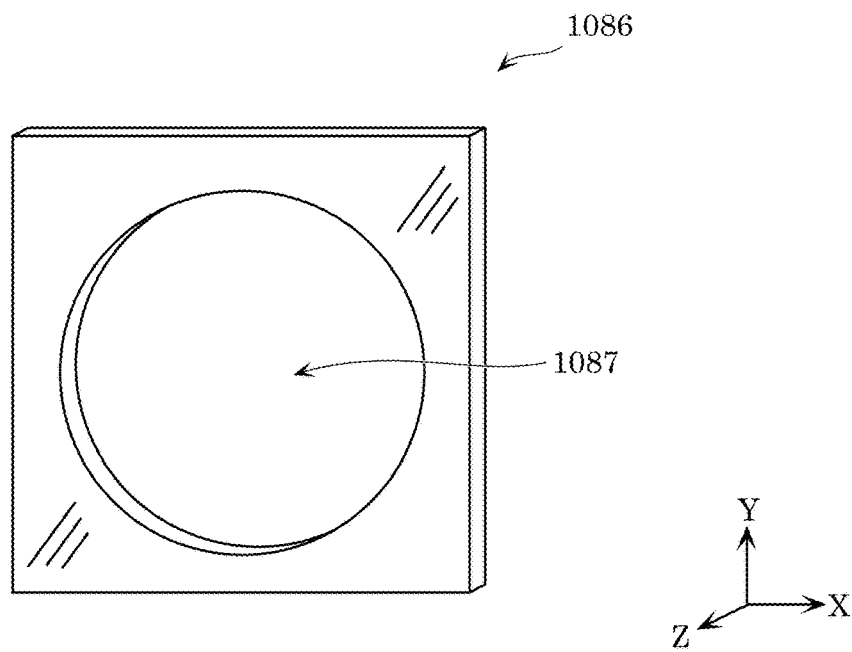
FIG. 27 is a perspective view showing a heat transfer plate in Variation 1 of Embodiment 2.

FIG. 27 is a perspective view showing heat transfer plate 1086 in this variation.

Heat transfer plate 1086 is arranged so that the second surface thereof is in surface contact with a surface of board 1082 on which phosphor layer 1084 is coated, and has one opening portion 1087 at a position overlapped with the one portion coated with phosphor layer 1084 on the second surface of heat transfer plate 1086. Opening portion 1087 is an opening for passing therethrough light transmitted through or emitted from phosphor layer 1084 to the Z-direction plus side.

The luminaire in this variation can efficiently transfer heat generated by phosphor layer 1084 to heat dissipation plate 1028 by heat transfer plate 1086. That is, the luminaire in this variation can enhance the heat dissipation efficiency by heat transfer plate 1086.

Variation 2 of Embodiment 2

In this variation, a luminaire including a heat transfer plate having two opening portions will be described. In the luminaire in this variation, the same constituent elements as those of luminaire 1010 of Embodiment 2 are represented by the same reference marks, and detailed description thereof is omitted.

As in the case of luminaire 1010, the luminaire in this variation includes fiber coupling 1012, lenses 1014 and 1030, lens array 1015, holder 1016, and phosphor member 1020. Phosphor member 1020 includes board 1092, phosphor layer 1024, heat transfer plate 1096, and heat dissipation plate 1028. The foregoing constituent elements excluding board 1092 and heat transfer plate 1096 are the same as those represented by the same terms in Embodiment 2, and detailed description thereof is omitted.

Figure 28:
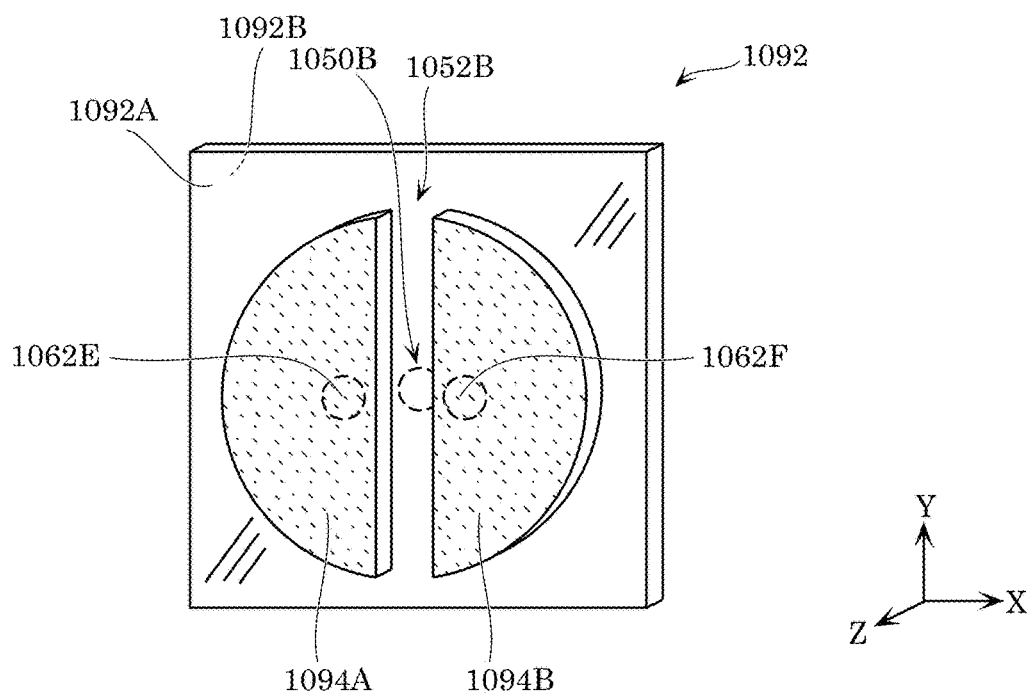
FIG. 28 is a perspective view showing a board in Variation 2 of Embodiment 2.

FIG. 28 is a perspective view showing board 1092 in this variation.

Board 1092 is a light-transmissive board which has portions coated with phosphor layers 1094A and 1094B. Light which is introduced from optical fiber F into luminaire 1010 and passes through lens array 1015 is irradiated from a surface 1092B side to each of phosphor layers 1094A and 1094B. In FIG. 28, the areas to be irradiated with this light are represented as areas 1062E and 1062F.

Figure 29:
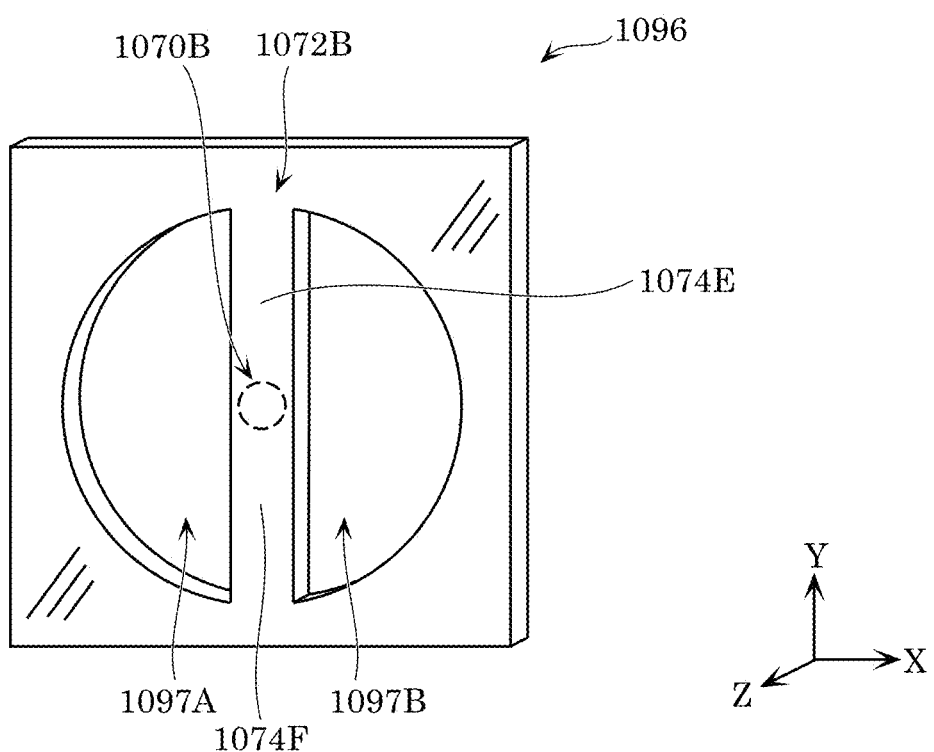
FIG. 29 is a perspective view showing a heat transfer plate in Variation 2 of Embodiment 2.

FIG. 29 is a perspective view showing heat transfer plate 1096 in this variation.

Heat transfer plate 1096 is arranged so that the second surface thereof is in surface contact with a surface of board 1092 on which phosphor layers 1094A and 1094B are coated, and has two opening portions 1097A and 1097B at positions overlapped with the portions coated with phosphor layers 1094A and 1094B on the second surface. Opening portions 1097A and 1097B are openings through which light transmitted through or emitted from phosphor layers 1094A and 1094B is passed to the Z-direction plus side.

The luminaire in this variation can efficiently transfer heat generated by phosphor layers 1094A and 1094B to heat dissipation plate 1028 by heat transfer plate 1096. That is, the luminaire in this variation can enhance the heat dissipation efficiency by heat transfer plate 1096.

As described above, luminaire 1010 in this embodiment includes board 1022 having light-transmissivity and including one or more portions provided with phosphor layer 1024, heat transfer plate 1026 which is arranged in surface contact with board 1022 and has one or more opening portions 1027 located at positions which are respectively overlapped with the one or more portions, and heat dissipation plate 1028 which is arranged in surface contact with surface 1026A on the opposite side to surface 1026B of heat transfer plate 1026 which is in surface contact with board 1022, and has opening portion 1029 at a position overlapped with one or more opening portions 1027 of heat transfer plate 1026.

According to this configuration, heat generated when phosphor layer 1024 converts the wavelength of light is transferred through board 1022 or directly to heat transfer plate 1026, and heat transfer plate 1026 further transfers the heat to heat dissipation plate 1028. As described above, increase of the temperature of phosphor layer 1024 can be suppressed by existence of heat transfer plate 1026. Accordingly, luminaire 1010 can enhance the heat dissipation efficiency while preventing increase of the size of the luminaire.

For example, board 1022 may have plural portions as one or more portions, and heat transfer plate 1026 may have plural opening portions 1027 as one or more opening portions 1027, the plural opening portions being arranged at positions which are respectively overlapped with the plural portions.

According to this configuration, even when phosphor layers 1024 are arranged at plural places of board 1022, heat transfer plate 1026 transfers heat generated by phosphor layers 1024 to heat dissipation plate 1028. Therefore, luminaire 1010 can enhance the heat dissipation efficiency while preventing increase of the size of the luminaire.

For example, heat transfer plate 1026 may include heat transfer bodies 1074A, 1074B, and 1074C which are arranged to extend from center portion 1070 of heat transfer plate 1026 to peripheral portion 1072.

According to this configuration, heat transfer plate 1026 transfers heat generated by phosphor layer 1024 from center portion 1070 of heat transfer plate 1026 to peripheral portion 1072 thereof by heat transfer bodies, and also transfers the heat to heat dissipation plate 1028. As a result, increase of the temperature of center portion 1050 of phosphor layer 1024 on which heat generated by phosphor layer 1024 is liable to concentrate can be prevented.

For example, heat transfer bodies 1074A, 1074B, and 1074C may be arranged at equiangular intervals around center portion 1070.

According to this configuration, heat transfer bodies 1074A, 1074B, and 1074C can uniformly transfer heat from center portion 1070 of heat transfer plate 1026 to peripheral portion 1072 thereof without deviation in direction. As a result, the temperature increase of phosphor layer 1024 can be prevented equally without deviation in direction when viewed from center portion 1070 of heat transfer plate 1026.

For example, phosphor layer 1024 may be formed so that the interface between phosphor layer 1024 and heat dissipation plate 1028 and the interface between heat transfer plate 1026 and heat dissipation plate 1028 may be flush with each other.

According to this configuration, heat generated by phosphor layer 1024 can be directly, that is, via neither board 1022 nor heat transfer plate 1026 to heat dissipation plate 1028, and the transfer amount of heat can be more increased. As a result, the temperature increase of phosphor layer 1024 can be further prevented.

For example, phosphor layer 1024 may receive incident blue light, convert a part of the received blue light to yellow light, one or more opening portions 1027 of heat transfer plate 1026 may be arranged on an extension line of the optical path of the blue light received by phosphor layer 1024, and pass therethrough white light generated from the blue light received by phosphor layer 1024 and the yellow light generated by the conversion of phosphor layer 1024, and opening portion 1029 of heat dissipation plate 1028 may be arranged on an extension line of the optical path and pass the white light passed by one or more opening portions 1027 of heat transfer plate 1026 to the outside of luminaire 1010.

According to this configuration, luminaire 1010 can emit white light by using incident blue light to the outside, and also prevent the temperature increase of phosphor layer 1024.

Luminaire 1010 in this embodiment includes luminaire 1010 described above, light source S, and optical fiber F for leading light emitted from light source S to luminaire 1010, and phosphor layer 1024 provided to board 1022 of luminaire 1010 receives light led by optical fiber F.

According to this configuration, lighting apparatus 1001 has the same effect as luminaire 1010.

(Others)

The luminaire according to the present invention is described based on Embodiment 2. However, the present invention is not limited to Embodiment 2.

In addition, the present invention contains configurations obtained by making various modifications perceived by a person skilled in the art on Embodiment 2, and configurations realized by freely combining the constituent elements and functions in Embodiment 2 without departing from the subject matter of the present invention.

Embodiment 3

In this embodiment, a luminaire and a lighting apparatus that can enhance the heat dissipation efficiency while preventing increase of the size will be described. The same constituent elements are represented by the same reference marks, and description thereof may be omitted. In the following description, description may be made by using the XYZ coordinate axes shown in each figure.

Figure 30:
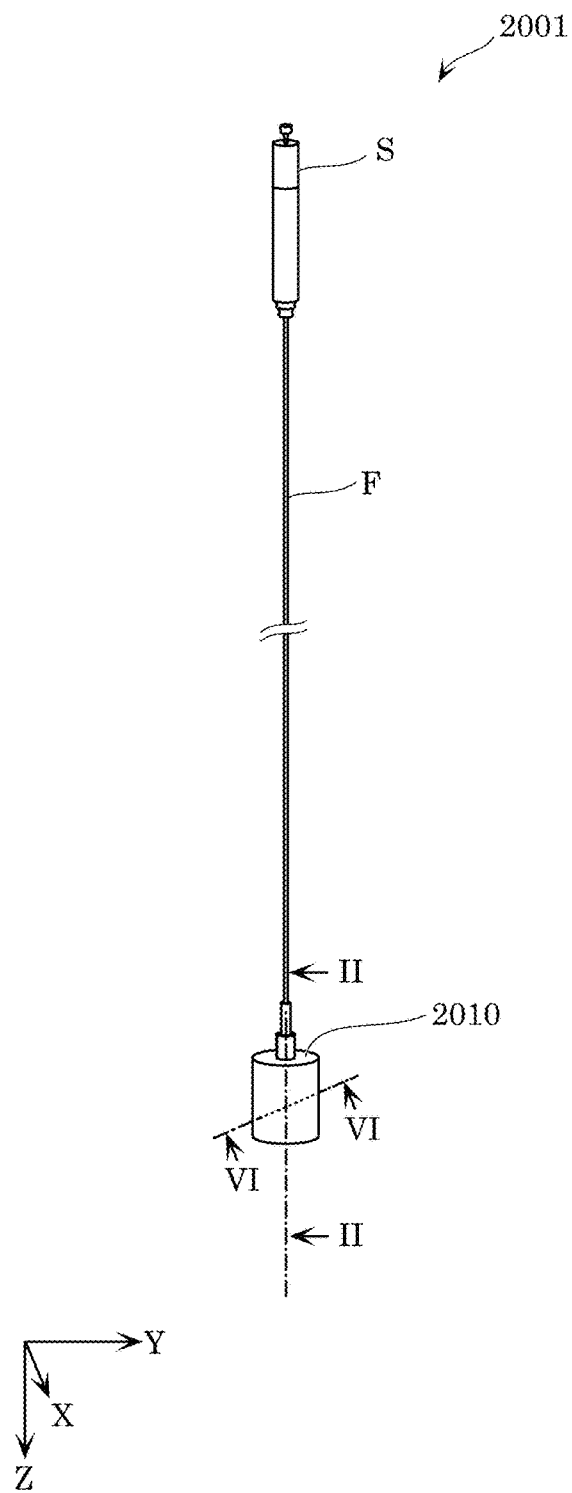
FIG. 30 is an external view of a lighting apparatus in Embodiment 3.

FIG. 30 is an external view of lighting apparatus 2001 according to this embodiment.

As shown in FIG. 30, lighting apparatus 2001 includes light source S, optical fiber F, and luminaire 2010.

Light source S is a light source for emitting light, and is, for example, a laser diode (LD) or a light emitting diode (LED). More specifically, light source S is an LD or an LED for emitting blue light, but the color of light emitted from light source S is not limited to the above color.

Optical fiber F is configured in a dual structure in which a core having a high refractive index is wrapped by a cladding layer having a low refractive index. Optical fiber F functions as a transmission path of light for leading light emitted from light source S to luminaire 2010. The core and cladding layer of optical fiber F are formed of quart glass or plastic which has very high transmissivity to light.

Luminaire 2010 is a luminaire for emitting light transmitted from light source S via optical fiber F to the outside of luminaire 2010 to illuminate the surroundings of luminaire 2010. Luminaire 2010 has a phosphor layer for converting the color (wavelength) of the whole or a part of light received from optical fiber F. For example, the phosphor layer is formed by sealing a yellow phosphor for converting blue light to yellow light with resin or the like. In this case, luminaire 2010 converts a part of blue light transmitted from light source S to yellow light by the yellow phosphor to generate white light, and emits the white light to the surroundings of luminaire 2010.

The configuration of luminaire 2010 will be described hereinafter in detail.

Figure 31:
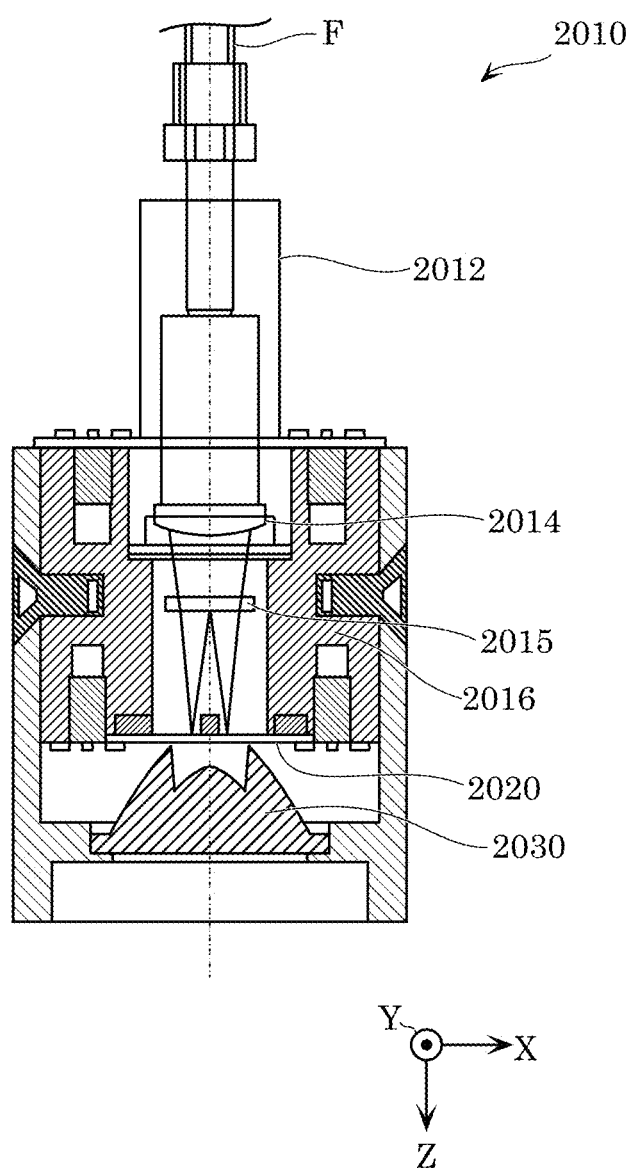
FIG. 31 is a cross-sectional view showing an internal configuration of a luminaire included in the lighting apparatus in Embodiment 3.

FIG. 31 is a cross-sectional view showing an internal configuration of luminaire 2010 contained in lighting apparatus 2001 according to this embodiment. FIG. 31 is a diagram showing a cross-section indicated by II-II line in FIG. 30 of luminaire 2010.

As shown in FIG. 31, luminaire 2010 includes fiber coupling 2012, lenses 2014 and 2030, lens array 2015, holder 2016, and phosphor member 2020.

Fiber coupling 2012 is an optical member which is connected to optical fiber F, and leads light transmitted from light source S via optical fiber F in the Z-axis plus direction into luminaire 2010.

Lens 2014 is an optical member for changing the optical path of light introduced via fiber coupling 2012. The material for forming lens 2014 is a light-transmissive material such as glass or plastic, for example.

Lens array 2015 is an optical member for changing the optical path of light emitted from lens 2014. Specifically, lens array 2015 changes (separates) the optical path of introduced light so that the light is split into plural (for example, two) light beams traveling along the respective optical paths thereof to phosphor member 2020. A specific configuration of lens array 2015 will be described by presenting a specific example later. Lens array 2015 may be arranged at any position between fiber coupling 2012 and phosphor member 2020. Particularly, lens array 2015 may be arranged in contact with lens 2014, or may be formed as a part of lens 2014 (that is, molded integrally with lens 2014). The material for forming lens array 2015 is a light-transmissive material such as glass or plastic, for example.

Holder 2016 is a housing for accommodating respective constituent elements of luminaire 2010 therein. The material for forming holder 2016 is a material having relatively high thermal conductivity such as aluminum or copper, for example.

Phosphor member 2020 is a member containing a phosphor for receiving light passing through lens array 2015, converting the color of the received light and emitting the converted light. In addition to the phosphor, phosphor member 2020 has a heat transfer plate and a heat dissipation plate as a heat dissipation mechanism for dissipating heat generated by the phosphor to the outside of luminaire 2010. The configurations of these elements will be described in detail later.

Lens 2030 is an optical member for adjusting the light distribution characteristic when light emitted from phosphor member 2020 is emitted to the outside of luminaire 2010 (in the Z-axis plus direction). Lens 2030 sets the light distribution characteristic to narrow-angle light distribution or wide-angle light distribution based on the shape of lens 2030. A lens having an appropriate light distribution characteristic may be adopted as lens 2030 according to intended use of luminaire 2010. The material for forming lens 2030 is the same as the material for lens 2014.

The detailed configurations of phosphor member 2020, etc. of luminaire 2010 will be described hereinafter.

Figure 32:
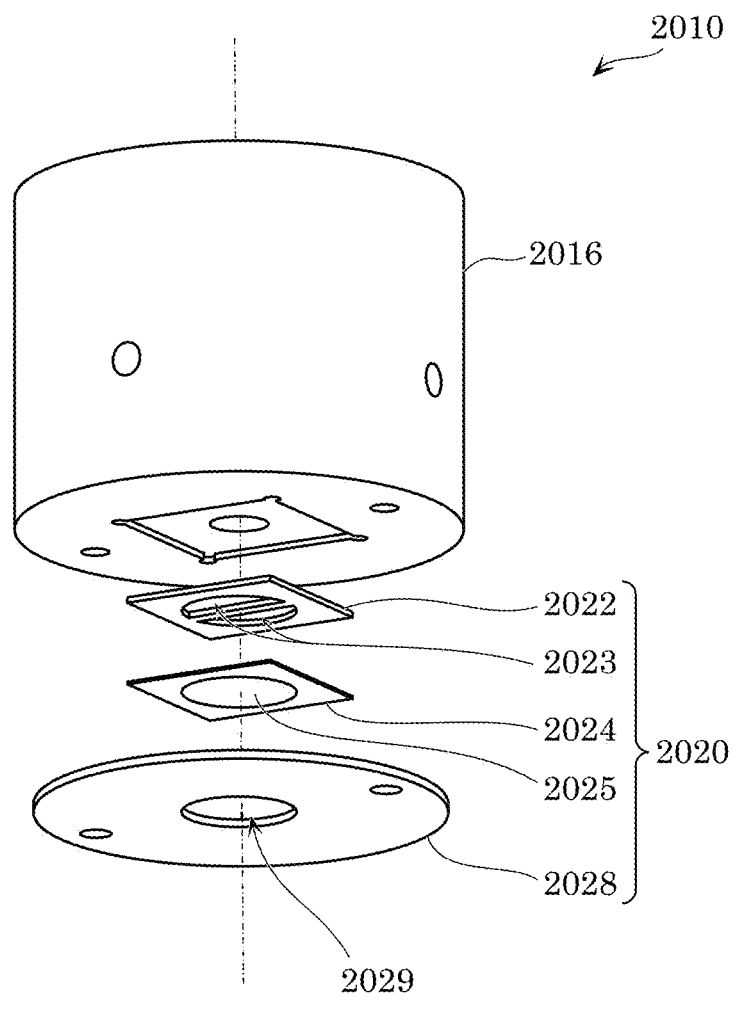
FIG. 32 is an exploded perspective view of a holder and a phosphor member included in a luminaire in Embodiment 3.
Figure 33:
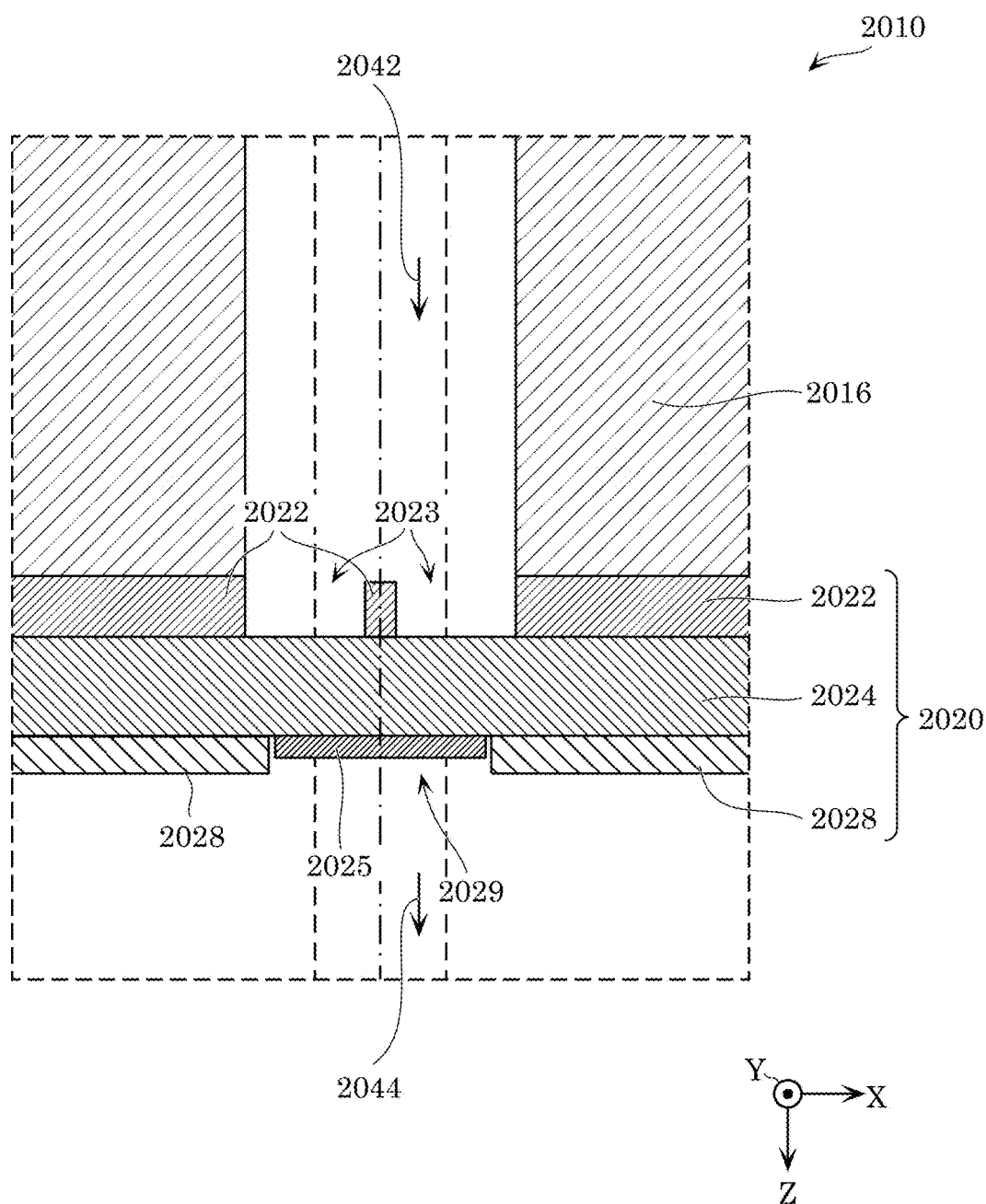
FIG. 33 is a cross-sectional view of the holder and the phosphor member included in the luminaire in Embodiment 3.

FIG. 32 is an exploded perspective view of holder 2016 and phosphor member 2020 included in luminaire 2010 in this embodiment. FIG. 33 is a cross-sectional view of holder 2016 and phosphor member 2020 included in luminaire 2010 in this embodiment. The cross-sectional view of FIG. 33 is an enlarged view in which the neighborhood of holder 2016 and phosphor member 2020 in cross-sectional view shown in FIG. 31 is enlarged.

As shown in FIG. 32 and FIG. 33, phosphor member 2020 includes heat transfer plate 2022, board 2024, phosphor layer 2025, and heat dissipation plate 2028.

Heat transfer plate 2022 is a plate-shaped heat transfer body for transferring (dissipating) heat generated by phosphor layer 2025 to the air with which holder 2016 and heat transfer plate 2022 are in contact. Heat transfer plate 2022 is arranged in surface contact with each of holder 2016 and board 2024 between holder 2016 and board 2024. Heat generated by phosphor layer 2025 is transferred to heat transfer plate 2022 via board 2024, and heat transfer plate 2022 transfers the transferred heat to holder 2016, thereby suppressing the temperature increase of phosphor layer 2025. Heat transfer plate 2022 is formed of metal having relatively high thermal conductivity (for example, aluminum, copper or the like), or other materials having relatively high heat conductivity (ceramics, resin or the like). A surface of heat transfer plate 2022 which is in contact with board 2024 is also referred to as a first surface, and a surface of heat transfer plate 2022 which is opposite to the first surface and in contact with holder 2016 is also referred to as a second surface.

Heat transfer plate 2022 may be formed by processing a part of holder 2016. That is, heat transfer plate 2022 may be molded integrally with holder 2016 or integrated with holder 2016. When heat transfer plate 2022 and holder 2016 are arranged in surface contact with each other as described above, an air layer of several µm is formed between heat transfer plate 2022 and holder 2016, and this air layer may disturb heat transfer from heat transfer plate 2022 to holder 2016. Therefore, integral molding of heat transfer plate 2022 and holder 2016 can prevent occurrence of the air layer of several µm, and avoid disturbance of heat transfer from heat transfer plate 2022 to holder 2016. Furthermore, there is an advantage that the manufacturing cost can be reduced by eliminating some members constituting luminaire 2010.

Heat transfer plate 2022 has opening portion 2023. Opening portion 2023 is an opening for passing therethrough light emitted from lens array 2015 to the Z-axis plus side. That is, light emitted from lens array 2015 passes through opening portion 2023 and reaches phosphor layer 2025. Opening portion 2023 is arranged on the optical path of blue light emitted from lens array 2015. In other words, heat transfer plate 2022 is positioned so that the optical path of the blue light passes through opening portion 2023. Opening portion 2023 corresponds to a first opening portion.

Board 2024 is a light-transmissive board. Board 2024 is irradiated with light which is emitted from lens array 2015 and passes through opening portion 2023. Board 2024 has a portion which is provided with phosphor layer 2025 for converting the color of the received light. A case where phosphor layer 2025 is provided on board 2024 by coating phosphor layer 2025 on board 2024 will be described as an example, but the present invention is not limited to the foregoing method of providing phosphor layer 2025 on board 2024. In the following description, a surface having a portion coated with phosphor layer 2025 is also referred to as a first surface, and a surface on the opposite side to the first surface is also referred to as a second surface. Furthermore, a case where light from optical fiber F is irradiated from the second surface side will be described as an example.

Any material such as glass or plastic may be used as the material for forming board 2024. Here, as the glass, soda glass, non-alkali glass, sapphire glass or the like may be used, for example. Furthermore, as the plastic, acrylic resin, polycarbonate, polyethylene terephthalate (PET), polyethylenenaphthalate (PEN) or the like may be used, for example. When board 2024 is formed of a material which does not absorb light and is transparent, in other words, a material having an extinction coefficient of substantially zero, there is an advantage that the amount of light passing through board 2024 can be increased, so that the amount of light emitted from luminaire 2010 to the surroundings thereof can be increased.

Phosphor layer 2025 is a wavelength conversion member for receiving light introduced from light source S via optical fiber F and converting the color (wavelength) of the received light by phosphor particles. Phosphor layer 2025 generates heat when converting the color of light.

Specifically, phosphor layer 2025 contains yellow phosphor particles for receiving blue light from light source S and emitting yellow light, for example, yttrium-aluminum-garnet (YAG)-based phosphor particles, and is formed by sealing these phosphor particles with resin such as silicon or epoxy. Phosphor layer 2025 generates white light by color-mixing of yellow light to which a part of blue light emitted from light source S is converted by the phosphor particles, and the remaining part of the blue light, and emits the white light in the Z-axis plus direction. When phosphor layer 2025 is left under high-temperature atmosphere, the light color conversion efficiency thereof generally decreases (deteriorates). Therefore, luminaire 2010 appropriately dissipates heat generated from phosphor layer 2025 to the outside of luminaire 2010 by heat transfer plate 2022 as a heat dissipation mechanism, thereby suppressing increase of the temperature of phosphor layer 2025. The heat dissipation performance may be enhanced by mixing the resin for forming phosphor layer 2025 with a material having a high thermal conductivity, for example, inorganic oxide such as ZnO.

Heat dissipation plate 2028 is a heat dissipation member which is arranged in surface contact with the first surface of board 2024, and has opening portion 2029 at a position overlapping with a portion provided with phosphor layer 2025 on board 2024. Heat dissipation plate 2028 dissipates heat transferred from phosphor layer 2025 to the outside of luminaire 2010. The surface of heat dissipation plate 2028 may be formed in an irregular shape. This is because the efficiency of dissipating heat to the outside of luminaire 2010 can be enhanced by increasing the surface area of heat dissipation plate 2028.

Opening portion 2029 is an opening for passing therethrough light transmitted via or emitted from phosphor layer 2025 to the Z-axis plus side to emit the light to the outside of luminaire 2010. Opening portion 2029 is an example of a second opening portion.

Figure 34:
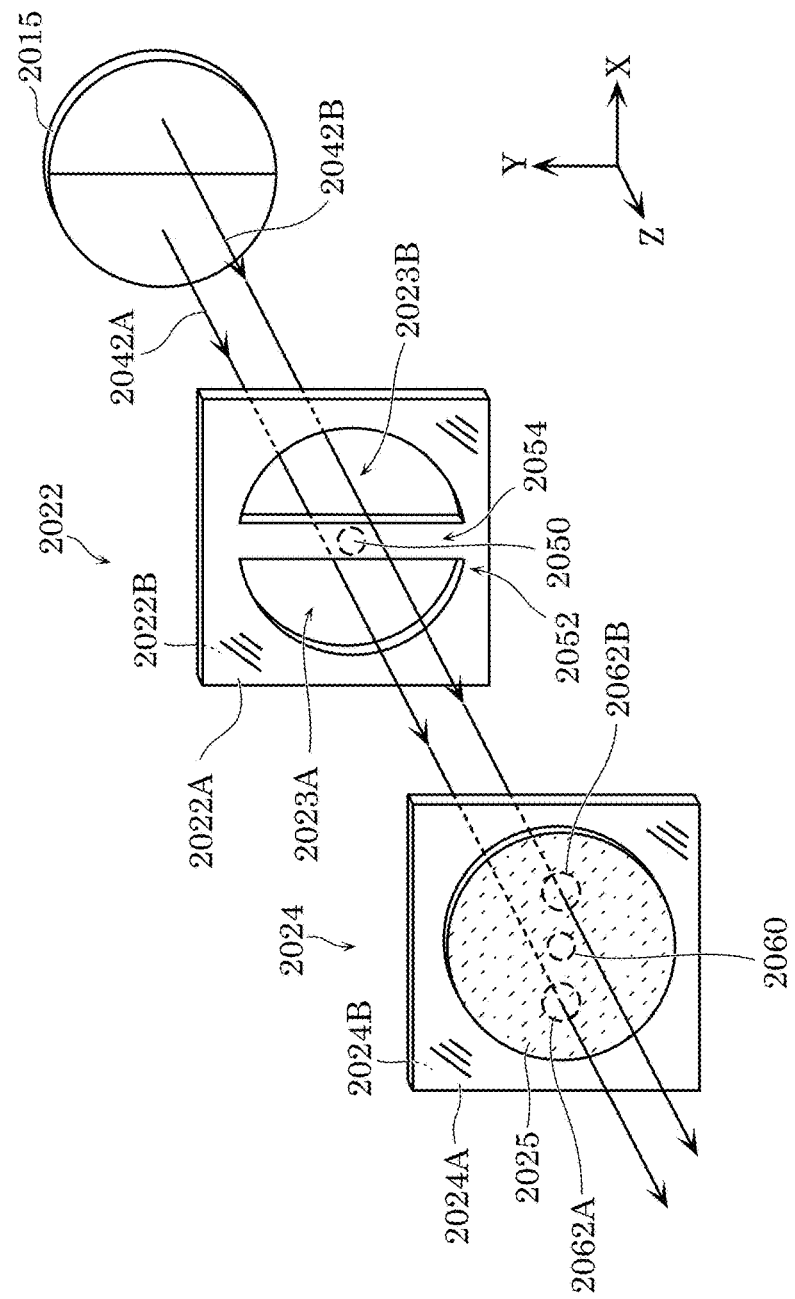
FIG. 34 is a schematic diagram showing specific shapes of a heat transfer plate and a board, and optical paths of light beams in Embodiment 3.

FIG. 34 is a schematic diagram showing specific shapes of heat transfer plate 2022 and board 2024 and the optical path of light in this embodiment. In FIG. 34, heat transfer plate 2022 and board 2024 are illustrated in exploded view for description. However, heat transfer plate 2022 and board 2024 are arranged actually in contact with each other. In FIG. 34, the first surface of heat transfer plate 2022 is shown as surface 2022A, and the second surface is shown as surface 2022B. Furthermore, the first surface of board 2024 is shown as surface 2024A, and the second surface is shown as surface 2024B.

As shown in FIG. 34, heat transfer plate 2022 includes plural opening portions 2023A and 2023B (hereinafter also represented as opening portions 2023A, etc.). Each of opening portions 2023A, etc. has a substantially semicircular shape, and light beams 2042A and 2042B (hereinafter also represented as light beams 2042A, etc.) emitted from lens array 2015 and travelling in the Z-axis plus direction pass through opening portions 2023A, etc. Heat transfer plate 2022 has heat transfer body 2054 extending from center portion 2050 of heat transfer plate 2022 to peripheral portion 2052 thereof. Heat transfer body 2054 has a rod-like shape, for example. It may be said that opening portions 2023A, etc. are partitioned by heat transfer body 2054.

Board 2024 has a portion coated with phosphor layer 2025 on surface 2024A. Phosphor layer 2025 is irradiated, from the surface 2024B side, with light beams 2042A, etc. emitted from lens array 2015 and passing through opening portions 2023A, etc. Areas to be irradiated with light beams 2042A, etc. are shown as areas 2062A and 2062B in FIG. 34. The portion coated with phosphor layer 2025 is formed in a substantially circular shape, for example. A portion non-irradiated with light beams 2042A, etc. (that is, a portion overlapped with heat transfer body 2054) out of the portion coated with phosphor layer 2025 may be uncoated with phosphor layer 2025. This is because this portion is not irradiated with light beams 2042A, etc., and thus the phosphor contained in this portion out of phosphor layer 2025 does not perform wavelength conversion.

When phosphor layer 2025 is irradiated with light beams 2042A, etc., phosphor layer 2025 converts the color of parts of the irradiated light beams and generates heat. Therefore, the temperature around center portion 2060 of board 2024 would become higher than that of the surroundings without any heat dissipation mechanism, so that phosphor layer 2025 could deteriorate.

Accordingly, heat around center portion 2060 is transferred to peripheral portion 2052 of heat transfer plate 2022 by heat transfer body 2054 arranged in contact with center portion 2060 of board 2024, thereby suppressing increase of the temperature of center portion 2060 and deterioration of phosphor layer 2025.

Heat transfer body 2054 may have any other shape insofar as heat transfer body 2054 is shaped to extend from center portion 2050 of heat transfer plate 2022 to peripheral portion 2052 thereof. More specifically, heat transfer body 2054 may be arranged so as to extend substantially linearly from center portion 2050 to plural places of peripheral portion 2052, that is, may be arranged radially. This configuration enables increase of the amount of heat to be transferred from center portion 2050 of heat transfer plate 2022 to peripheral portion 2052 thereof.

Furthermore, heat transfer body 2054 may be arranged at equiangular intervals around center portion 2050. This configuration enables reduction of deviation in heat flow direction from center portion 2050 of heat transfer plate 2022 to peripheral portion 2052 thereof, and also reduction of the temperature of phosphor layer 2025 without deviation.

Heat transfer body 2054 may have any shape insofar as heat transfer body 2054 is located at a position different from the optical path of light emitted from lens array 2015, that is, arranged at a position where the light is not blocked off. Furthermore, a part of the light may be blocked off. When a part of the light is blocked off, the amount of light emitted to the outside by luminaire 2010 is consequently reduced, but the same effect of suppressing the temperature increase of phosphor layer 2025 and preventing deterioration as described above is exhibited.

A result of simulation estimation for heat transfer performance inside luminaire 2010 configured as described above will be described.

Figure 35:
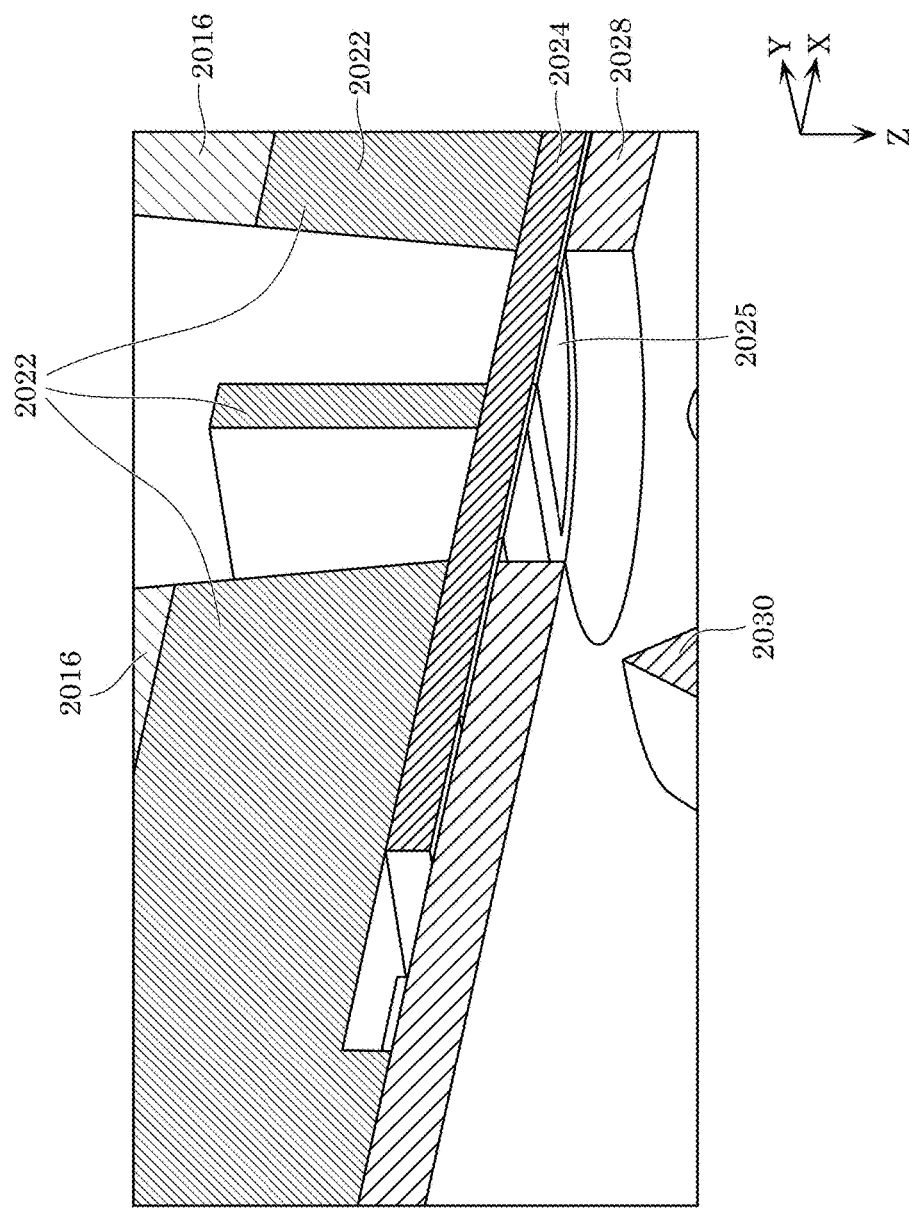
FIG. 35 is a cross-sectional view of the luminaire in Embodiment 3.

FIG. 35 is a cross-sectional view of luminaire 2010 in this embodiment. Specifically, FIG. 35 is a diagram showing a cross-section indicated by VI-VI line in FIG. 30 of luminaire 2010.

Holder 2016, heat transfer plate 2022, board 2024, phosphor layer 2025, heat dissipation plate 2028, and lens 2030 included in luminaire 2010 are shown in cross-sectional view shown in FIG. 35. A temperature distribution of each of the foregoing constituent elements on the cross-section and a temperature distribution of phosphor layer 2025 when illumination is performed by luminaire 2010 will be shown hereinafter. Similar temperature distributions in related arts 1A and 2A as two techniques related to luminaire 2010 are also shown, and description will be made while comparing these related arts with luminaire 2010. Here, related art 1A is a technique relating to a luminaire which is not provided with both heat transfer plate 2022 and heat dissipation plate 2028 included in luminaire 2010. Related art 2A is a technique relating to a luminaire which is not provided with heat transfer plate 2022 included in luminaire 2010 (is provided with heat dissipation plate 2028).

The simulation estimation is performed by placing each luminaire under a temperature atmosphere of 30° C. while a light source S emits light, and estimating the temperature of the phosphor layer under a steady state in which the temperature of each site of the luminaire is substantially equal to a fixed value (that is, under a state in which the temperature of each site is saturated).

Figure 36:
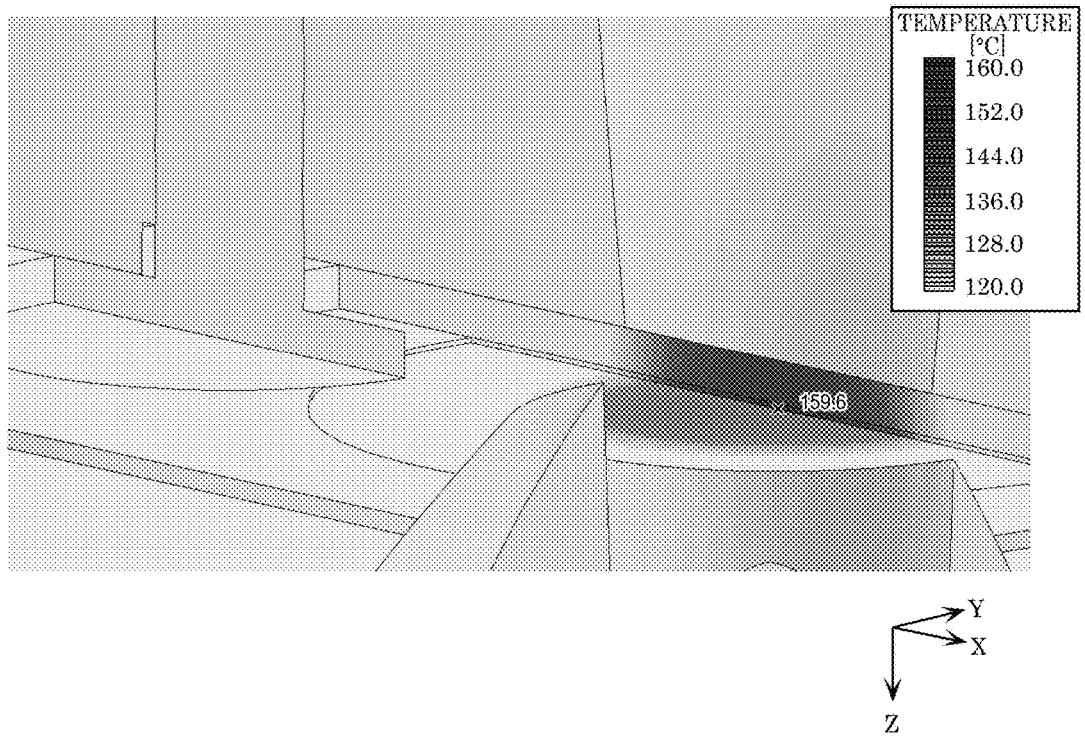
FIG. 36 is a diagram showing a temperature distribution on a cross-section of a luminaire in related art 1A.
Figure 37:
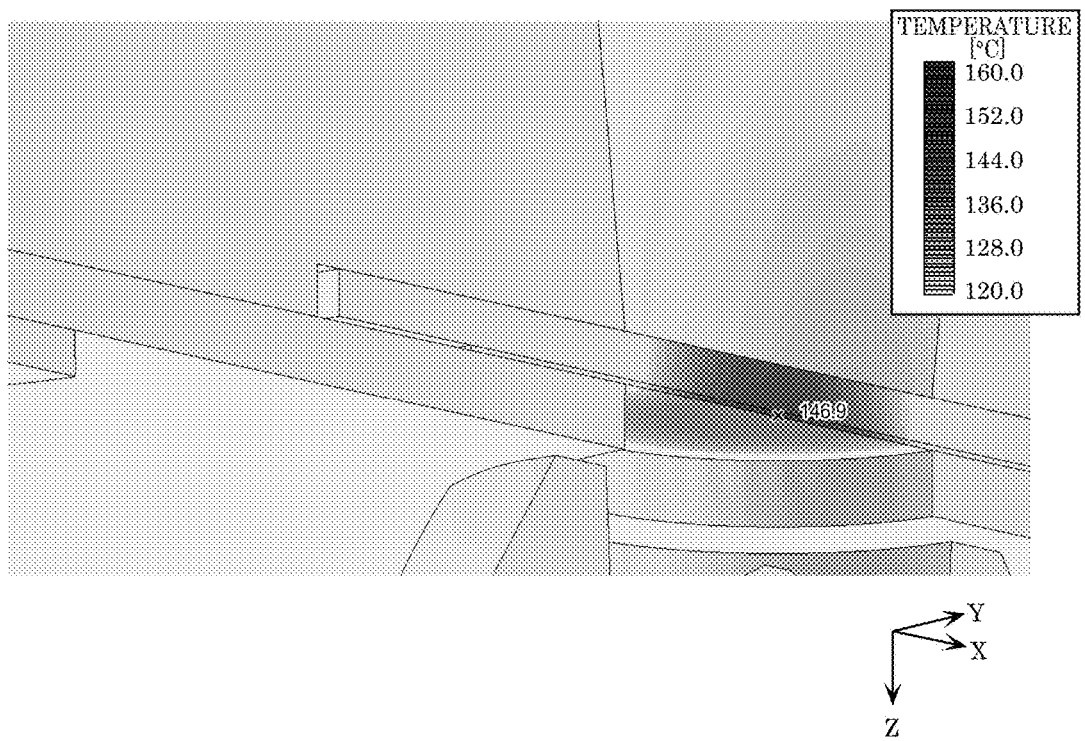
FIG. 37 is a diagram showing a temperature distribution on a cross-section of a luminaire in related art 2A.
Figure 38:
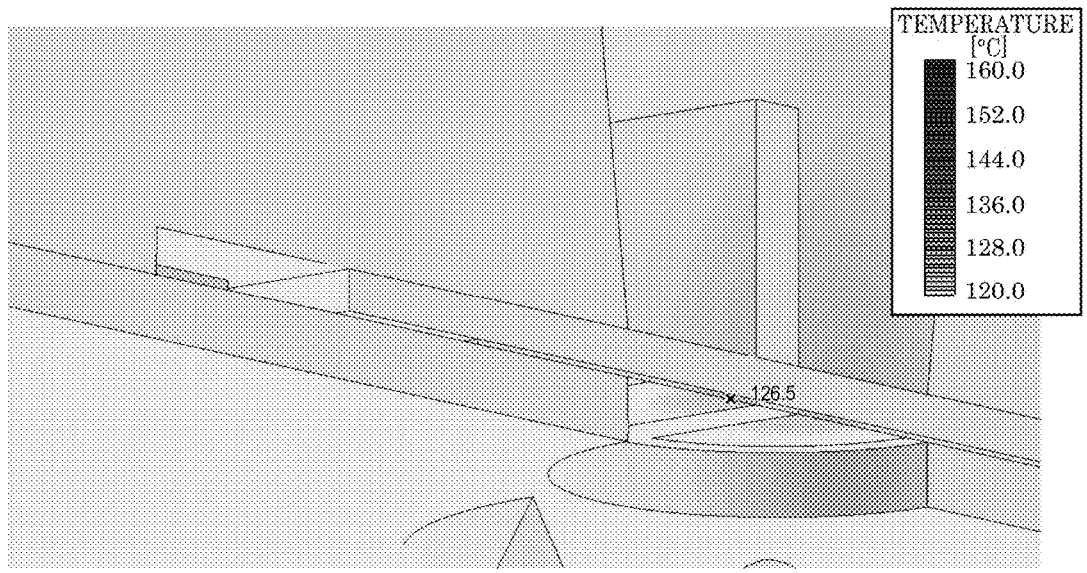
FIG. 38 is a diagram showing a temperature distribution on a cross-section of a luminaire in Embodiment 3.

FIG. 36 is a diagram showing the temperature distribution on a cross-section of the luminaire in related art 1A. FIG. 37 is a diagram showing the temperature distribution on a cross-section of the luminaire and the temperature distribution of the phosphor layer in related art 2A. FIG. 38 is a diagram showing the temperature distribution on a cross-section of luminaire 2010 and the temperature distribution of phosphor layer 2025.

The result of the simulation estimation indicates that the maximum values of the temperature of the phosphor layer in related art 1A and 2A and luminaire 2010 are equal to 159.6° C., 146.9° C., and 126.5° C., respectively.

As described above, an estimation result is obtained, which indicates that, in the case where neither heat transfer plate 2022 nor heat dissipation plate 2028 is provided as in the case of related art 1A, the temperature of the phosphor layer is highest among the three luminaires targeted for the simulation result, that is, the heat dissipation efficiency of the phosphor layer is bad. In the case where heat dissipation plate 2028 is provided (related art 2A), the heat dissipation efficiency is enhanced to a certain degree as compared with related art 1A. Luminaire 2010 provides an estimation result indicating that heat generated by phosphor layer 2025 can be efficiently dissipated to the outside of luminaire 2010 by including heat transfer plate 2022 and heat dissipation plate 2028, and the temperature of phosphor layer 2025 can be reduced at maximum.

Other shapes of heat transfer plate 2022 will be described hereinafter while presenting specific examples.

Figure 39:
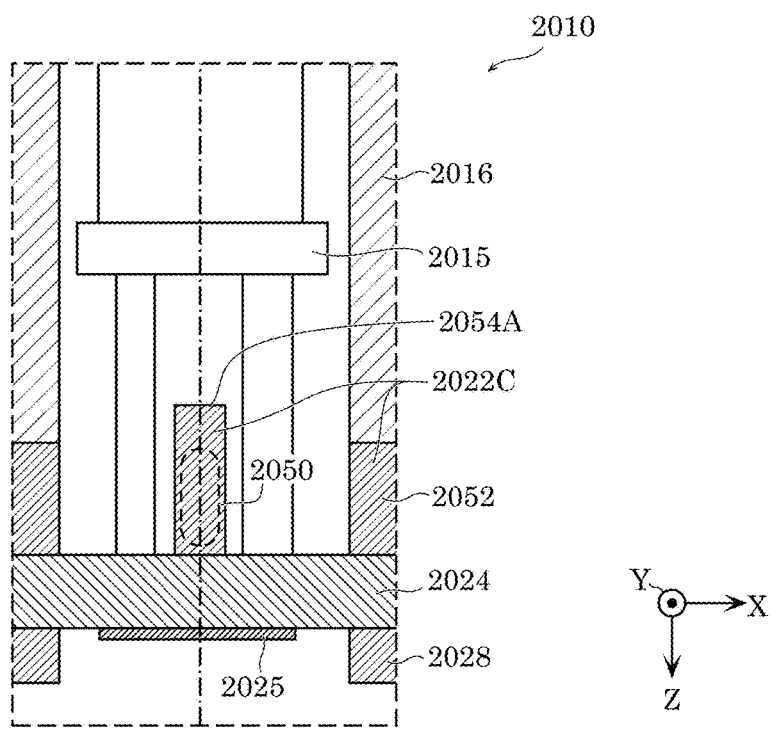
FIG. 39 is a cross-sectional view showing a first example of another shape of the heat transfer plate of the luminaire in Embodiment 3.

FIG. 39 is a cross-sectional view showing a first example (heat transfer plate 2022C) having another shape of the heat transfer plate of luminaire 2010 in this embodiment.

Heat transfer plate 2022C shown in FIG. 39 is formed so that the width in the Z direction of heat transfer body 2054A is relatively large. Heat transfer body 2054A can more greatly transfer heat of center portion 2050 to peripheral portion 2052 because heat transfer body 2054A has a larger volume than heat transfer body 2054. Furthermore, heat transfer plate 2022C has a shape which does not block off the optical path of light emitted from lens array 2015. As a result, the amount of light to be emitted to the outside by luminaire 2010 can be maintained without reduction of the amount of light. As described above, heat transfer body 2054A can suppress the temperature increase of phosphor layer 2025 while maintaining the amount of light to be emitted to the outside by luminaire 2010.

Figure 40:
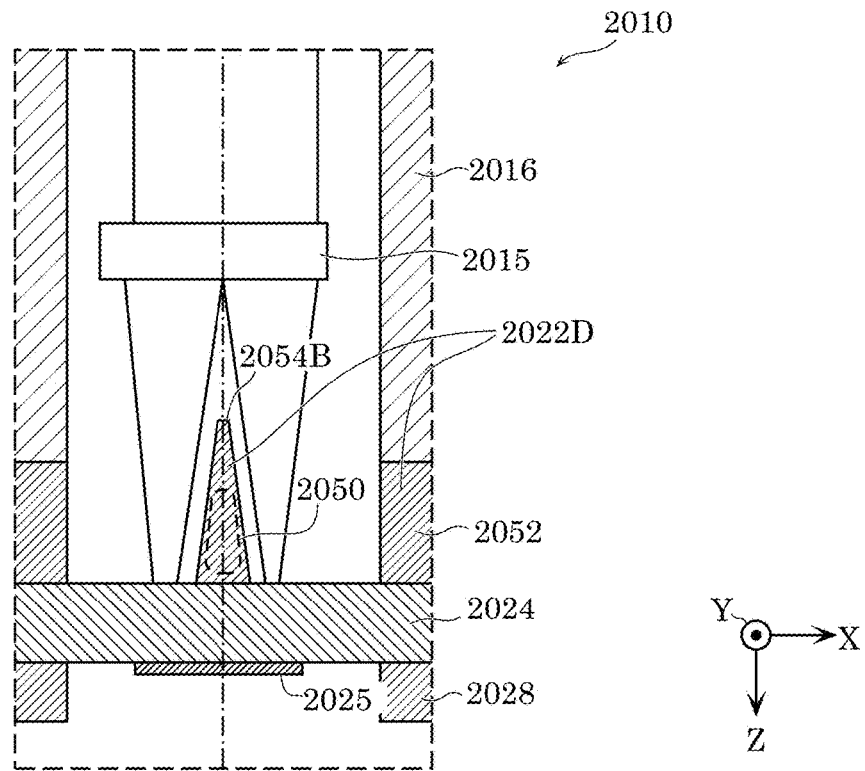
FIG. 40 is a cross-sectional view showing a second example of another shape of the heat transfer plate of the luminaire in Embodiment 3.

FIG. 40 is a cross-sectional view showing a second example (heat transfer plate 2022D) having another shape of the heat transfer plate of luminaire 2010 in this embodiment.

Heat transfer plate 2022D shown in FIG. 40 is shaped so as not to block off the optical paths of light beams emitted from lens array 2015. The optical paths of light beams emitted from lens array 2015 can be determined in design based on the positions and shapes of fiber coupling 2012, lens 2014, and lens array 2015. Therefore, heat transfer body 2054B having a shape which does not block off the optical paths determined as described above can be formed. In other words, heat transfer plate 2022D is positioned and shaped so as to occupy the whole or a part of a space between the optical paths of light beams out of the space on the Z-axis direction plus side beyond lens array 2015.

Specifically, for example, when the width of the light flux emitted from lens array 2015 is smaller as the light travels to board 2024 (that is, in the Z-axis plus direction), heat transfer body 20546 is tapered so that the width thereof is smaller as the position thereof shifts in the Z-axis minus direction. Heat transfer body 2054B can also suppress the temperature increase of phosphor layer 2025 while maintaining the amount of light emitted to the outside by luminaire 2010.

Heat transfer plates 2022C and 2022D having the other shapes of heat transfer plate 2022 (heat transfer body 2054) as described above make it possible to increase the amount of heat to be transferred from center portion 2050 of the heat transfer plate to peripheral portion 2052 thereof.

A specific configuration of lens array 2015 will be described hereinafter.

Figure 41:
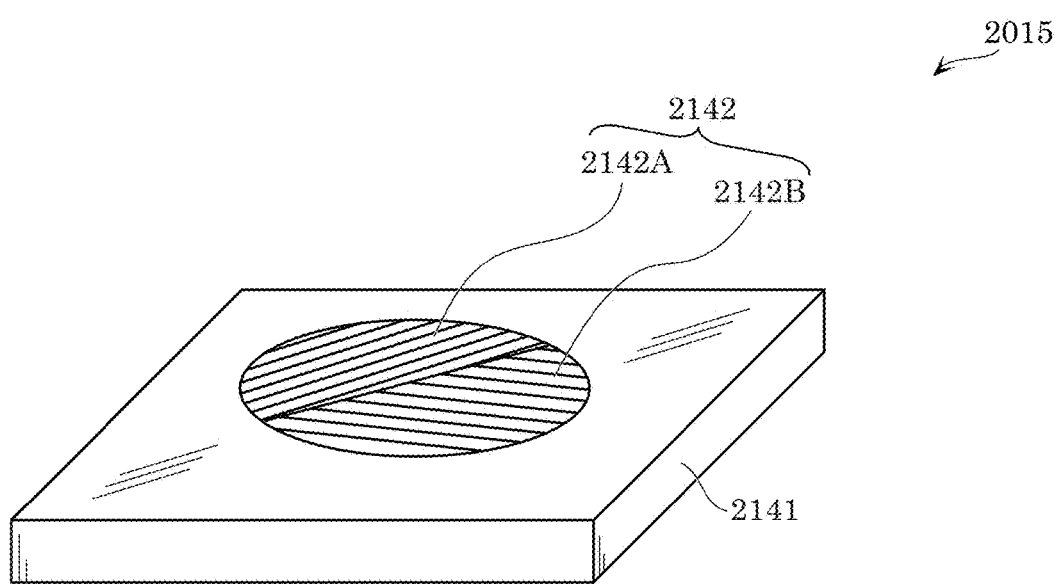
FIG. 41 is a perspective view showing a specific configuration of a lens of the luminaire in Embodiment 3.
Figure 42:
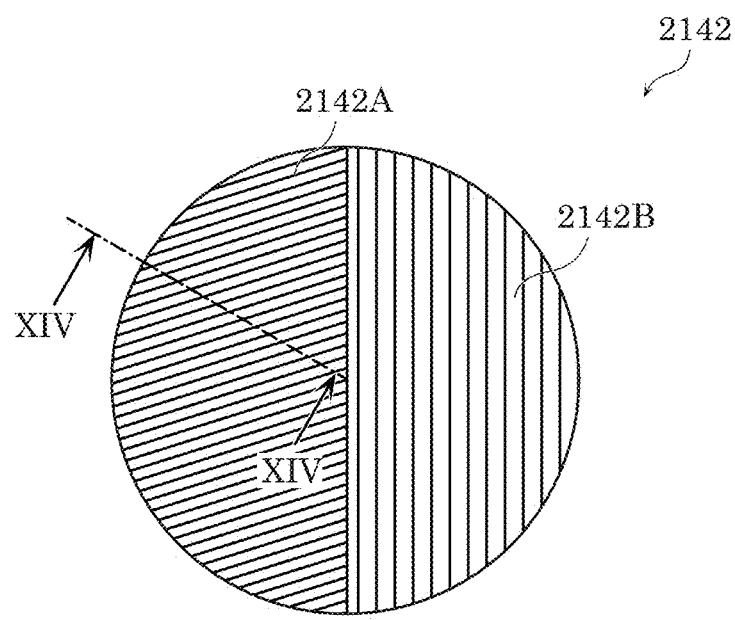
FIG. 42 is a top view showing a configuration of a diffraction type lens array in Embodiment 3.
Figure 43:
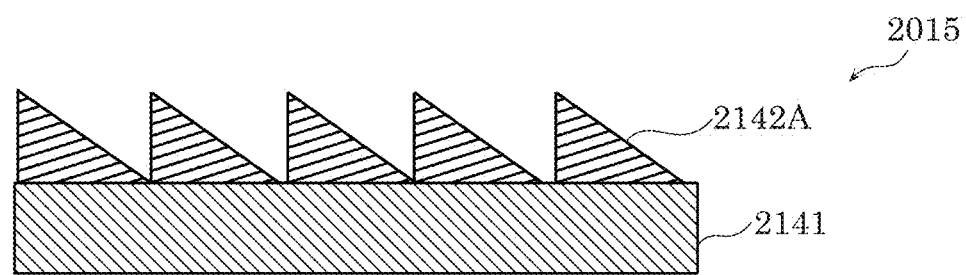
FIG. 43 is a cross-sectional view on XIV-XIV line of FIG. 42.

FIG. 41 is a perspective view showing the configuration of lens array 2015 of luminaire 2010 in this embodiment. FIG. 42 is a top view showing the configuration of diffraction type lens array 2142 of luminaire 2010 in this embodiment. FIG. 43 is a cross-sectional view on XIV-XIV line of FIG. 42.

Lens array 2015 is arranged between fiber coupling 2012 and phosphor member 2020, splits and separates light introduced from light source S into luminaire 2010 via optical fiber F and fiber coupling 2012, and emits the split and separated light to phosphor member 2020. Lens array 2015 is an example of the microlens array, and includes base material 2141 and diffraction type lens array 2142 as shown in FIG. 41, for example.

Base material 2141 is the base material of the microlens array. Diffraction type lens array 2142 is formed on base material 2141. Any material such as glass or plastic may be used as the material for forming base material 2141 as in the case of board 2024.

Diffraction type lens array 2142 splits and separates light introduced into luminaire 2010, and emits the split and separated light to phosphor member 2020. The cross-sectional shape of diffraction type lens array 2142 on a plane perpendicular to the incidence face of phosphor member 2020 is a sawtooth shape. Furthermore, diffraction type lens array 2142 has plural areas where the arrangement direction of saw teeth is identical in the same area, but different among different areas.

This embodiment presents an example in which diffraction type lens array 2142 has areas 2142A and 2142B (hereinafter also represented as areas 2142A, etc.) as two areas between which the arrangement directions of saw teeth are different as shown in FIG. 41 and FIG. 42, for example. In FIG. 41 and FIG. 42, plural linearly-arranged lens arrays are provided and the arrangement directions of the plural lens arrays are identical to one another in the same area of each of two areas 2142A, etc. Here, when the wavelength of blue light from light source S is equal to, for example, 460 nm, the grating pitch of the plural lens arrays is equal to, for example, 5 µm, and the grating height is equal to 1 µm. The cross-sectional shape on XIV-XIV line of FIG. 42 is a sawtooth shape as shown in FIG. 43. Here, the cross-section indicated by the XIV-XIV line corresponds to the plane perpendicular to the incidence face of phosphor member 2020 described above. The cross-sectional shape of diffraction type lens array 2142 in area 2142A is show in FIG. 43, and the cross-sectional shape in the other area 2142B is likewise a sawtooth shape. That is, diffraction type lens array 2142 corresponds to a so-called blazed diffraction grating. Accordingly, diffraction type lens array 2142 can enhance the primary diffraction efficiency, and reduce the loss of light (optical loss).

In diffraction type lens array 2142, the arrangement direction of saw teeth is different between two areas 2142A, etc. as shown in FIG. 42, for example. The configuration described above enables diffraction type lens array 2142 to prevent energy concentration on the incidence face of phosphor member 2020 even when light introduced into luminaire 2010 is split and separated, and emitted to phosphor member 2020.

The material for diffraction type lens array 2142 is selected according to the forming method, heat resistance, and refractive index of diffraction type lens array 2142. Nanoimprint, print, photolithography, EB lithography, particle orientation or the like is available as the method of forming diffraction type lens array 2142. When diffraction type lens array 2142 is formed, for example by nanoimprint or print, UV curing resin such as epoxy resin or acrylic resin, thermoplastic resin such as polymethyl methacrylate (PMMA) may be selected as the material of diffraction type lens array 2142. Furthermore, in consideration of heat resistance, glass or quartz may be selected as the material of diffraction type lens array 2142, and diffraction type lens array 2142 may be formed by photolithography or EB lithography. Diffraction type lens array 2142 may be formed of a material having the same level refractive index as base material 2141 to facilitate entry of light from base material 2141 to diffraction type lens array 2142. Furthermore, it is preferable that diffraction type lens array 2142 does not absorb light and is transparent as in the case of base material 2141, and also it is preferable that diffraction type lens array 2142 is formed of a material whose extinction coefficient is substantially equal to zero.

Next, the optical path of light in luminaire 2010 when diffraction type lens array 2142 described above is used will be described.

Figure 44:
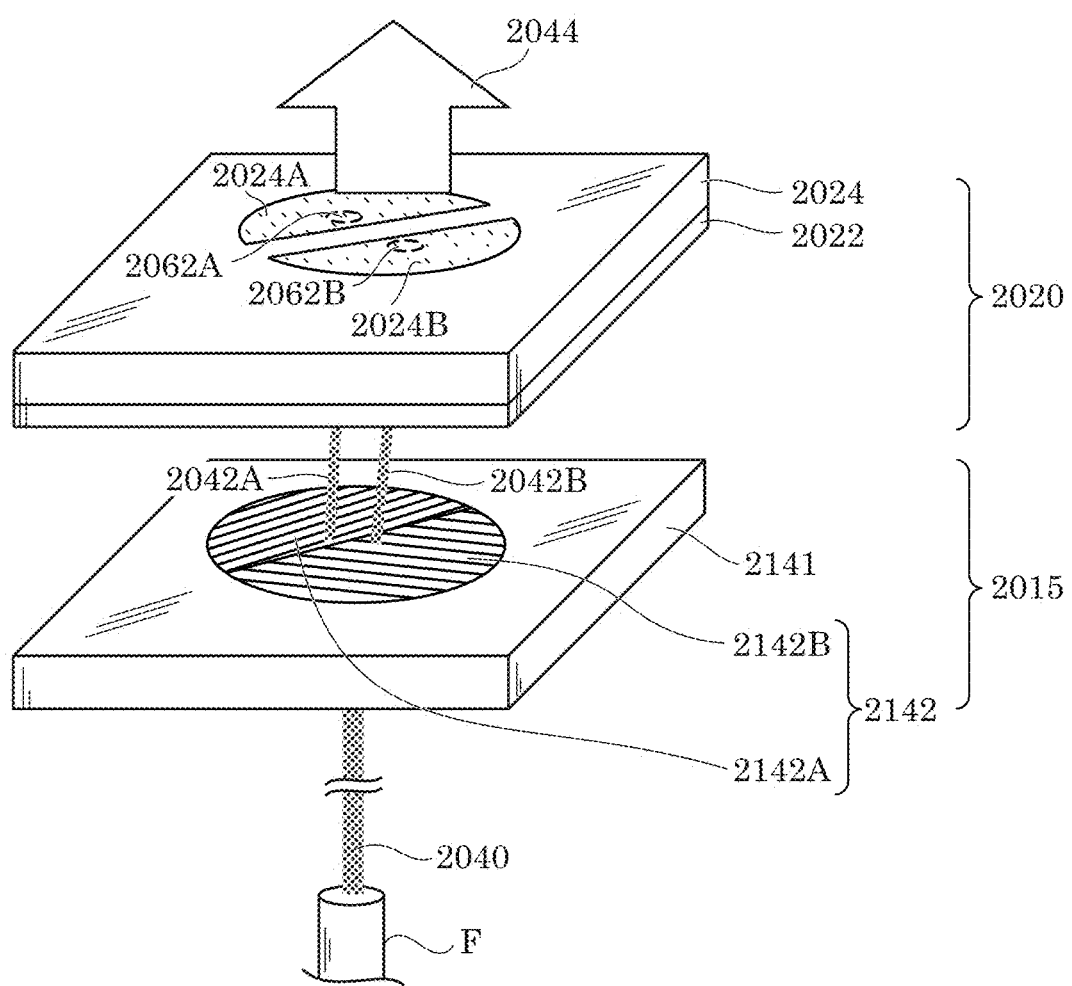
FIG. 44 is a perspective view showing optical paths of light beams passing through the diffraction type lens array in Embodiment 3.

FIG. 44 is a perspective view showing the optical path of light passing through diffraction type lens array 2142 of luminaire 2010 in this embodiment.

As shown in FIG. 44, luminaire 2010 in this embodiment splits and separates light 2040 introduced into luminaire 2010 into two light beams 2042A and 2042B (hereinafter also represented as light beams 2042A, etc.), and emits the light beams to phosphor member 2020 by diffraction type lens array 2142. As described above, light 2040 introduced into luminaire 2010 can be split and separated without greatly changing the spot diameter of light 2040, and projected onto phosphor member 2020. In phosphor member 2020, the split and separated light beams 2042A, etc. are incident on different areas of the incidence face, so that energy concentration on the incidence face of phosphor member 2020 can be prevented. Phosphor member 2020 can generate white light 2044 by using incident light beams 2042A, etc.

Variations of heat transfer plate 2022 and board 2024 will be described hereinafter.

Variation 1 of Embodiment 3

In this variation, a luminaire including a heat transfer plate having three opening portions and a phosphor layer divided into three areas will be described. In the luminaire in this variation, the same constituent elements as luminaire 2010 of Embodiment 3 are represented by the same reference marks, and detailed description thereof is omitted.

The luminaire in this variation includes fiber coupling 2012, lenses 2014 and 2030, lens array 2015B, holder 2016, and phosphor member 2020 as in the case of luminaire 2010. Phosphor member 2020 includes heat transfer plate 2082, board 2084, phosphor layers 2085A, 2085B, and 2085C (hereinafter also represented as phosphor layers 2085A, etc.), and heat dissipation plate 2028. The constituent elements excluding heat transfer plate 2082, board 2084, and phosphor layers 2085A, etc. out of the foregoing constituent elements are the same as those represented by the same terms in Embodiment 3 (FIG. 31, FIG. 32, etc.), and detailed description thereof is omitted.

Figure 45:
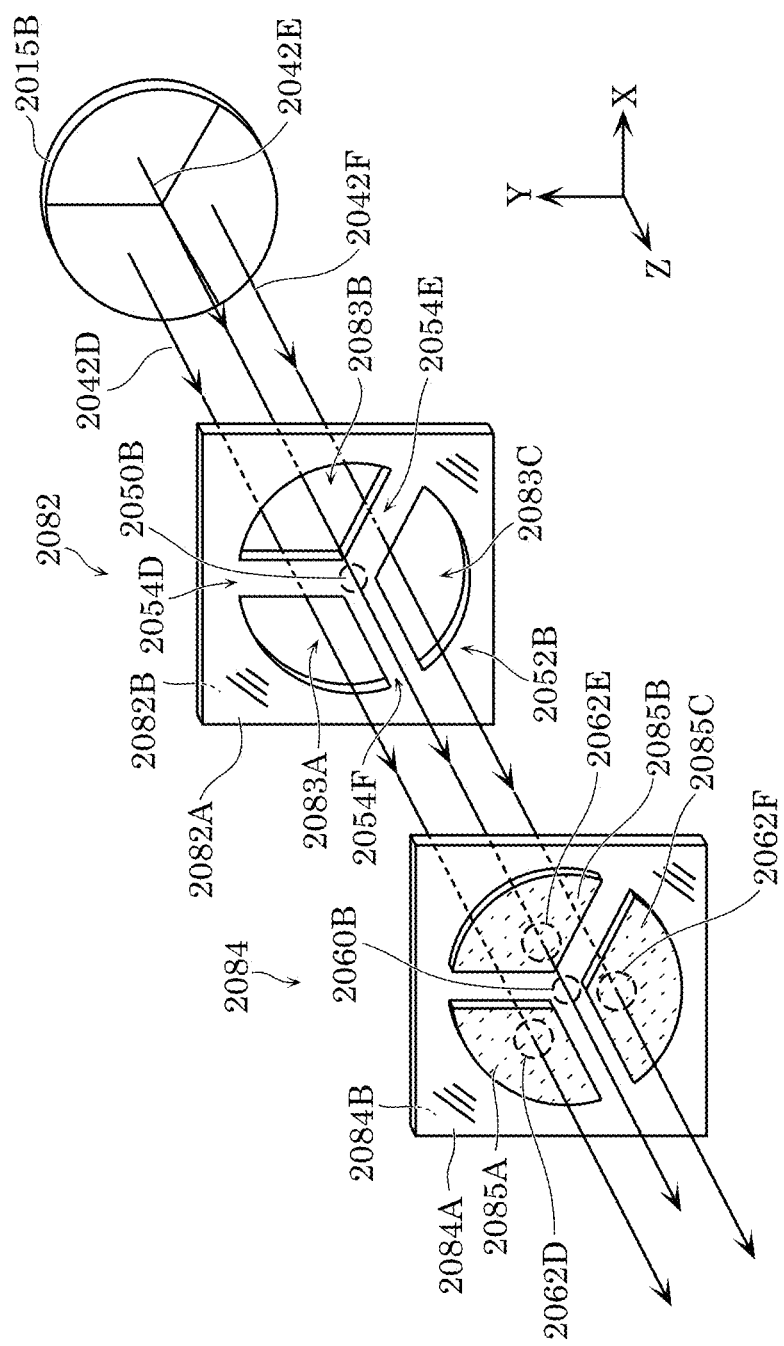
FIG. 45 is a schematic diagram showing specific shapes of a heat transfer plate and a board, and optical paths of light beams in Variation 1 of Embodiment 3.

FIG. 45 is a schematic diagram showing specific shapes of heat transfer plate 2082, board 2084, and phosphor layers 2085A, etc. and the optical paths of light beams in this variation. In FIG. 45, the first surface of heat transfer plate 2082 is represented as surface 2082A, and the second surface thereof is represented as surface 2082B. The first surface of board 2084 is represented surface 2084A, and the second surface thereof is represented as surface 2084B.

As shown in FIG. 45, lens array 2015B splits light emitted from lens 2014 into light beams 2042D, 2042E, and 2042F (hereinafter represented as light beams 2042D, etc.) traveling along three optical paths, respectively.

Heat transfer plate 2082 includes three opening portions 2083A, 2083B, and 2083C (hereinafter also represented as opening portions 2083A, etc.). Three opening portions 2083A, etc. have a substantially circular shape as a whole, and light beams 2042D, 2042E, and 2042F (hereinafter also represented as light beams 2042D, etc.) which are emitted from lens array 2015B and travel in the Z-axis plus direction pass through opening portions 2083A, etc. Heat transfer plate 2082 has three heat transfer bodies 2054D, 2054E, and 2054F (hereinafter also represented as heat transfer bodies 2054D, etc.) extending from center portion 2050B of heat transfer plate 2082 to peripheral portion 2052B thereof. It may be said that opening portions 2083A, etc. are partitioned by heat transfer bodies 2054D, etc.

Board 2084 is a board having three portions coated with phosphor layers 2085A, etc. Phosphor layers 2085A, etc. are irradiated, from the surface 2084B side, with light beams 2042D, etc. which are emitted from lens array 2015B and pass through opening portions 2083A, etc. In FIG. 45, areas to be irradiated with these light beams are represented as areas 2062D, 2062E, and 2062F, respectively.

In the luminaire in this variation, light emitted from lens array 2015B is split into three light beams, and thus the temperature around center portion 2060B of board 2084 is lower as compared with a case where light is split into two light beams. As a result, the temperature increase of phosphor layers 2085A, etc. is more greatly suppressed, and deterioration of phosphor layers 2085A, etc. is more greatly suppressed.

As described above, luminaire 2010 of Embodiment 3 includes board 2024 having light-transmissivity and including a portion provided with phosphor layer 2025, heat transfer plate 2022 which is arranged in surface contact with board 2024, and includes one or more opening portions 2023 arranged at a position overlapping with the above portion, and heat dissipation plate 2028 which is arranged in surface contact with a surface of board 2024 on the opposite side to the surface of board 2024 in surface contact with heat transfer plate 2022, and includes opening portion 2029 at a position overlapping with one or more opening portions 2023 of heat transfer plate 2022.

According to this configuration, heat occurring when phosphor layer 2025 converts the wavelength of light is transferred to heat transfer plate 2022 via board 2024, and heat transfer plate 2022 dissipates the heat to the air in contact with holder 2016 and heat transfer plate 2022. As described above, the temperature increase of phosphor layer 2025 can be suppressed by existence of heat transfer plate 2022. Accordingly, luminaire 2010 can enhance the heat dissipation efficiency while preventing increase of the size of the luminaire.

Furthermore, heat transfer plate 2022 has heat transfer body 2054 which is arranged so as to extend from center portion 2050 of heat transfer plate 2022 to peripheral portion 2052 thereof.

According to this configuration, heat transfer plate 2022 transfer the heat generated by phosphor layer 2025 from center portion 2050 of heat transfer plate 2022 to peripheral portion 2052 thereof via heat transfer body 2054. This makes it possible to prevent the temperature increase of center portion 2060 of board 2024 on which heat generated by phosphor layer 2025 is liable to concentrate.

Furthermore, heat transfer body 2054 is arranged at equiangular intervals around center portion 2050.

According to this configuration, heat transfer bodies 2054D, 2054E, and 2054F can transfer heat from center portion 2050B of heat transfer plate 2082 to peripheral portion 2052B thereof uniformly without deviation in direction. As a result, the temperature increase of phosphor layers 2085A, etc. can be prevented uniformly without deviation in direction when viewed from center portion 2050B of heat transfer plate 2082.

Light from light source S enters luminaire 2010, and heat transfer body 2054 is positioned so that the optical path of light passes through one or more opening portions 2023.

According to this configuration, heat transfer plate 2022 passes, via opening portion 2023, light which is irradiated from light source S via lens array 2015. As a result, the amount of light to be emitted to the outside by luminaire 2010 can be maintained without reducing the amount of light.

Heat transfer bodies 2054A and 2054B are positioned and shaped so as to occupy the whole or a part of the internal space of luminaire 2010 excluding the optical path of light.

According to this configuration, heat transfer bodies 2054A and 2054B can more greatly transfer heat of center portion 2050 to peripheral portion 2052, and also do not block off light irradiated from the light source via lens array 2015. Accordingly, the temperature increase of phosphor layer 2025 can be prevented while the amount of light to be emitted to the outside by luminaire 2010 can be maintained without reducing the amount of light.

Phosphor layer 2025 receives incident blue light and converts a part of the received blue light to yellow light, one or more opening portions 2023 of heat transfer plate 2022 are arranged on an extension line of the optical path of the blue light, and opening portion 2029 of heat dissipation plate 2028 is arranged on an extension line of the optical path and passes therethrough white light generated from the blue light received by phosphor layer 2025 and the yellow light generated by conversion of the phosphor layer to the outside of luminaire 2010.

According to this configuration, luminaire 2010 can emit white light to the outside by using incident blue light, and prevent temperature increase of phosphor layer 2025.

Lighting apparatus 2001 of Embodiment 3 includes luminaire 2010 described above, light source S, and optical fiber F for leading light emitted from light source S to luminaire 2010, and phosphor layer 2025 provided to board 2024 of luminaire 2010 receives light led by optical fiber F.

According to this configuration, lighting apparatus 2001 has the same effect as luminaire 2010.

Embodiment 4

In this embodiment, another configuration of the luminaire having enhanced heat dissipation efficiency while preventing increase in size will be described. The same constituent elements as those of Embodiment 3 are represented by the same reference marks, and detailed description thereof may be omitted.

Figure 46:
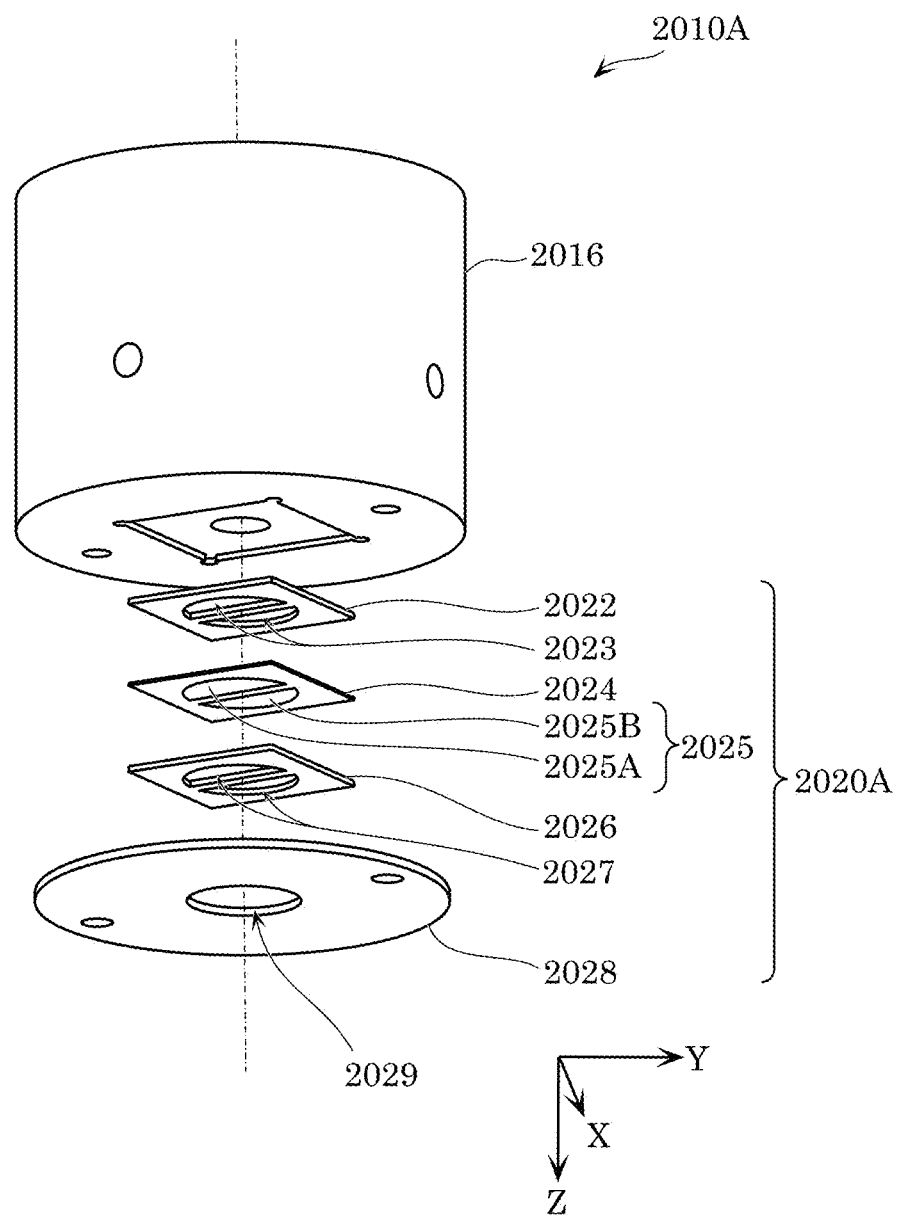
FIG. 46 is an exploded perspective view of a holder and a phosphor member included in a luminaire in Embodiment 4.
Figure 47:
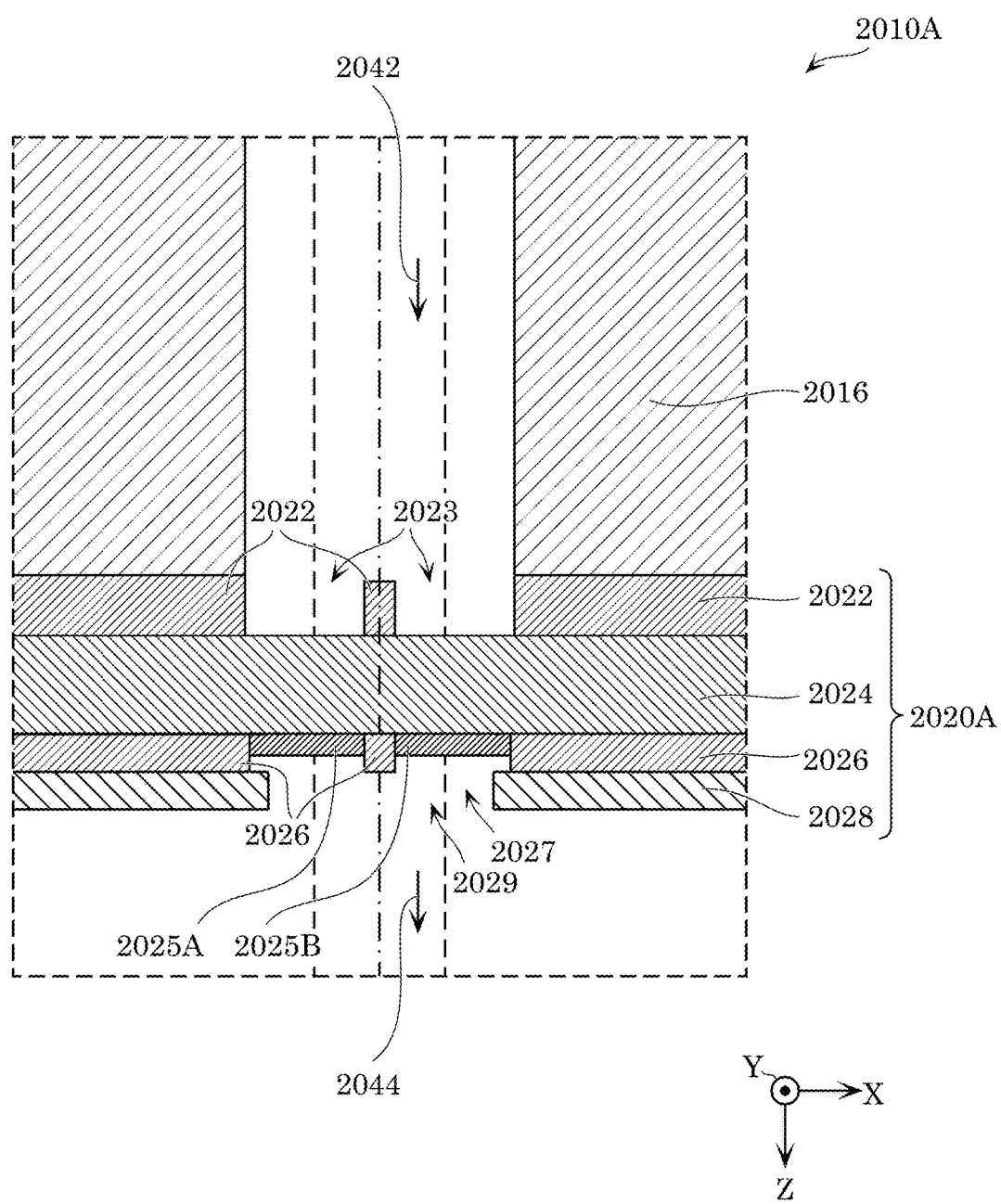
FIG. 47 is a cross-sectional view of the holder and the phosphor member included in the luminaire in Embodiment 4.

FIG. 46 is an exploded perspective view of holder 2016 and phosphor member 2020A included in luminaire 2010A in this embodiment. FIG. 47 is a cross-sectional view of holder 2016 and phosphor member 2020A included in luminaire 2010 in this embodiment. The cross-sectional view shown in FIG. 47 shows the cross-section (II-II line of FIG. 30) which corresponds to the same position as the cross-sectional view of luminaire 2010 of Embodiment 3.

As shown in FIG. 46 and FIG. 47, phosphor member 2020A includes heat transfer plates 2022 and 2026, board 2024, phosphor layer 2025, and heat dissipation plate 2028. Here, luminaire 2010A is different from luminaire 2010 in that luminaire 2010A includes heat transfer plate 2026. Furthermore, phosphor layer 2025 has plural portions (phosphor layers 2025A and 2025B). Opening portion 2023 of heat transfer plate 2022 is an example of the first opening portion.

Heat transfer plate 2026 is a plate-shaped heat transfer body for transferring heat generated by phosphor layer 2025 to heat dissipation plate 2028. Heat transfer plate 2026 is arranged between board 2024 and heat dissipation plate 2028 so as to be in surface contact with each of board 2024 and heat dissipation plate 2028, heat generated by phosphor layer 2025 is transferred to heat transfer plate 2026 via board 2024, and heat transfer plate 2026 further transfers the heat to heat dissipation plate 2028, thereby suppressing the temperature increase of phosphor layer 2025. At the portion of heat transfer plate 2026 which is in direct contact with phosphor layer 2025, the heat generated by phosphor layer 2025 is transferred directly, that is, not via board 2024 to heat transfer plate 2026, which also suppresses the temperature increase of phosphor layer 2025. The material for forming heat transfer plate 2026 is the same as heat transfer plate 2022. A surface of heat transfer plate 2026 which is in contact with heat dissipation plate 2028 is also referred as a first surface, and a surface of heat transfer plate 2026 which is on the opposite side to the first surface and in contact with board 2024 is also referred to as a second surface.

Heat transfer plate 2026 is arranged so that the second surface thereof is in surface contact with the surface of board 2024 on which phosphor layer 2025 is coated, and has opening portion 2027 at a position overlapping with a portion coated with phosphor layer 2025 on the second surface. Opening portion 2027 is an opening for passing light emitted from phosphor layer 2025 to the Z-axis plus side when heat transfer plate 2026 is arranged in surface contact with board 2024. More specifically, opening portion 2027 is arranged on an extension line of the optical path of blue light received by phosphor layer 2025, and passes therethrough white light generated from blue light received by phosphor layer 2025 and yellow light generated by conversion of phosphor layer 2025. The white light emitted from phosphor layer 2025 passes through opening portion 2027, further passes through opening portion 2029 of heat dissipation plate 2028, and is emitted to the outside of luminaire 2010A. In other words, heat transfer plate 2026 is positioned so that the optical path of the white light passes through opening portion 2027. Opening portion 2027 is an example of the second opening portion.

Heat dissipation plate 2028 is a heat dissipation member which is arranged in surface contact with the first surface of heat transfer plate 2026, and has opening portion 2029 at a position overlapping with opening portion 2027 of heat transfer plate 2026. Opening portion 2029 is arranged on an extension line of the optical path of light emitted from lens array 2015, and passes therethrough white light passing through opening portion 2027 of heat transfer plate 2026 to the outside of luminaire 2010A. Heat dissipation plate 2028 is the same as heat dissipation plate 2028 in Embodiment 3. Opening portion 2029 is an example of a third opening portion.

Phosphor layer 2025 is configured so that the thickness in the Z-direction thereof is less than or equal to the thickness in the Z-direction of heat transfer plate 2026. Phosphor layer 2025 may be configured so that the thickness in the Z-direction thereof is substantially equal to the thickness in the Z-direction of heat transfer plate 2026, that is, the interface between phosphor layer 2025 and heat dissipation plate 2028 is flush with the interface between heat transfer plate 2026 and heat dissipation plate 2028. According to this configuration, heat generated by phosphor layer 2025 is transferred to heat dissipation plate 2028 directly, that is, via neither board 2024 nor heat transfer plate 2026, whereby the amount of heat transfer can be more increased.

Figure 48:
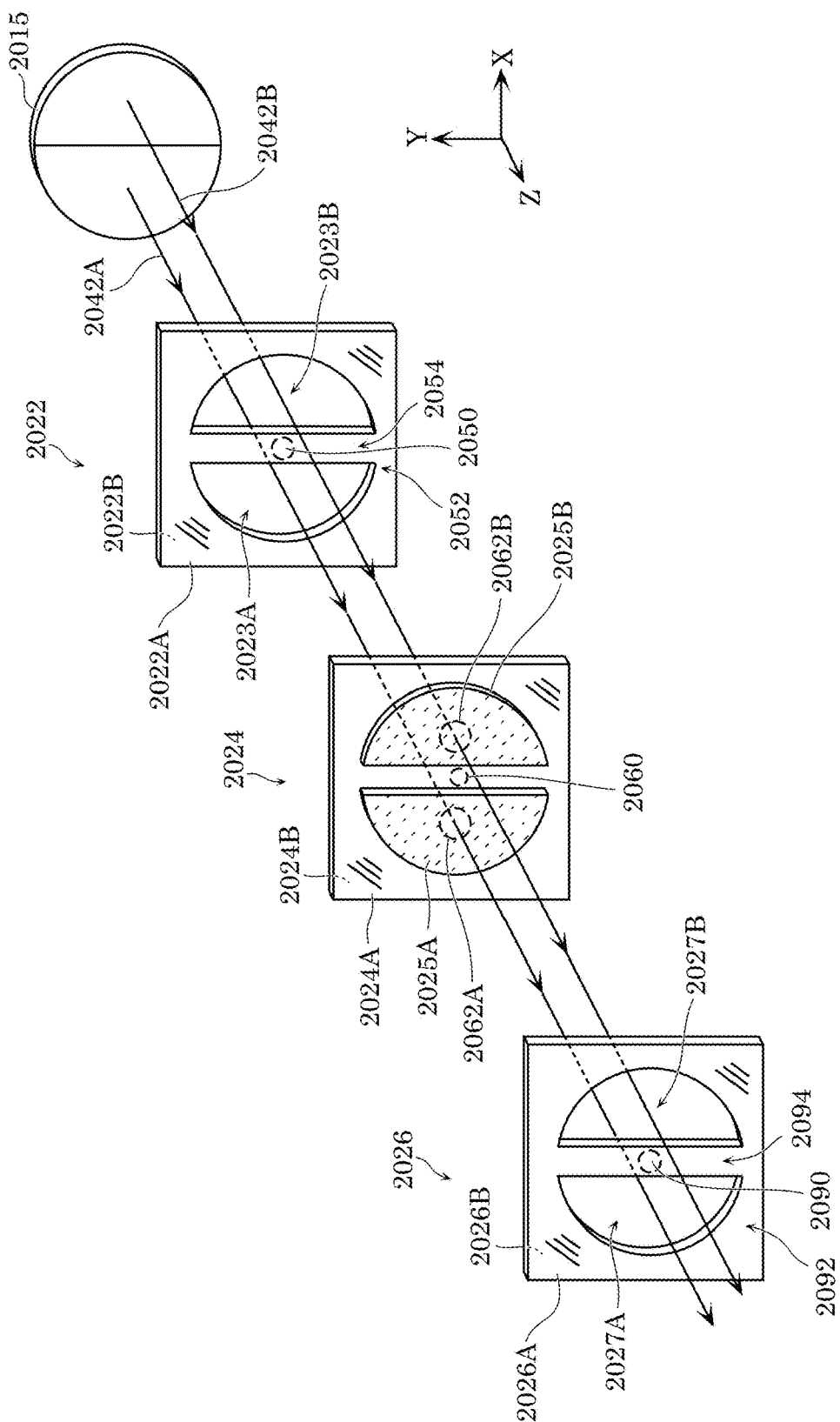
FIG. 48 is a schematic diagram showing specific shapes of the heat transfer plate and the board, and optical paths of light beams in Embodiment 4.

FIG. 48 is a schematic diagram showing specific shapes of heat transfer plates 2022 and 2026 and board 2024, and the optical path of light in this embodiment. In FIG. 48, heat transfer plates 2022 and 2026 and board 2024 are illustrated as being exploded for description. Actually, heat transfer plates 2022 and 2026 and board 2024 are arranged in contact with each other. In FIG. 48, the first surface of heat transfer plate 2026 is represented as surface 2026A, and the second surface is represented as surface 2026B. Heat transfer plate 2022 and board 2024 are the same as those of Embodiment 3 (FIG. 34).

As shown in FIG. 48, heat transfer plate 2026 includes plural opening portions 2027A and 2027B (hereinafter also referred to as opening portions 2027A, etc.) as opening portion 2027. Opening portions 2027A, etc. have the same shapes as phosphor layers 2025A, etc. of FIG. 48, respectively. Therefore, when board 2024 and heat transfer plate 2026 are overlapped with each other, each of phosphor layers 2025A, etc. and each of opening portions 2027A, etc. are overlapped with each other. Accordingly, light beams which are transmitted through or emitted from phosphor layers 2025A, etc. in the Z-axis plus direction pass through opening portions 2027A, etc. Heat transfer plate 2026 has heat transfer body 2094 extending from center portion 2090 of heat transfer plate 2026 to peripheral portion 2092 thereof. It may be said that opening portions 2027A, etc. are partitioned by heat transfer body 2094.

Heat transfer body 2094 may have another shape (for example, a radial shape) insofar as heat transfer body 2094 extends from center portion 2090 of heat transfer plate 2026 to peripheral portion 2092 thereof as in the case of heat transfer body 2054 of heat transfer plate 2022, and may be arranged in equiangular intervals around center portion 2090. This configuration makes it possible to reduce deviation in heat flow direction from center portion 2090 of heat transfer plate 2026 to peripheral portion 2092 thereof, and also reduce the temperature of phosphor layer 2025 without deviation.

Heat transfer body 2094 may have another shape insofar as heat transfer body 2094 is formed to have a shape which does not block off the optical paths of light beams emitted from phosphor layers 2025A and 2025B. Since the optical paths of light beams emitted from phosphor layers 2025A and 2025B may be determined in design based on the positions and shapes of phosphor layers 2025A and 2025B, heat transfer body 2094 having a shape which does not block off the optical paths determined as described above can be formed.

A simulation estimation result for heat transfer performance in luminaire 2010A configured as described above will be described.

Figure 49:
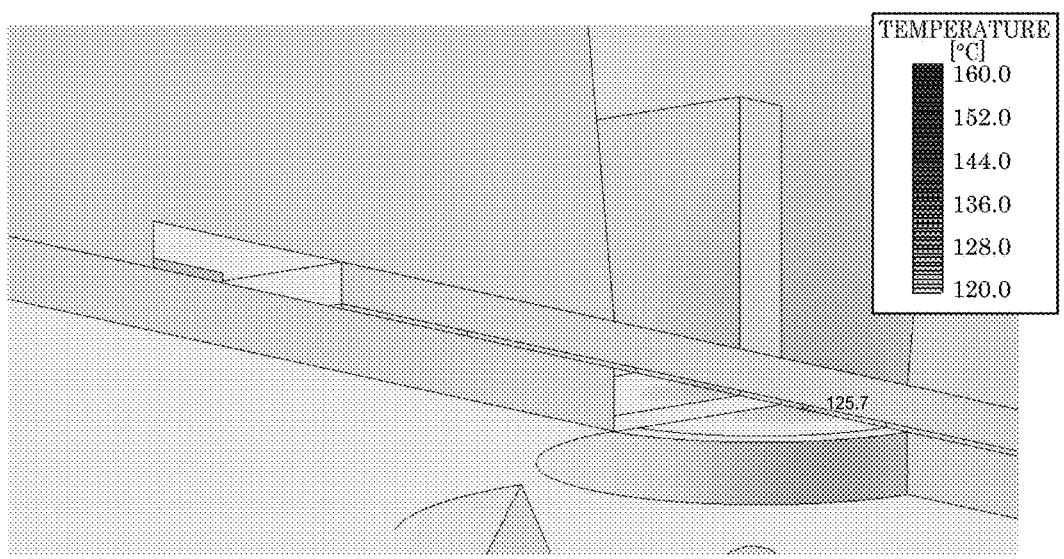
FIG. 49 is a diagram showing a temperature distribution on a cross-section of a luminaire and a temperature distribution of a phosphor layer in Embodiment 4.

FIG. 49 is a diagram showing a temperature distribution on a cross-section of luminaire 2010A and a temperature distribution of phosphor layer 2025 in this embodiment. This cross-section is a cross-section of luminaire 2010A at the same position as the cross-section of luminaire 2010 shown in FIG. 35.

The simulation estimation result indicates that the maximum value of the temperature of the phosphor layer in luminaire 2010A is equal to 125.7° C. This temperature is lower than those of three luminaires (related arts 1A and 2A, and luminaire 2010) providing the simulation results in Embodiment 3.

As described above, there is obtained an estimation result indicating that luminaire 2010A can efficiently dissipate heat generated by phosphor layer 2025 to the outside of luminaire 2010A by including heat transfer plates 2022 and 2026 and heat dissipation plate 2028, and the temperature of the phosphor layer can be reduced at maximum.

As described above, luminaire 2010A in this embodiment includes: board 2024 having light-transmissivity and including one or more portions provided with phosphor layer 2025; heat transfer plate 2022 which is arranged in surface contact with board 2024, and includes one or more opening portions 2023 arranged at a position overlapping with the one or more portions; heat transfer plate 2026 which is arranged in surface contact with a surface on the opposite side of board 2024 to the surface of board 2024 in surface contact with heat transfer plate 2022, and includes one or more opening portions 2027 arranged at a position overlapping with the one or more portions, respectively; and heat dissipation plate 2028 which is arranged in surface contact with a surface on the opposite side of heat transfer plate 2026 to the surface of heat transfer plate 2026 in surface contact with board 2024, and includes opening portion 2029 at a position overlapping with one or more opening portions 2027 of heat transfer plate 2026.

According to this configuration, heat generated when phosphor layer 2025 converts the wavelength of light is transferred to heat transfer plate 2022 via board 2024, and heat transfer plate 2022 dissipates the heat to the air which is in contact with holder 2016 and heat transfer plate 2022. Furthermore, the heat is transferred to heat transfer plate 2026 via board 2024, and heat transfer plate 2026 dissipates the heat to the air which is in contact with heat dissipation plate 2028 and heat transfer plate 2026. As described above, the temperature increase of phosphor layer 2025 can be suppressed by existence of heat transfer plates 2022 and 2026. Accordingly, luminaire 2010A can enhance the heat dissipation efficiency while preventing increase of the size of the luminaire.

Furthermore, board 2024 has plural portions as the one or more portions. Heat transfer plate 2022 has plural opening portions 2023 as one or more opening portions 2023 which are arranged at positions overlapping with the plural portions, respectively. Heat transfer plate 2026 has plural opening portions 2027 as one or more opening portions 2027 which are arranged at positions overlapping with the plural portions, respectively.

According to this configuration, even when phosphor layer 2025 is arranged at plural places of board 2024, heat transfer plates 2022 and 2026 transfer heat generated by phosphor layer 2025 to holder 2016 and heat dissipation plate 2028. Therefore, luminaire 2010A can enhance the heat dissipation efficiency while preventing increase of the size of the luminaire.

Furthermore, heat transfer plate 2022 has heat transfer body 2054 arranged to extend from center portion 2050 of heat transfer plate 2022 to peripheral portion 2052 thereof, and heat transfer plate 2026 has heat transfer body 2094 arranged to extend from center portion 2090 of heat transfer plate 2026 to peripheral portion 2092 thereof.

According to this configuration, heat transfer plates 2022 and 2026 transfer heat generated by phosphor layer 2025 from center portion 2050 of heat transfer plate 2022 to peripheral portion 2052 thereof via heat transfer body 2054, and also transfer the heat to holder 2016. Furthermore, heat transfer plates 2022 and 2026 transfer the heat from center portion 2090 of heat transfer plate 2026 to peripheral portion 2092 thereof via the heat transfer body, and also transfer the heat to heat dissipation plate 2028. As a result, the temperature increase of center portion 2060 of board 2024 on which heat generated by phosphor layer 2025 is liable to concentrate can be prevented.

Furthermore, heat transfer body 2054 is arranged at equiangular intervals around center portion 2050, and heat transfer body 2094 is arranged at equiangular intervals around center portion 2090.

According to this configuration, heat transfer body 2054 can transfer heat uniformly without deviation in direction from center portion 2050 of heat transfer plate 2022 to peripheral portion 2052 thereof, and also heat transfer body 2094 can transfer heat uniformly without deviation in direction from center portion 2090 of heat transfer plate 2026 to peripheral portion 2092 thereof. As a result, the temperature increase of phosphor layer 2025 can be prevented uniformly without deviation in direction when viewed from center portions 2050 and 2090 of heat transfer plates 2022 and 2026.

Furthermore, light from light source S enters luminaire 2010A, and heat transfer plate 2022 is positioned so that the optical path of light passes through one or more opening portions 2023.

According to this configuration, heat transfer plate 2022 passes, through opening portions 2023, light irradiated from light source S via lens array 2015. As a result, the amount of light to be emitted to the outside by luminaire 2010A can be maintained without reducing the amount of light.

Phosphor layer 2025 is formed so that the interface between phosphor layer 2025 and heat dissipation plate 2028 is flush with the interface between heat transfer plate 2026 and heat dissipation plate 2028.

According to this configuration, heat generated by phosphor layer 2025 is transferred to heat dissipation plate 2028 directly, that is, via neither board 2024 nor heat transfer plate 2026, and the heat transfer amount can be increased. As a result, the temperature increase of phosphor layer 2025 can be further prevented.

Opening portion 2023 of heat transfer plate 2022 is arranged on the optical path of incident blue light, and phosphor layer 2025 receives blue light and converts a part of received blue light to yellow light. One or more opening portions 2027 of heat transfer plate 2026 are arranged on an extension line of the optical path of blue light received by phosphor layer 2025, and pass therethrough white light generated from the blue light received by phosphor layer 2025 and the yellow light generated by conversion of phosphor layer 2025. Opening portion 2029 of heat dissipation plate 2028 is arranged on an extension line of the optical path, and passes therethrough the white light passed through one or more opening portions 2027 of heat transfer plate 2026 to the outside of luminaire 2010A.

According to this configuration, luminaire 2010A can emit white light to the outside by using incident blue light, and prevent the temperature increase of phosphor layer 2025.

Furthermore, lighting apparatus 2001 in this embodiment includes luminaire 2010A described above, light source S, and optical fiber F for leading light emitted from light source S to luminaire 2010A, and phosphor layer 2025 provided to board 2024 of luminaire 2010A receives light led by optical fiber F.

According to this configuration, lighting apparatus 2001 has the same effect as luminaire 2010A.

(Others)

The luminaire and the lighting apparatus according to the present invention have been described based on Embodiments 3 and 4, but the present invention is not limited to Embodiments 3 and 4.

The present invention contains configurations obtained by applying various modifications perceived by a person skilled in the art to the respective embodiments, and configurations realized by arbitrarily combining constituent elements and functions in the respective embodiments without departing from the subject matter of the present invention.

The invention claimed is:
1. A lighting apparatus comprising:
a wavelength conversion device;
a heat transfer plate arranged in surface contact with a board having light-transmissivity and including one or more portions that hold the phosphor layer of the wavelength conversion device, the heat transfer plate including one or more first opening portions at positions overlapping with the one or more portions, respectively; and
a heat dissipation plate that is arranged in surface contact with a surface of the heat transfer plate on a reverse side of a surface of the heat transfer plate that is in surface contact with the board, and includes a second opening portion at a position overlapping with the one or more first opening portions of the heat transfer plate,
wherein the wavelength conversion device includes:
a light source that emits light having a predetermined wavelength in a wavelength region from ultraviolet light to visible light;
a phosphor layer that performs wavelength conversion on light which is emitted from the light source and incident on an incidence face; and
an optical member that is arranged between the light source and the phosphor layer, splits and separates light emitted from the light source, and projects beams of the light that has been split and separated onto the incidence face of the phosphor layer.

2. The lighting apparatus according to claim 1,
wherein the board has a plurality of portions as the one or more portions, and
the heat transfer plate has a plurality of first opening portions as the one or more first opening portions, the plurality of first opening portions being arranged at positions overlapping with the plurality of portions, respectively.

3. The lighting apparatus according to claim 1,
wherein the heat transfer plate has a heat transfer body arranged to extend from a center portion of the heat transfer plate to a peripheral portion of the heat transfer plate.

4. The lighting apparatus according to claim 3,
wherein the heat transfer body is arranged at equiangular intervals around the center portion.

5. The lighting apparatus according to claim 1,
wherein the phosphor layer receives blue light incident on the phosphor layer, and converts a part of the blue light received to yellow light,
the one or more first opening portions of the heat transfer plate are arranged on an extension line of an optical path of the blue light received by the phosphor layer, and
the second opening portion of the heat dissipation plate is arranged on an extension line of the optical path, and passes white light generated from the blue light received by the phosphor layer and the yellow light generated by conversion of the phosphor layer to an outside of the lighting apparatus through the second opening portion.

6. The lighting apparatus according claim 1,
wherein the optical member is a microlens array,
a cross-sectional shape of the microlens array taken along a plane perpendicular to the incidence face is a sawtooth shape, and
the microlens array has a plurality of areas in which an arrangement direction of saw teeth is identical in a same area and different between different areas, the saw teeth consisting of a plurality of lenses, the arrangement direction being a direction in which the plurality of lenses in an area are linearly arranged.

7. The lighting apparatus according claim 1,
wherein the light emitted by the light source and split and separated by the optical member is projected onto an area of the incidence face without the beams of the light overlapping with one another, the area having a center on an optical axis of the light source and being larger than a diameter of the light emitted from the light source.

8. A lighting apparatus comprising:
a wavelength conversion device;
a heat transfer plate arranged in surface contact with a board having light-transmissivity and including one or more portions that hold the phosphor layer of the wavelength conversion device, the heat transfer plate including one or more first opening portions at positions overlapping with the one or more portions, respectively; and
a heat dissipation plate that is arranged in surface contact with a surface of the board on a reverse side of a surface of the board that is in surface contact with the heat transfer plate, and includes a second opening portion at a position overlapping with the one or more first opening portions of the heat transfer plate,
wherein the wavelength conversion device includes:
a light source that emits light having a predetermined wavelength in a wavelength region from ultraviolet light to visible light;
a phosphor layer that performs wavelength conversion on light which is emitted from the light source and incident on an incidence face; and
an optical member that is arranged between the light source and the phosphor layer, splits and separates light emitted from the light source, and projects beams of the light that has been split and separated onto the incidence face of the phosphor layer.

9. The lighting apparatus according to claim 8, further comprising:
an optical fiber that leads light emitted from the light source to the lighting apparatus,
wherein the phosphor layer receives the light led by the optical fiber.

10. A lighting apparatus comprising:
a wavelength conversion device;
a first heat transfer plate arranged in surface contact with a board having light-transmissivity and including one or more portions that hold the phosphor layer of the wavelength conversion device, the first heat transfer plate including one or more first opening portions arranged at positions overlapping with the one or more portions;
a second heat transfer plate that is arranged in surface contact with a surface of the board on a reverse side of a surface of the board that is in surface contact with the first heat transfer plate, and includes one or more second opening portions arranged at positions overlapping with the one or more portions, respectively; and
a heat dissipation plate that is arranged in surface contact with a surface of the second heat transfer plate on a reverse side of a surface of the second heat transfer plate that is in surface contact with the board, and includes a third opening portion at a position overlapping with the one or more second opening portions of the second heat transfer plate,
wherein the wavelength conversion device includes:
a light source that emits light having a predetermined wavelength in a wavelength region from ultraviolet light to visible light;
a phosphor layer that performs wavelength conversion on light which is emitted from the light source and incident on an incidence face; and an optical member that is arranged between the light source and the phosphor layer, splits and separates light emitted from the light source, and projects beams of the light that has been split and separated onto the incidence face of the phosphor layer.

11. The lighting apparatus according to claim 10,
wherein the board has a plurality of portions as the one or more portions,
the first heat transfer plate has a plurality of first opening portions as the one or more first opening portions, the plurality of first opening portions being arranged at positions overlapping with the plurality of portions, respectively, and
the second heat transfer plate has a plurality of second opening portions as the one or more second opening portions, the plurality of second opening portions being arranged at positions overlapping with the plurality of portions, respectively.

12. The lighting apparatus according to claim 11,
wherein the first heat transfer plate includes a first heat transfer body arranged to extend from a center portion of the first heat transfer plate to a peripheral portion of the first heat transfer plate, and
the second heat transfer plate includes a second heat transfer body arranged to extend from a center portion of the second heat transfer plate to a peripheral portion of the second heat transfer plate.

13. The lighting apparatus according to claim 12,
wherein the first heat transfer body is arranged in equiangular intervals around the center portion, and
the second heat transfer body is arranged in equiangular intervals around the center portion.

14. The lighting apparatus according to claim 10,
wherein a first opening portion of the first heat transfer plate is arranged on an optical path of blue light incident on the first heat transfer plate,
the phosphor layer receives the blue light, and converts a part of the blue light received to yellow light,
the one or more second opening portions of the second heat transfer plate are arranged on an extension line of the optical path of the blue light received by the phosphor layer, and passes white light generated from the blue light received by the phosphor layer and the yellow light generated by conversion of the phosphor layer through the one or more second opening portions, and
the third opening portion of the heat dissipation plate is arranged on an extension line of the optical path, and passes the white light passed through the one or more second opening portions of the second heat transfer plate to an outside of the lighting apparatus through the third opening portion.

* * * * *